(12) United States Patent
Huang et al.

(10) Patent No.: US 7,499,171 B2
(45) Date of Patent: Mar. 3, 2009

(54) METHODS FOR USING LIGHT REFLECTION PATTERNS TO DETERMINE DIVING ANGLE OF GRAIN

(75) Inventors: Chih-Lin Huang, Bellevue, WA (US); Stanley L Floyd, Enumclaw, WA (US); Mark A Stanish, Seattle, WA (US); David N Bogue, Federal Way, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 10 days.

(21) Appl. No.: 11/536,935

(22) Filed: Sep. 29, 2006

(65) Prior Publication Data
US 2008/0246971 A1    Oct. 9, 2008

(51) Int. Cl.
*G01N 21/47* (2006.01)
(52) U.S. Cl. .................... 356/446; 356/429
(58) Field of Classification Search ............ 356/446, 356/429, 430
See application file for complete search history.

(56) References Cited

U.S. PATENT DOCUMENTS

| | | | | |
|---|---|---|---|---|
| 4,606,645 | A | * | 8/1986 | Matthews et al. ............ 356/446 |
| 4,831,545 | A | * | 5/1989 | Floyd et al. .................... 702/40 |
| 4,926,350 | A | * | 5/1990 | Bechtel et al. ................. 702/36 |
| 5,252,836 | A | * | 10/1993 | Matthews et al. ....... 250/559.18 |
| 6,293,152 | B1 | * | 9/2001 | Stanish et al. .................. 73/597 |
| 6,305,224 | B1 | * | 10/2001 | Stanish et al. .................. 73/597 |
| 2008/0074670 | A1 | | 3/2008 | Carman |
| 2008/0078473 | A1 | * | 4/2008 | Huang et al. ................. 144/392 |

* cited by examiner

*Primary Examiner*—Roy M Punnoose
(74) *Attorney, Agent, or Firm*—Weyerhaeuser Law Department

(57) ABSTRACT

Methods are provided for using light reflection patterns to determine various properties of fibrous materials, such as wood. More specifically, the present invention relates to methods for determining a dive angle for grain. Further, the present invention relates to methods for using information in T2 plots, combined with knowledge of the microstructure of a wood sample surface, to find pith location and/or ring curvature.

14 Claims, 55 Drawing Sheets

METHODS FOR USING LIGHT REFLECTION PATTERNS TO DETERMINE DIVING ANGLE OF GRAIN

FIELD OF THE INVENTION

This invention relates generally to methods for using light reflection patterns to determine various properties of fibrous materials, such as wood.

BACKGROUND OF THE INVENTION

Spiral grain, taper, butt swell, knots, growth damage, and cutting patterns are factors related to grain deviation from the longitudinal edge of a piece of lumber. Grain deviation includes surface angle and dive angle. Surface angle is the angle between the grain direction (direction of trachea axis) and the longitudinal edge on the viewing surface of the piece of lumber. Dive angle is the tilting angle of the trachea axis with respect to the surface plane. Because wood is a highly anisotropic material, the grain direction of wood has a significant effect on strength, stiffness, and dimensional stability of wood products. The grain direction measurement is very useful for twist prediction, lumber strength grading, and knot delineation. Different scanning technologies that measure grain direction primarily identify lumber defects, evaluate lumber strength, and predict lumber warp propensity. Several of these technologies rely on a phenomenon known as the "tracheid-effect" whereby patterns of light scatter (both secular and diffuse) can be interpreted to infer geometric properties of the small fibers that constitute materials such as wood. A tracheid effect (Referred to as the T1 effect) is described in U.S. Pat. No. 3,976,384. The reflected shape of a round spot of laser light will appear elongated when reflected off the surface of wood. The direction of this elongation follows the axis of the tracheids. Another example, the "T2" concept described in U.S. Pat. No. 4,606,645 involves the projection of collimated light onto a fibrous web. The direction of the strongest reflection is perpendicular to the fiber axes. For diving grains, light reflected from the side and bottom walls of open tracheids cause the locations of the highest local reflection intensity to move toward the diving direction. The reflected light on end grain or knot is scattered or diffused. These phenomena are demonstrated in FIG. 1.

As shown in FIG. 2A, a laser scanning instrument (10) made by Plessey Company (UK) includes a ring of 72 sensors (12) with 5°(degree) pacing and measures the 45° (degree) light reflection (14) from a laser (16) shining straight down onto a wood surface (18).

FIG. 2B shows a schematic representation of laser light (16) striking the surface of wood (18), wherein the reflected light (14) is detected by sensors (12) arranged in a ring. An ideal plot of the reflected light intensities versus the azimuth angle around the ring has two symmetric peaks (local maximum intensities) and two valleys (local minimum intensities). Surface angle is indicated by the shift in peak locations (shown in FIG. 3). Diving or tilting brings the peaks closer together if the grain dives in the same direction, or farther apart if the grain dives in the opposite direction. As shown in FIG. 4, the peaks are closer together as the dive angle increases and the differences between the intensities at the valleys (the reflection from the bottom wall) increases with the dive angle.

The surface and dive angles can be calculated using the azimuth angle locations of these two peaks and the angle of the reflected light from the wood surface, otherwise referred to as the view angle (Matthews 1987). The applicable formulas are provided below:

$$\text{Surface angle} = (peak1 + peak2)/2 - 180$$

$$\text{Dive angle} = \arctan(\tan(\text{view angle}/2) * \cos((peak1 - peak2)/2))$$

These formulas were developed based on the assumption that the distribution of the orientation of the side wall on the surface is uniform. This assumption is valid only when the grain pattern has either perfectly vertical or perfectly flat grain and results in symmetric peaks of the same height. According to the formulas, where the view angle is known, the only data needed to calculate the surface and dive angles are the positions of these two peaks. A difference in peak heights can indicate the existence of ring curvature on the wood surface, which deviates from the assumption. There are errors involved in T2 dive angle calculation when peaks are too close together, or when one peak is significantly higher than the other, or when both situations occur. These errors can be observed by measuring the same spot while tilting or rotating the sample (Schajer & Reyes 1986, Prieve 1985).

Reducing the number of sensors and improving peak finding algorithms have been frequent research subjects of the T2 technology. A simplified design using 10 sensors demonstrated that sensors can be placed at a few critical locations to achieve a sufficient accuracy with a mean error in a range from 0.5 degree to 1.8 degree (Schajer 1986). It was found that to achieve these accuracies, the ring of sensors needed to have uniform sensitivity. The use of inverse parabola interpolation schemes also greatly reduced the errors of peak finding. The observed systematic errors were also found to be larger in dive angle calculation than in the surface angle calculation (Schajer & Reyes 1986). Variations of the twin-peak intensity pattern were observed to be related to surface roughness, damages, wane, and/or sample tilting. (Prieve 1985).

Most tracheid-effect interpretation models assume that the tracheid has a circular cross-section (FIG. 11 in U.S. Pat. No. 4,606,645) and no variation in the orientation of the side walls of the opened tracheid (referred to as the "simple model of a wood surface" (Matthews 1987)).

Surface roughness, ring curvature, and dynamic measuring condition (measuring while the sample is moving) are a few of the factors that affect the consistency of the surface and dive angle measurements, especially for high dive angles. The systematic "errors" reported in previous work (Schajer & Reyes 1986) (illustrated in FIG. 5) may be effects of certain unique patterns of wood structure, and therefore may convey useful information about the structure. Note the greater systematic errors in dive angle than in surface angle prediction.

Such inconsistency in measuring dive angles around a knot tends to cause over-estimation of the size of a knot. Accurate estimation of the size of knots optimizes the recovery of clear wood from remanufacturing operations and improves the accuracy of sorting visual grades of structural lumber. The location of pith is required to estimate the size of knots within a piece of lumber. Therefore, the accuracy of knot size estimation can be improved by measuring the ring curvature or the pith location using a T2 scanning system.

Lumber twist propensity can be inferred from the dive and surface angle patterns within the clearwood (no knots) areas of the lumber. Accordingly, a need exists for a method of using T2-related information to infer clearwood locations and exclude data from non-clearwood locations. A further need exists for a method of using other information in T2 reflection patterns, combined with the knowledge of the wood surface microstructure, to find pith location and ring curvature.

BRIEF DESCRIPTION OF THE DRAWINGS

The embodiments of the present invention are described in detail below with reference to the following drawings.

FIGS. 23A-F illustrates plots showing the variation of P1-P2 values on opposite faces of the wood strips shown in FIGS. 9A (FIGS. 23 A-C) and 9B (FIGS. 23D-F), wherein FIGS. 23A and 23D represent dive angles of 15°, FIGS. 23B and 23E represent dive angles of 7.5°, and FIGS. 23C and 23F represent dive angles of 0°, (the x-axis is the distance in ¼" units, and P1-P2 was calculated by the differences of sensors around 90° and 270°, assuming zero surface angle.

DETAILED DESCRIPTION OF THE INVENTION

The present invention relates generally to methods for using light reflection patterns to determine various properties of fibrous materials, such as wood. Wood samples may be any type, including green, dried, or any other form or condition of lumber known to those skilled in the art. More specifically, the present invention relates to methods for determining a dive angle for grain. Further, the present invention relates to methods for using information in light reflection patterns, combined with knowledge of the microstructure of a wood sample surface, to find pith location and/or ring curvature. The light that is projected toward the fibrous material may be any type of light capable of producing a T2 effect. Such types of light are known by those skilled in the art.

The invention may be better understood by the following example:

EXAMPLE 1

Figure 6:
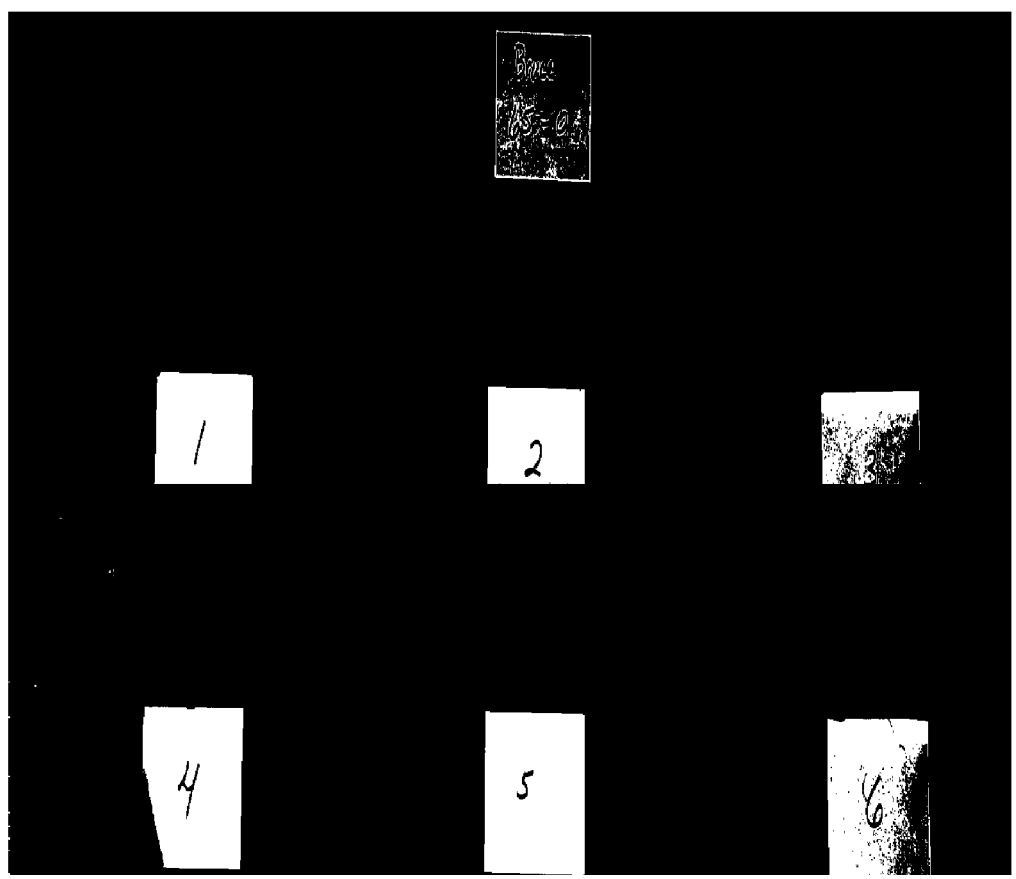
FIG. 6 is an example of sixteen-inch segments taken from 8 foot long, 2 inch by 4 inch boards.

A batch of wood samples included 23 pieces of eight-foot 2×4 (2 inch by 4 inch) pieces, each cut at different locations from one of 23 pieces of 16 foot lumber from Weyerhaeuser Company owned and operated mills (Dierks and Bruce). Warp of the lumber was quantified after conditioning at different relative humidity. Each piece of the 2×4 batch was cut into 16 inch segments. Examples of the wood pieces are provided in FIG. 6.

Figure 7:
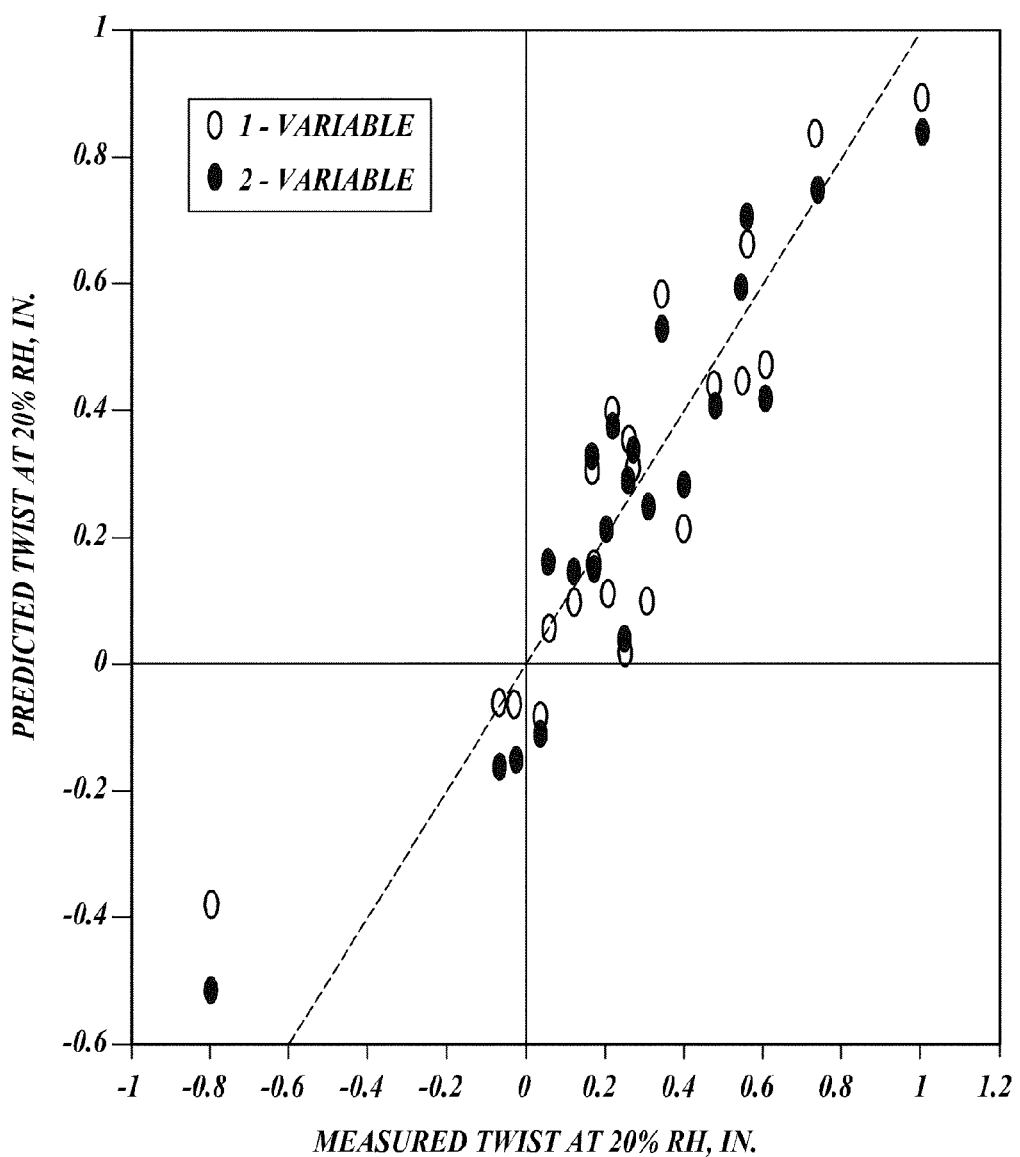
FIG. 7 is a plot of the results of twist prediction using dive angle calculated from the T2 Scanning System, wherein the open symbols represent dive slope (1-variable) and the filled symbols represent dive slope plus surface angle differential (2-variable)

Fifteen T2 reflection measurements were taken on both wide faces of each piece in a 5-wide×3-along grid pattern. (total of 30 points per piece). Surface and dive angles were determined from these measurements. This dataset was used as the input for a twist model based on a method described in U.S. Pat. No. 6,293,152. Some of the high dive angle outliers were excluded or masked from the twist prediction model. The results were quite good and are illustrated in FIG. 7.

Figure 8:
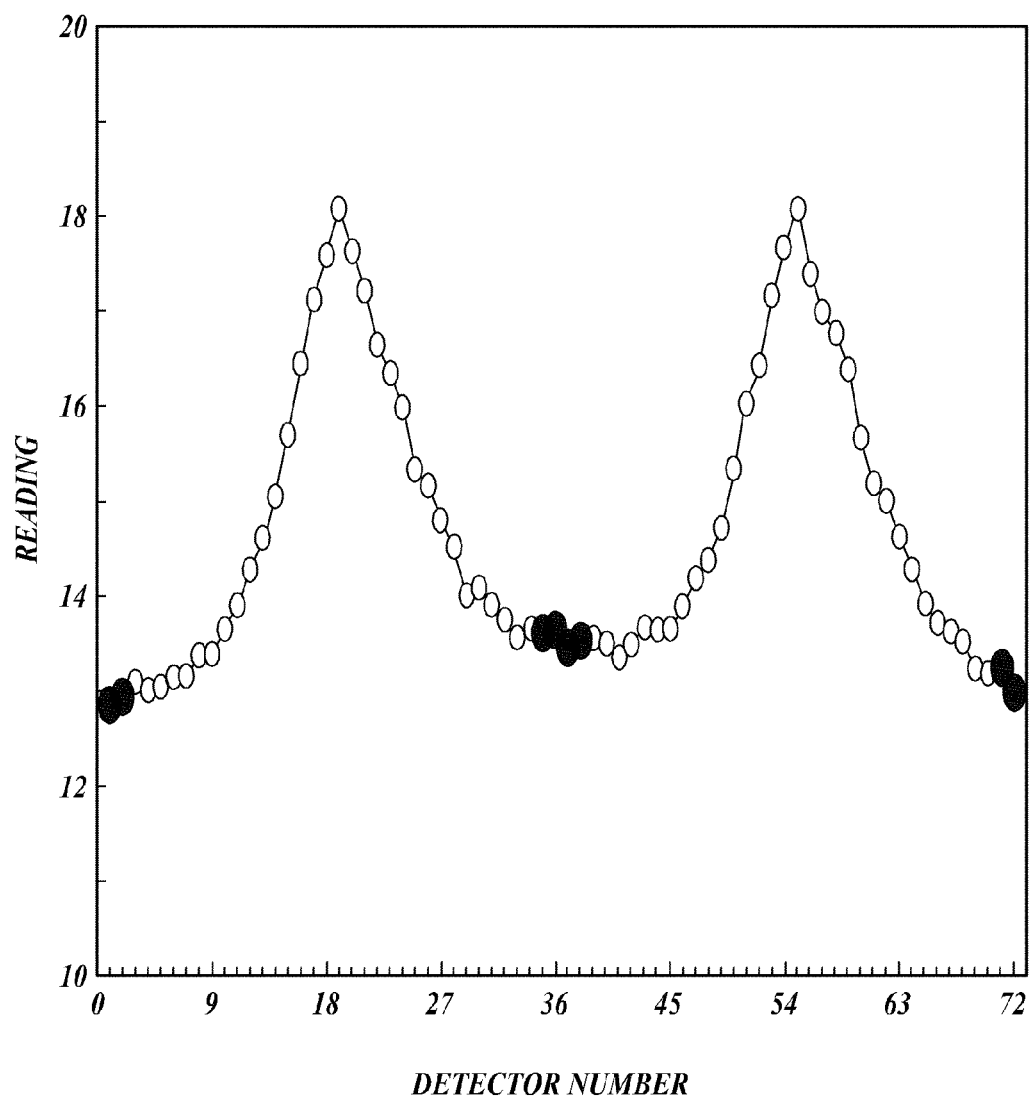
FIG. 8 is a plot of data from the four closest sensors at the bottom of the valleys V1 and V2.

Using the previously described Plessey T2 sensor composed of a ring of 72 detectors, local minimum intensities (valleys) were observed at detector locations that are aligned with the tracheid axis of the illuminated wood surface. Referring to FIG. 8, it is expected that the first valley to occur in the vicinity of sensor locations 71, 72, 1 and 2 and the second valley to occur in the vicinity of sensor locations 35, 36, 37 and 38. Valley intensities are defined as follows:

V1=average intensity of detectors 71, 72, 1, and 2.
V2=average intensity of detectors 35, 36, 37 and 38.

For a wood surface with no dive or surface angle, the local maximum intensities (peaks) are perpendicular to the tracheid axis. The first peak is in the vicinity of sensor locations 17, 18, 19, and 20 and the second peak in the vicinity of sensor locations 53, 54, 55, and 56. Peak intensities are defined as follows:

P1=average intensity of detectors 17, 18, 19, and 20.
P2=average intensity of detectors 53, 54, 55, and 56.

Figure 9A:
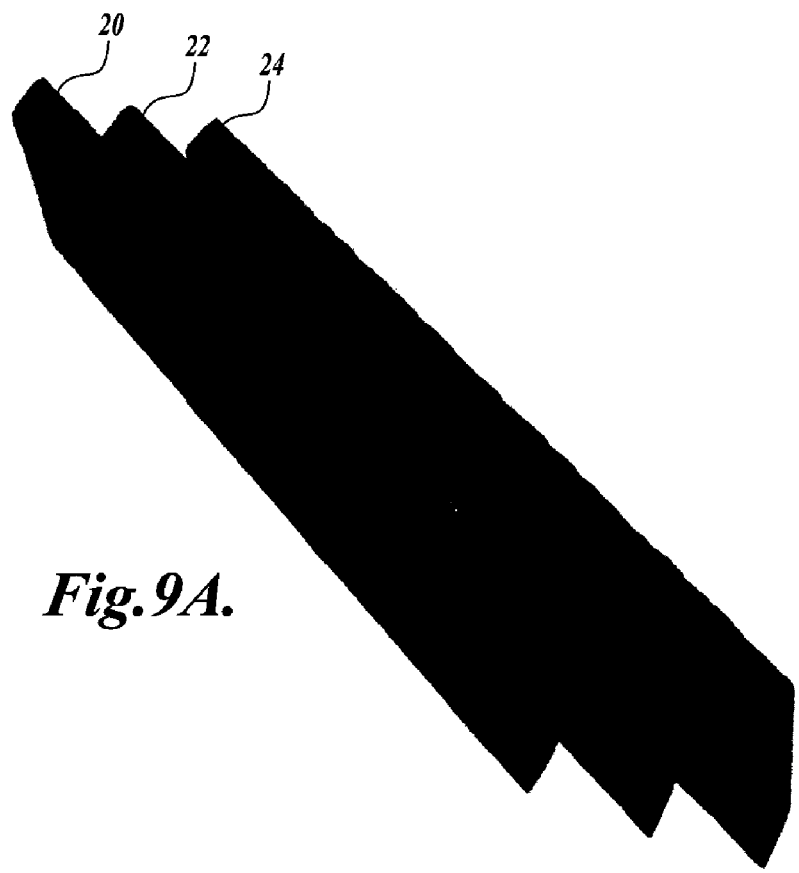
FIGS. 9A-B illustrates an example of wood strips with approximately 0°, 7.5°, and 15° dive angles on top (FIG. 9A) and bottom (FIG. 9B) surfaces of a lumber segment.
Figure 9B:
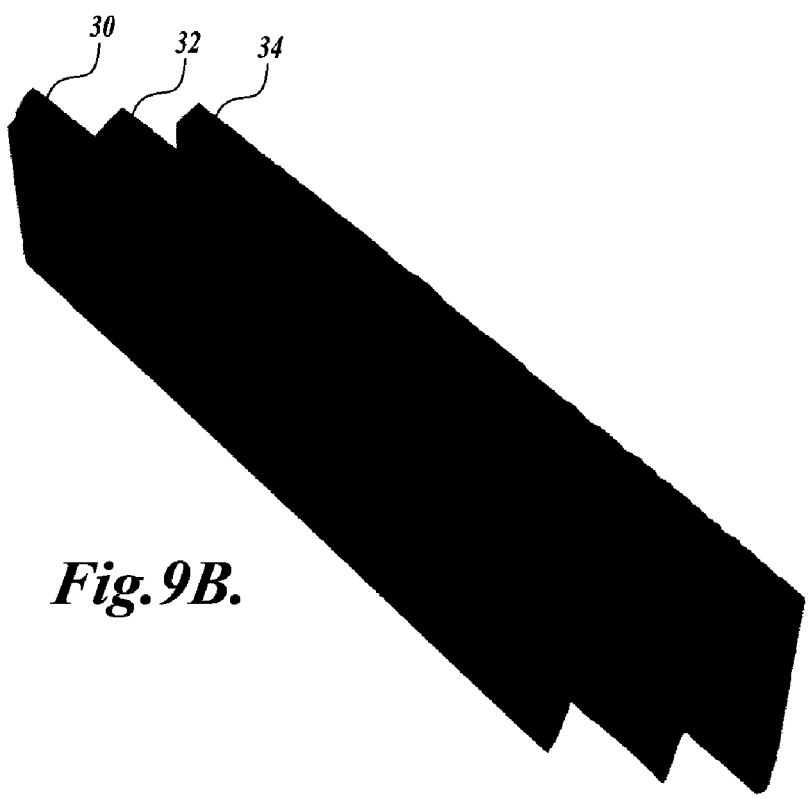

A relationship between the ring curvature and peak height differences (P1-P2) was observed in the results of the batch of 16" samples. A second batch of samples with known dive angle and ring curvature was prepared for further investigation of the observed relationship. Five segments of lumber, each with different ring width and ring curvature, were selected and six half-inch wide strips of specimens were cut from each lumber segment. Three top surfaces (20, 22, 24) and three bottom surfaces (30, 32, 34) of the strips were planed to produce approximately 0° (20, 30), 7.5° (22, 32), and 15° (24, 34) dive angles. These samples are shown in FIGS. 9A and 9B. T2 scans were taken on the planed surface of the strips using quarter-inch spacing.

1. Using Peak Finding and Valley Differences to Predict Dive Angle

Figure 10:
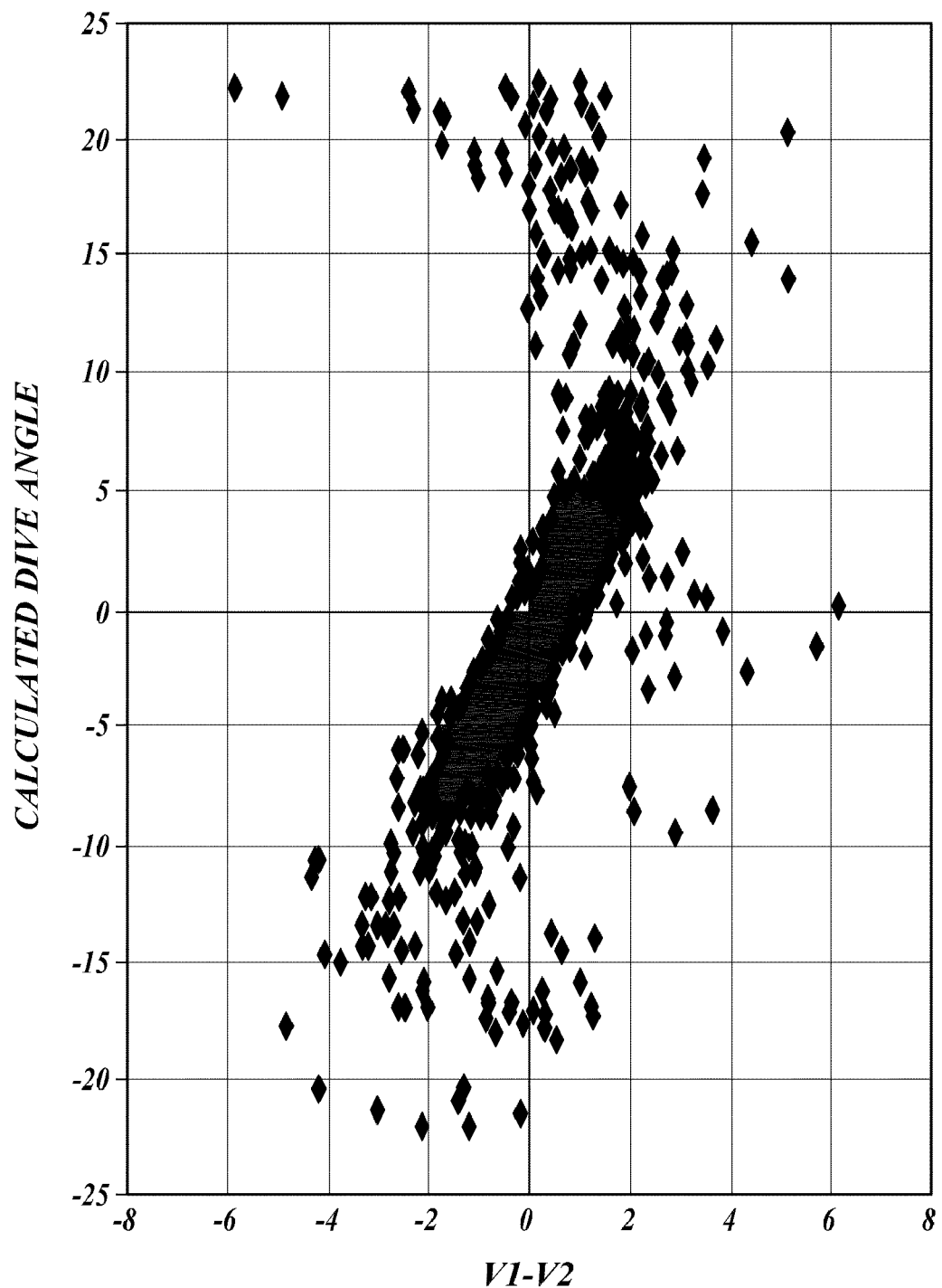
FIG. 10 is a plot showing the relationship between V1-V2 and the calculated dive angle.
Figure 11A:
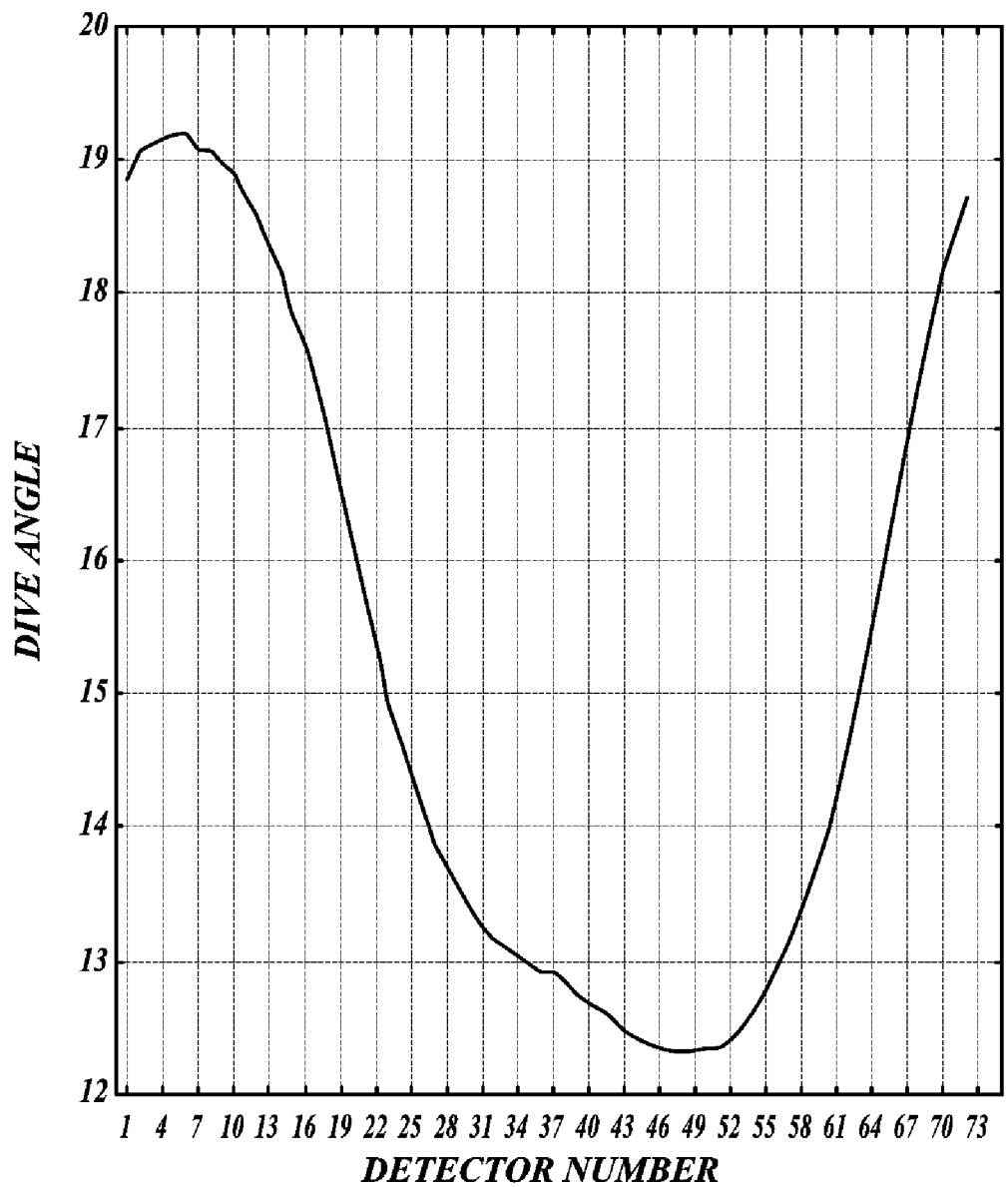
FIGS. 11A-I provides examples of intensity plots of high dive angle areas in a wood sample.
Figure 11B:
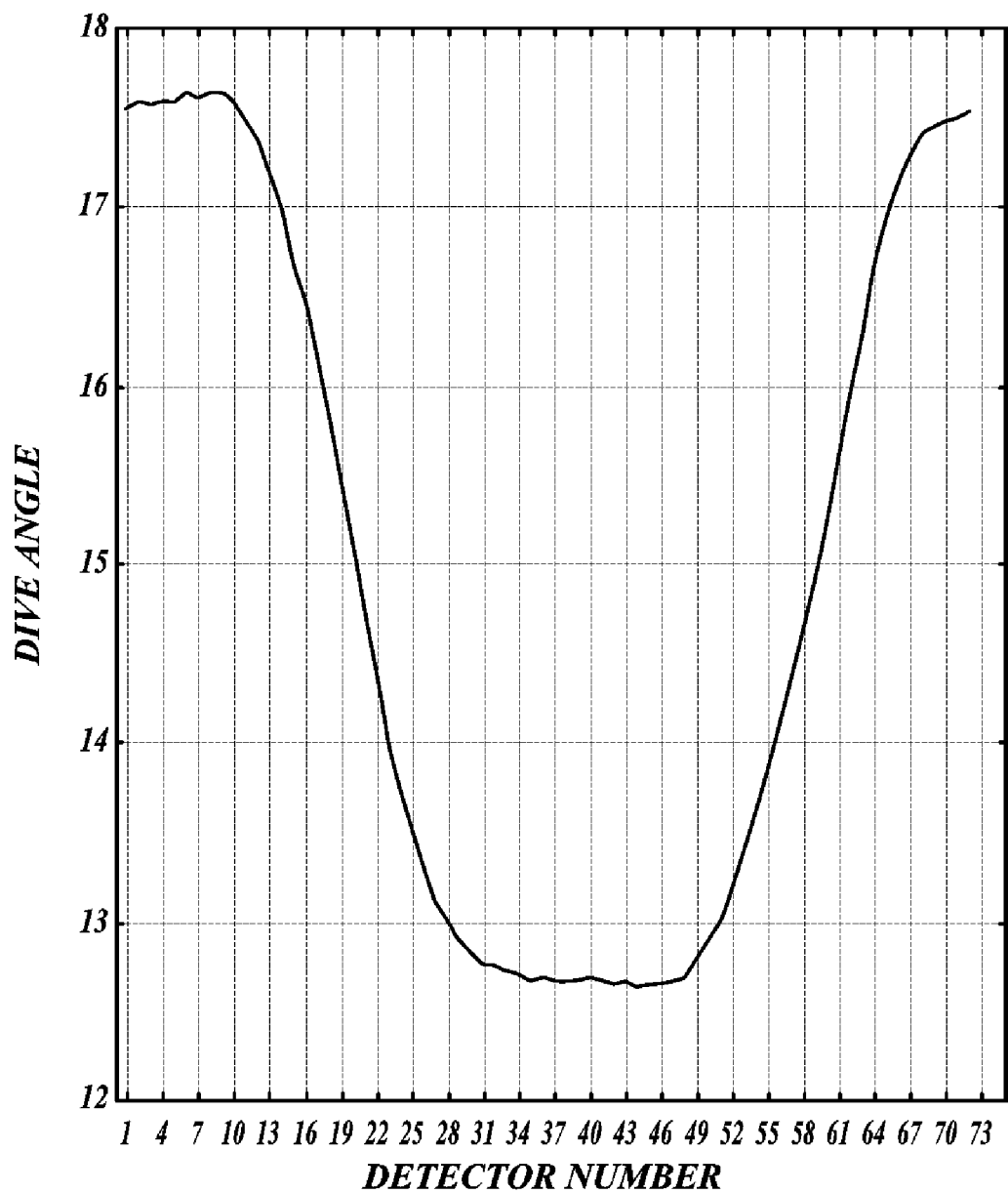
Figure 11C:
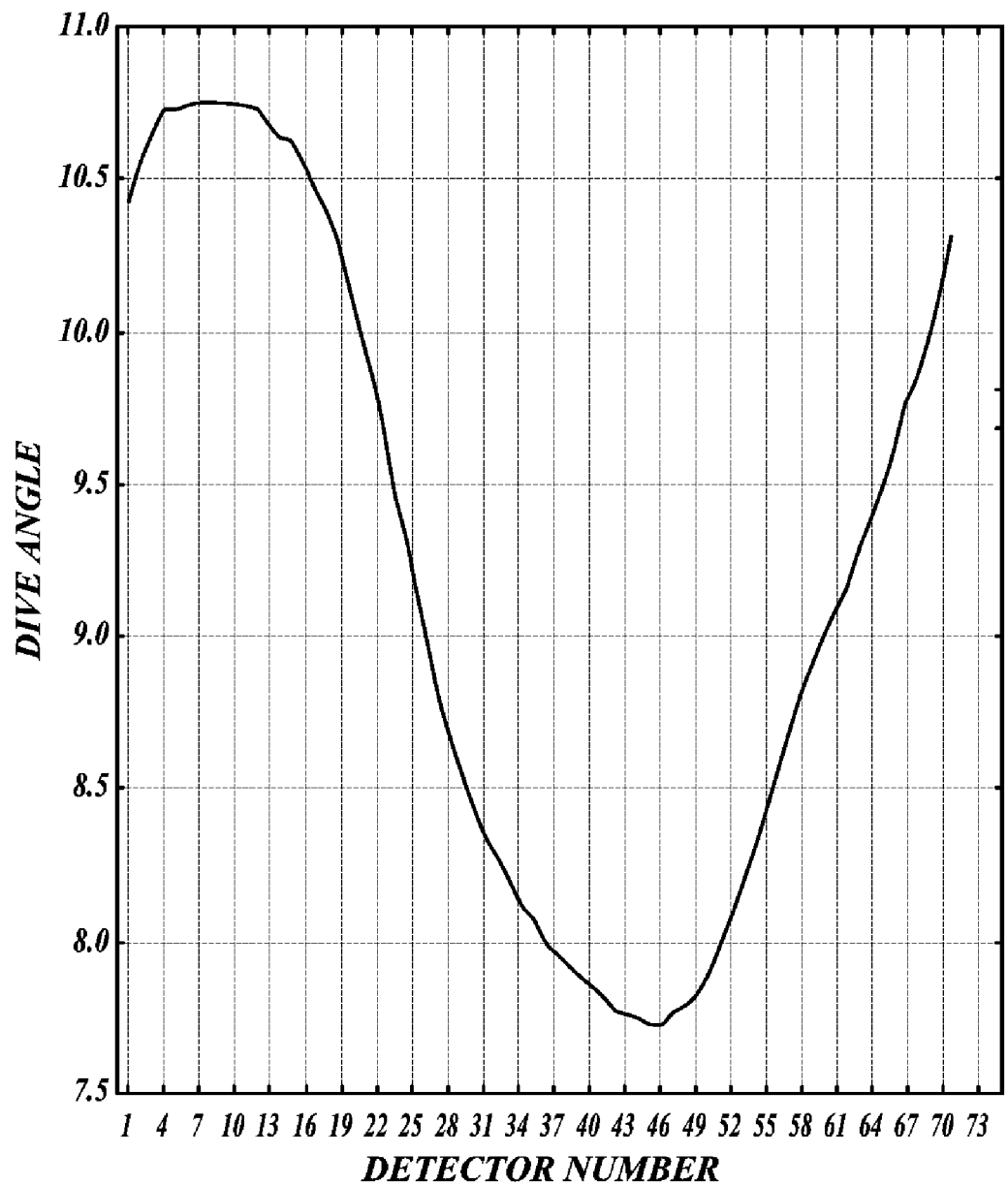
Figure 11D:
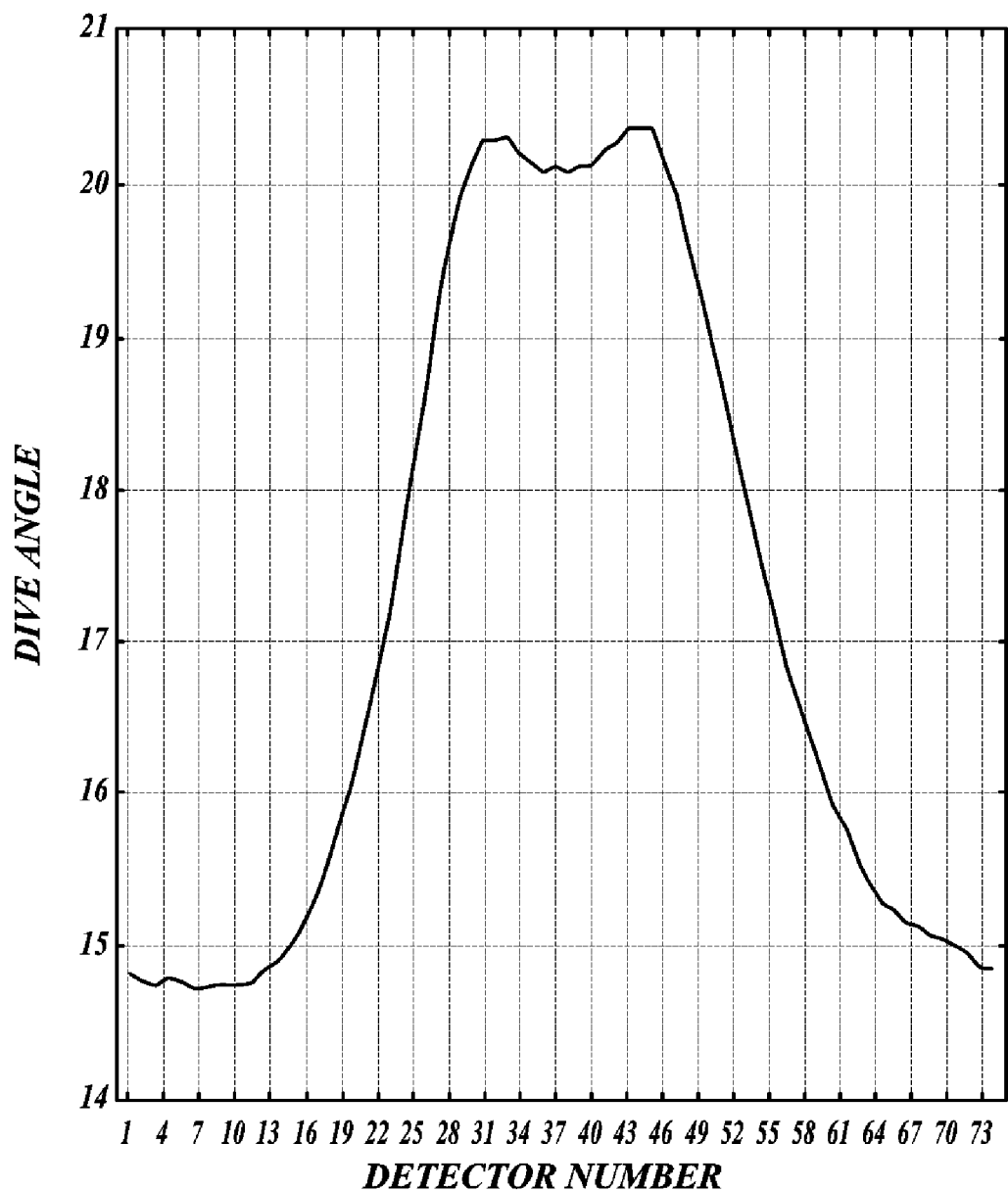
Figure 11E:
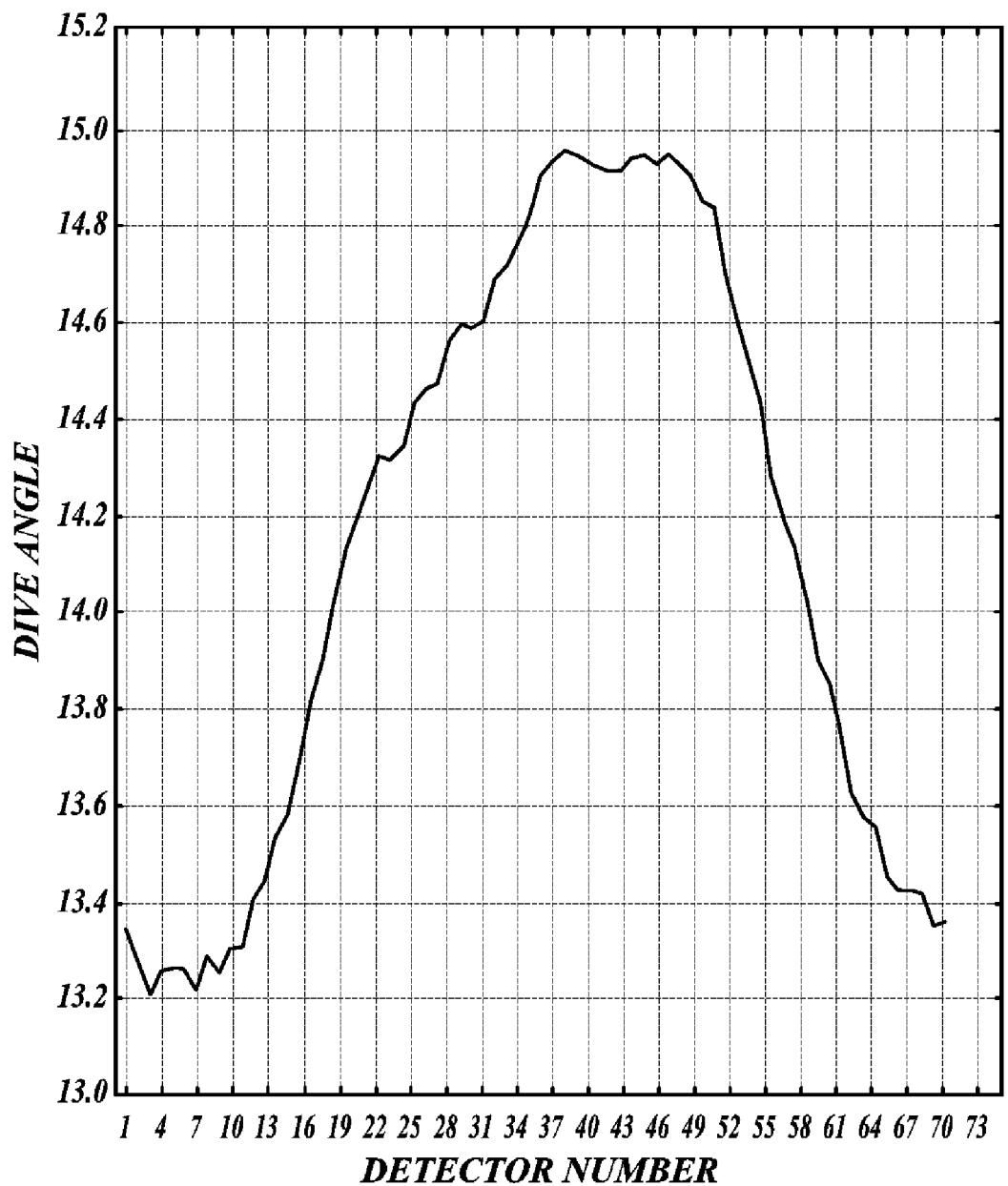
Figure 11F:
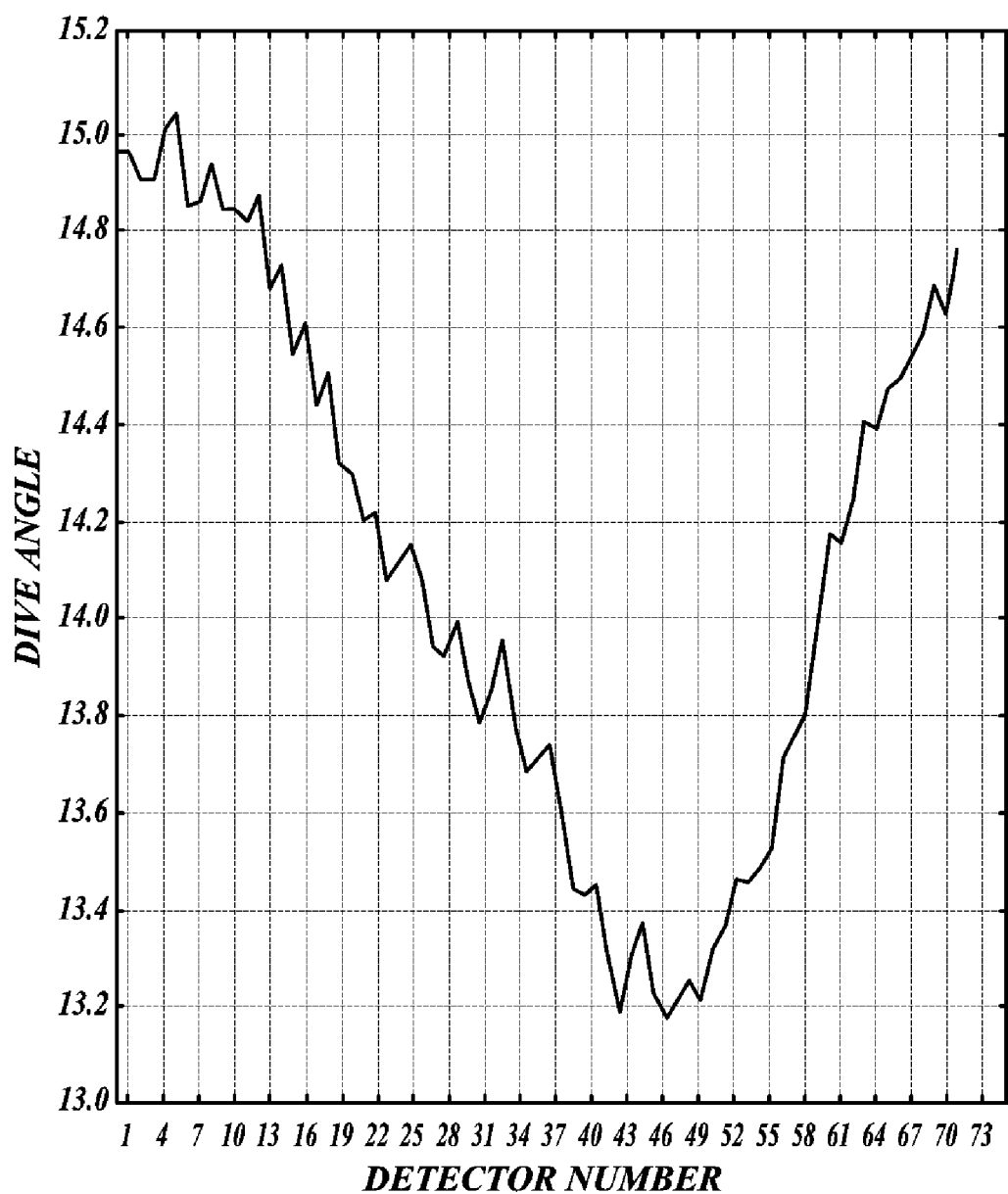
Figure 11G:
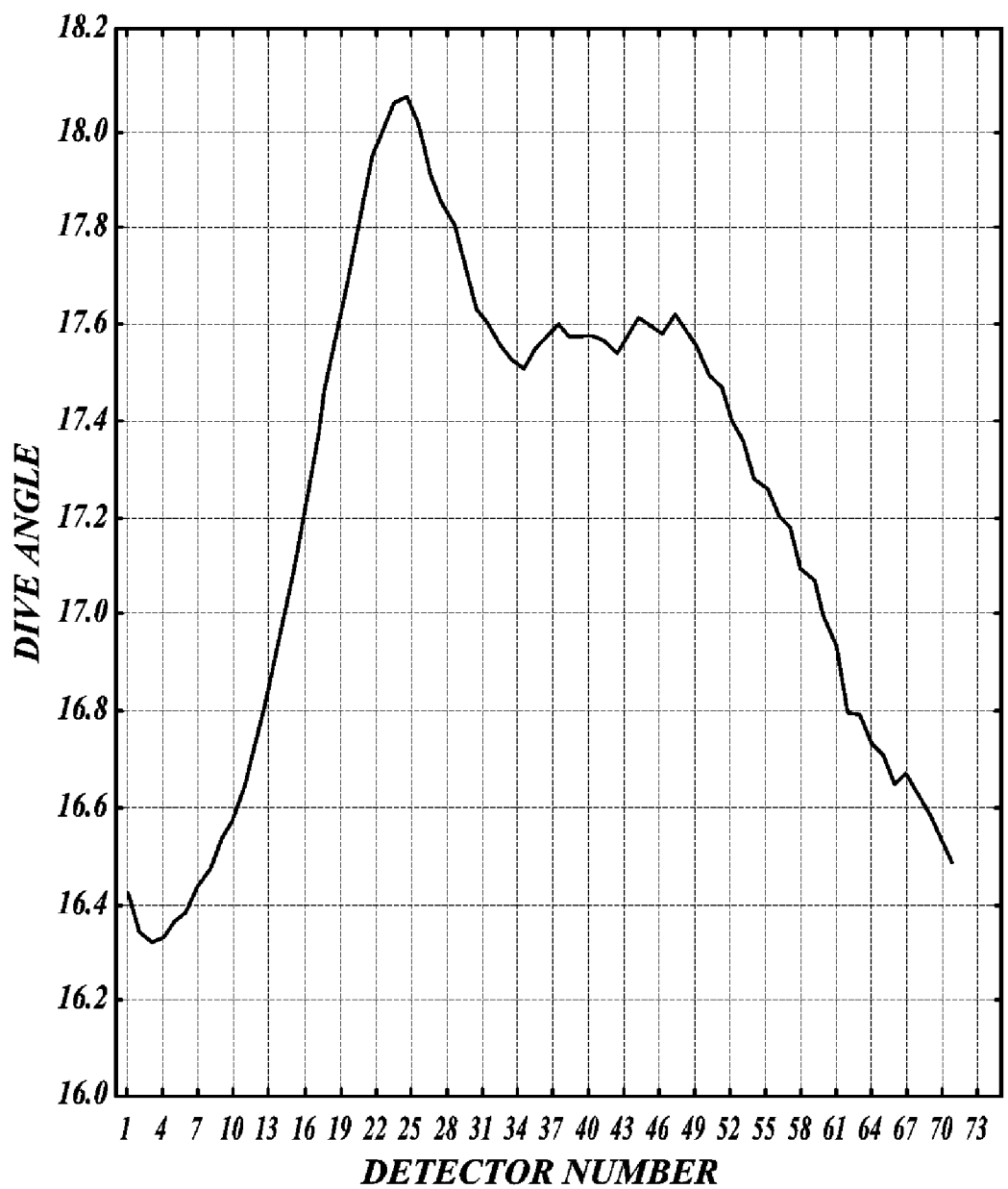
Figure 11H:
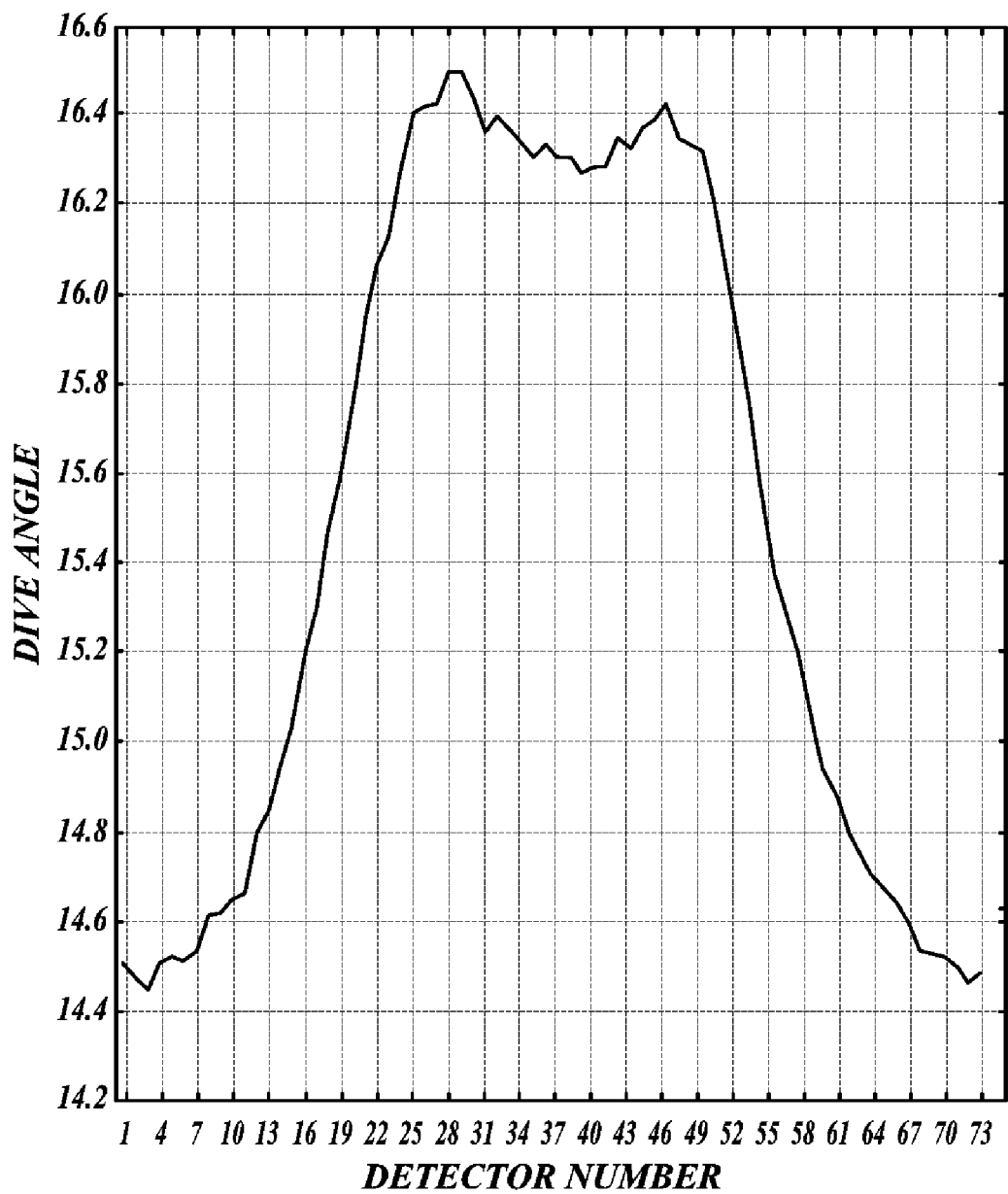
Figure 11I:
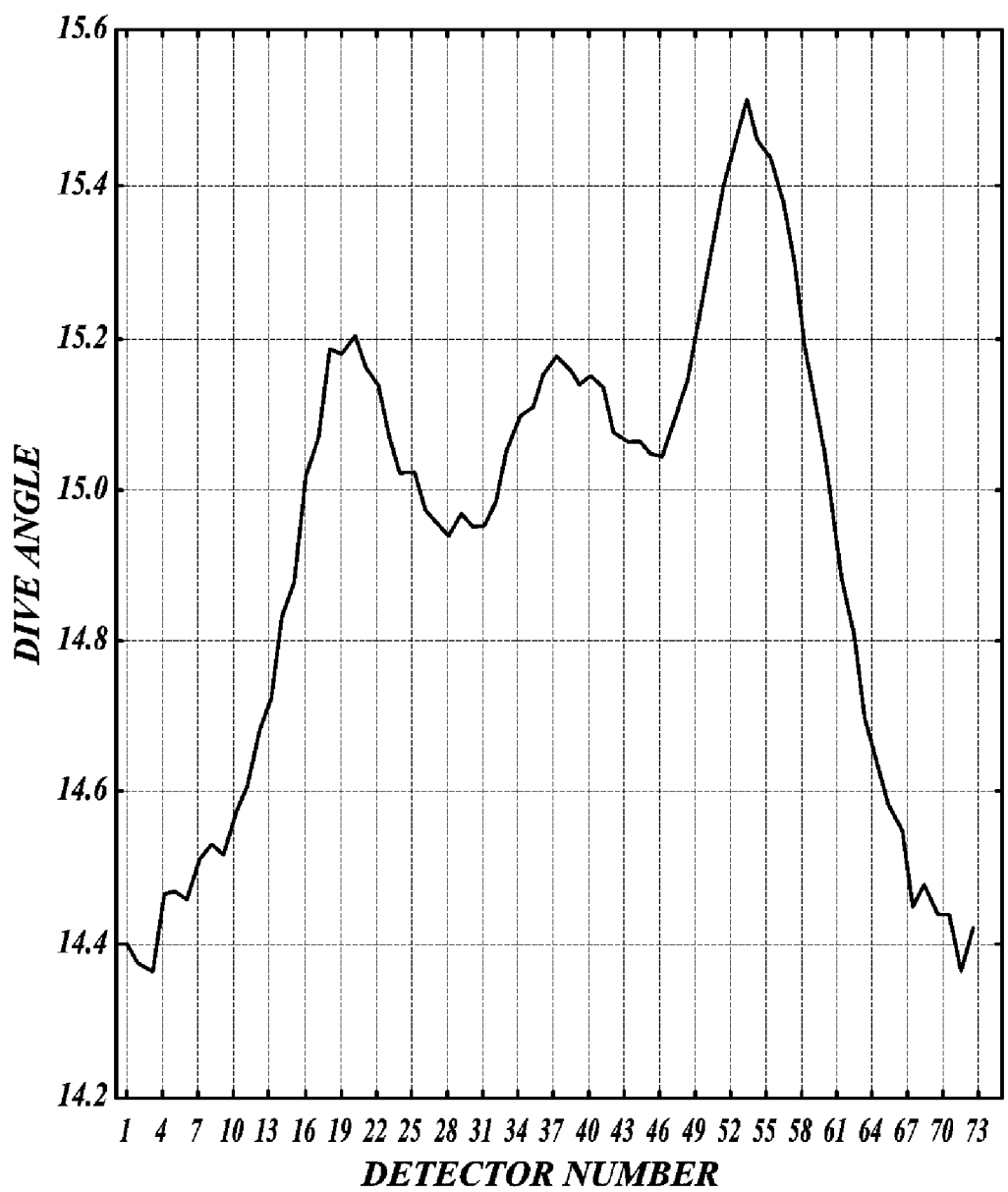

The correlation between V1-V2 dive angle is better at low (<10°) dive angles (see FIG. 10). Accordingly, the predicting model should be built using data in this range. The reflected intensity patterns must be normalized to minimize noise effects caused by a variety of factors such as surface roughness, detector sensitivity variation, etc.

Within a T2 detector ring, those that are oriented at azimuth angles in alignment with the tracheid axis will detect the lowest amount of specular reflection (relative valleys). These relative valleys are much "flatter" than the peaks (i.e. similar low intensity levels are sustained among adjacent detectors). As a result, the difference between intensities of the two relative valleys can be observed by multiple detector pairs in those flat regions. As a result, if surface angle is small (<10 degrees) the relative valley differences will be detected by sensor pairs that are aligned with the axis of the lumber (and not necessarily the axis of the tracheids). Thus measuring the difference between relative valley intensities can be accomplished with as few as 2 detectors positioned 180 azimuth degrees from each other and oriented along the length axis of the lumber.

Figure 1A:
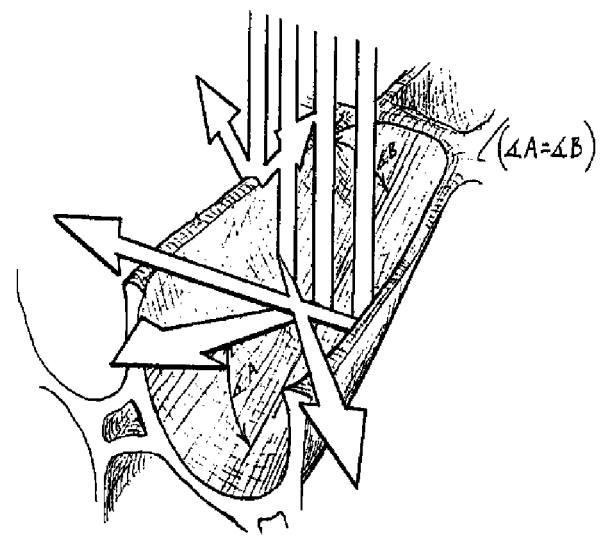
FIGS. 1A-C illustrates diagram of the reflections of light on a wood surface having flat, dive and vertical grains.
Figure 1B:
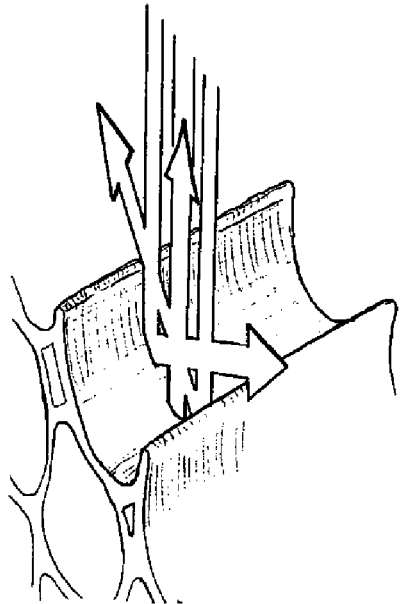
Figure 1C:
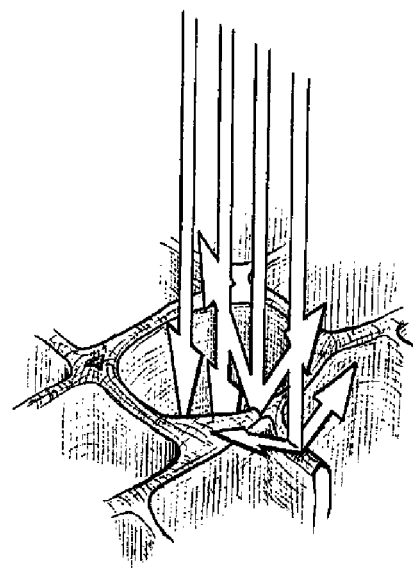
Figure 2A:
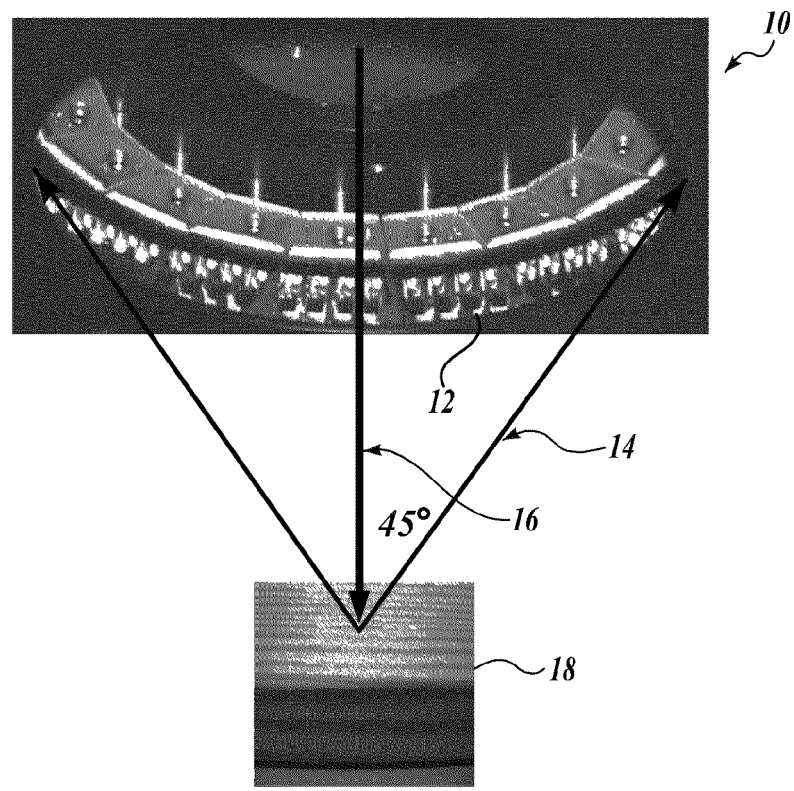
FIGS. 2A-B illustrates is a T2 scanning system.
Figure 2B:
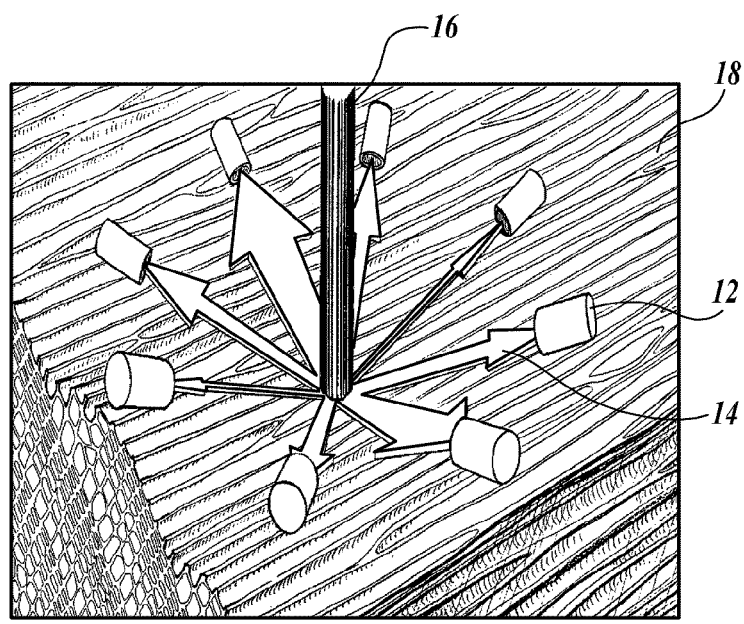
Figure 3A:
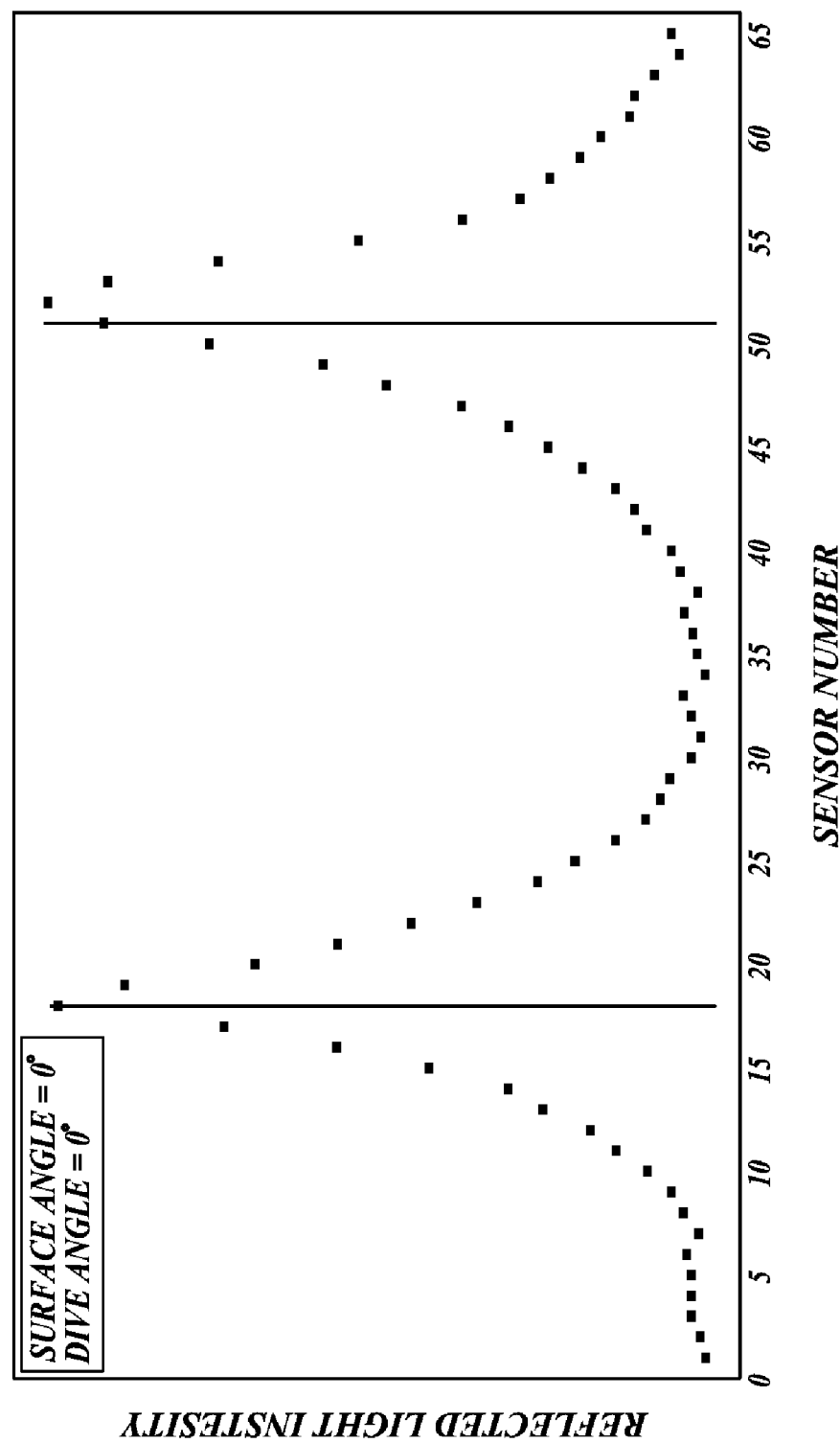
FIGS. 3A-B illustrates is a plot of intensity traces of 72 sensors showing the shift in peak locations between a 0° surface angle (FIG. 3A) and a 30° surface angle (FIG. 3B)
Figure 3B:
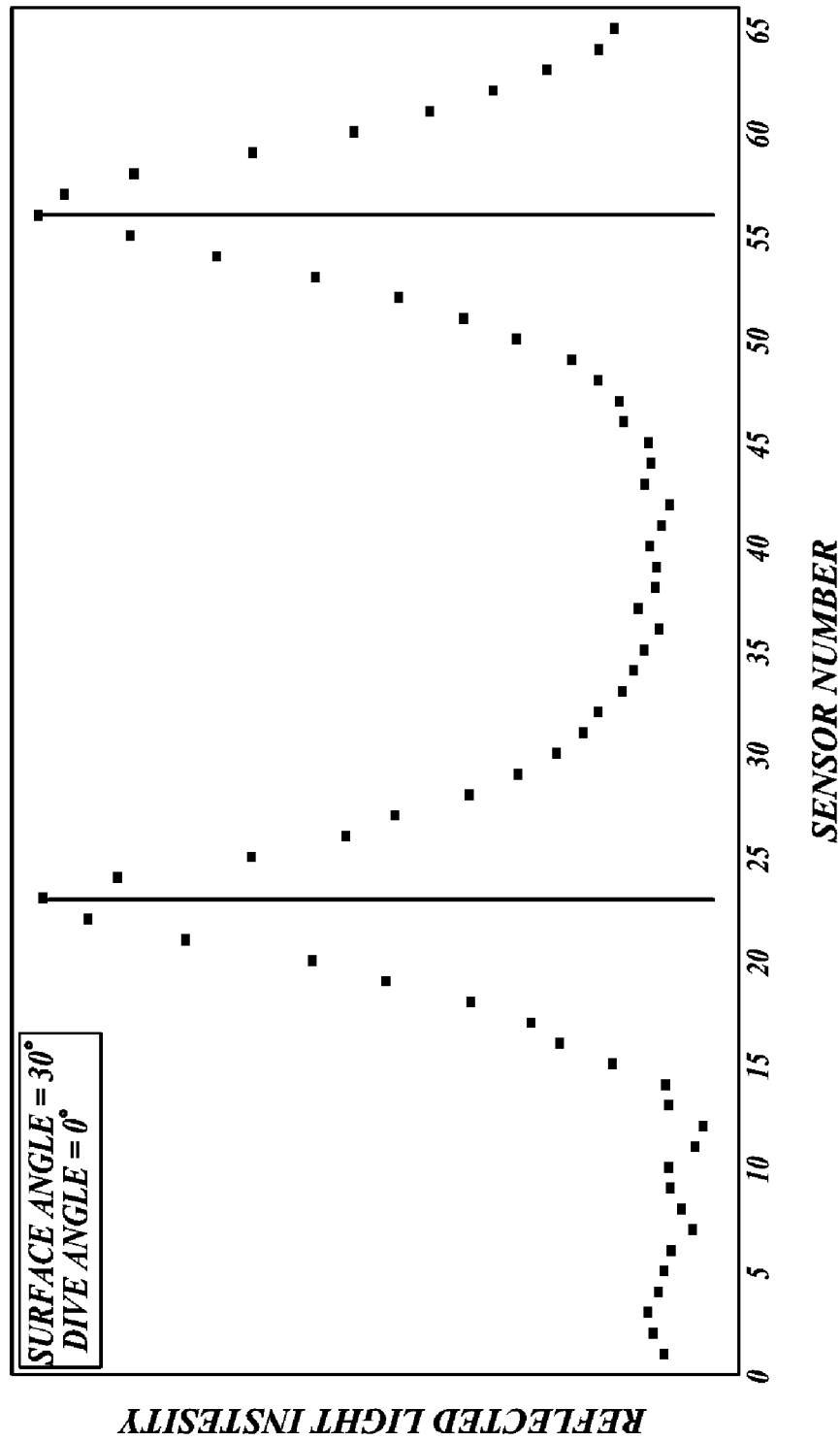
Figure 4A:
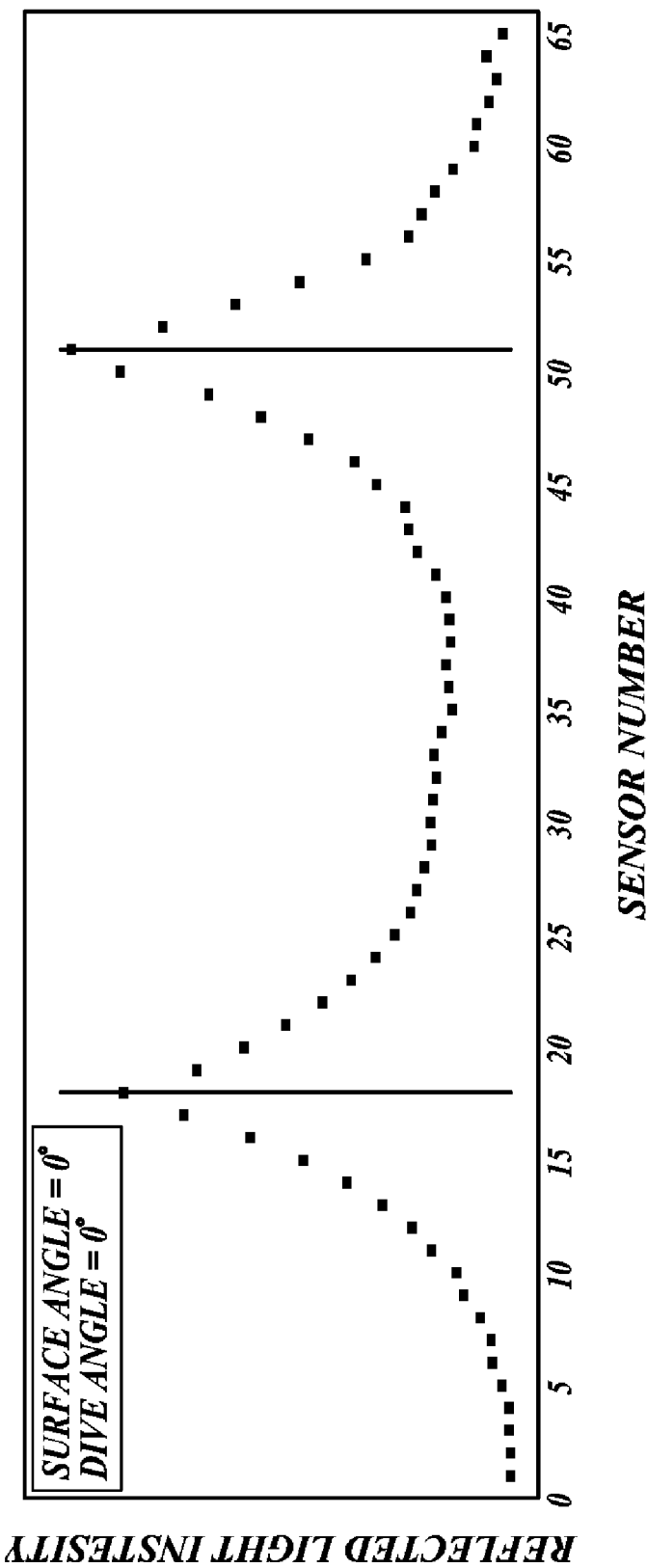
FIGS. 4A-C illustrates shows plots of intensity traces of increasing dive angle, wherein surface angle equals 0°, and dive angle equals 0° (FIG. 4A), 9° (FIG. 4B), and 13° (FIG. 4C)
Figure 4B:
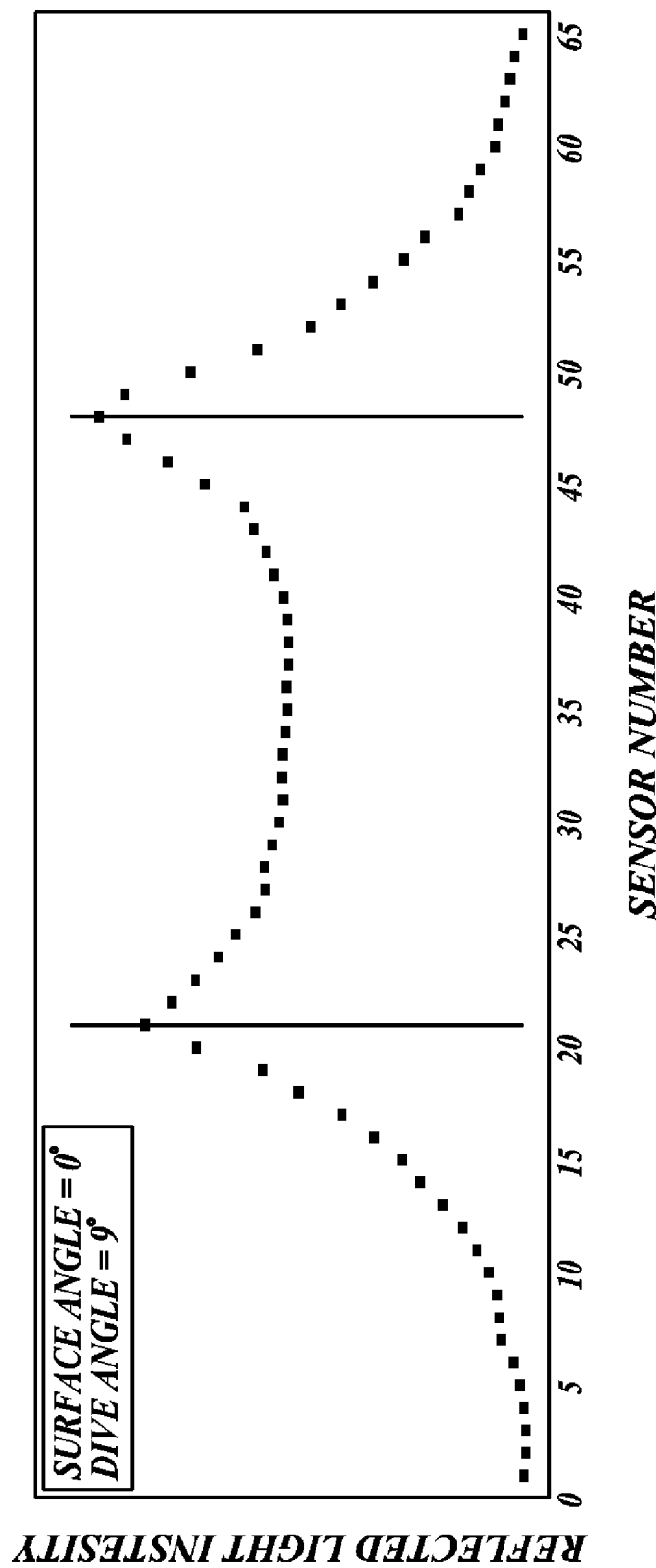
Figure 4C:
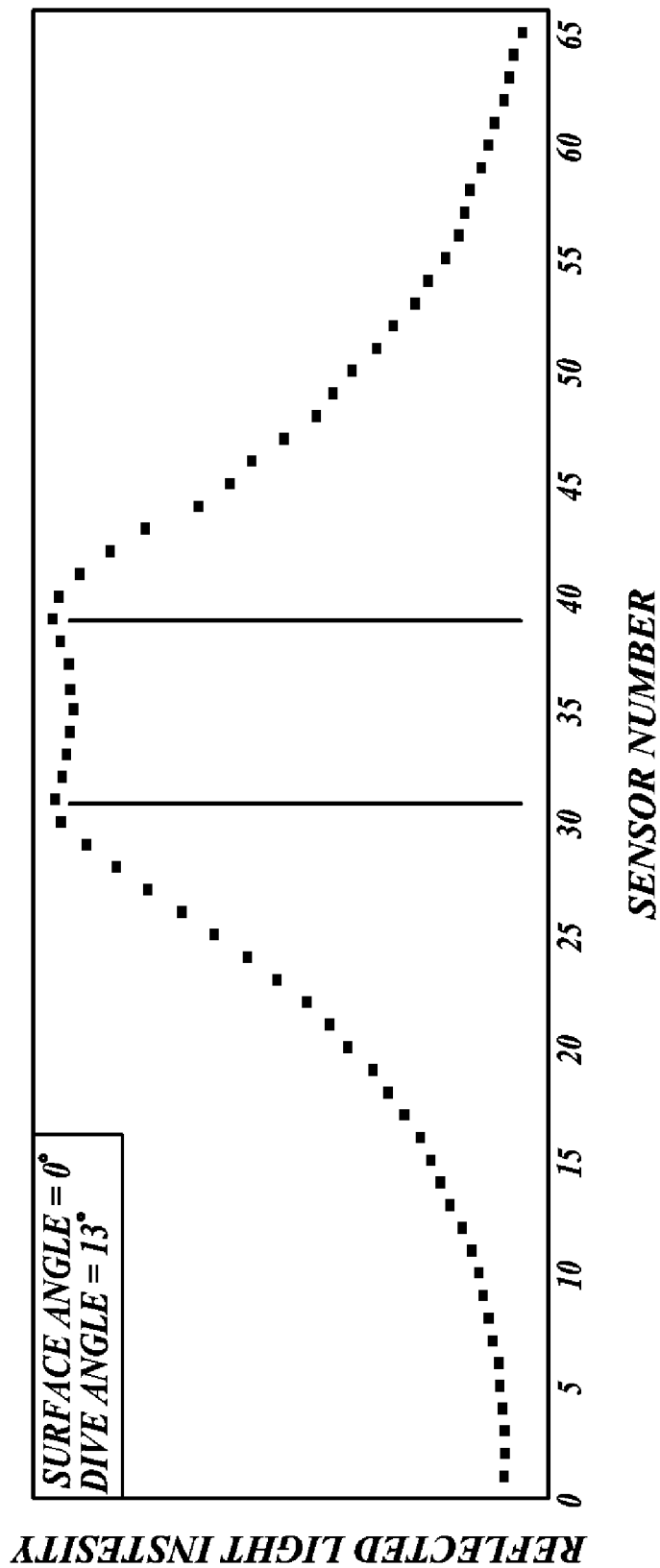
Figure 5A:
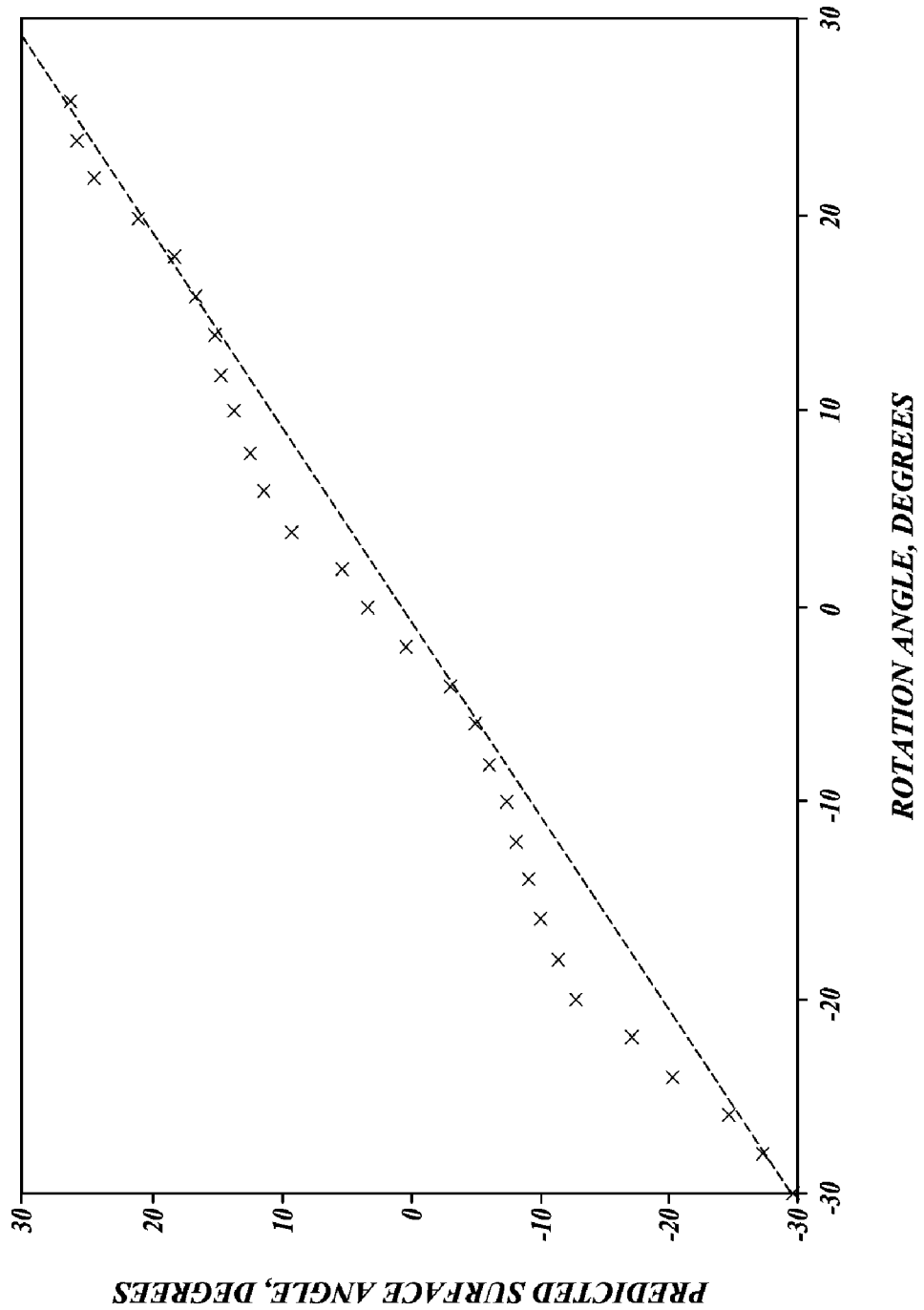
FIGS. 5A-B illustrates a plot of predicted surface angle vs. specimen rotation angle (FIG. 5A) and a plot of predicted dive angle vs. specimen rotation angle (FIG. 5B), wherein the symbols (X) represent measured angles and the dashed line represents predicted values.
Figure 5B:
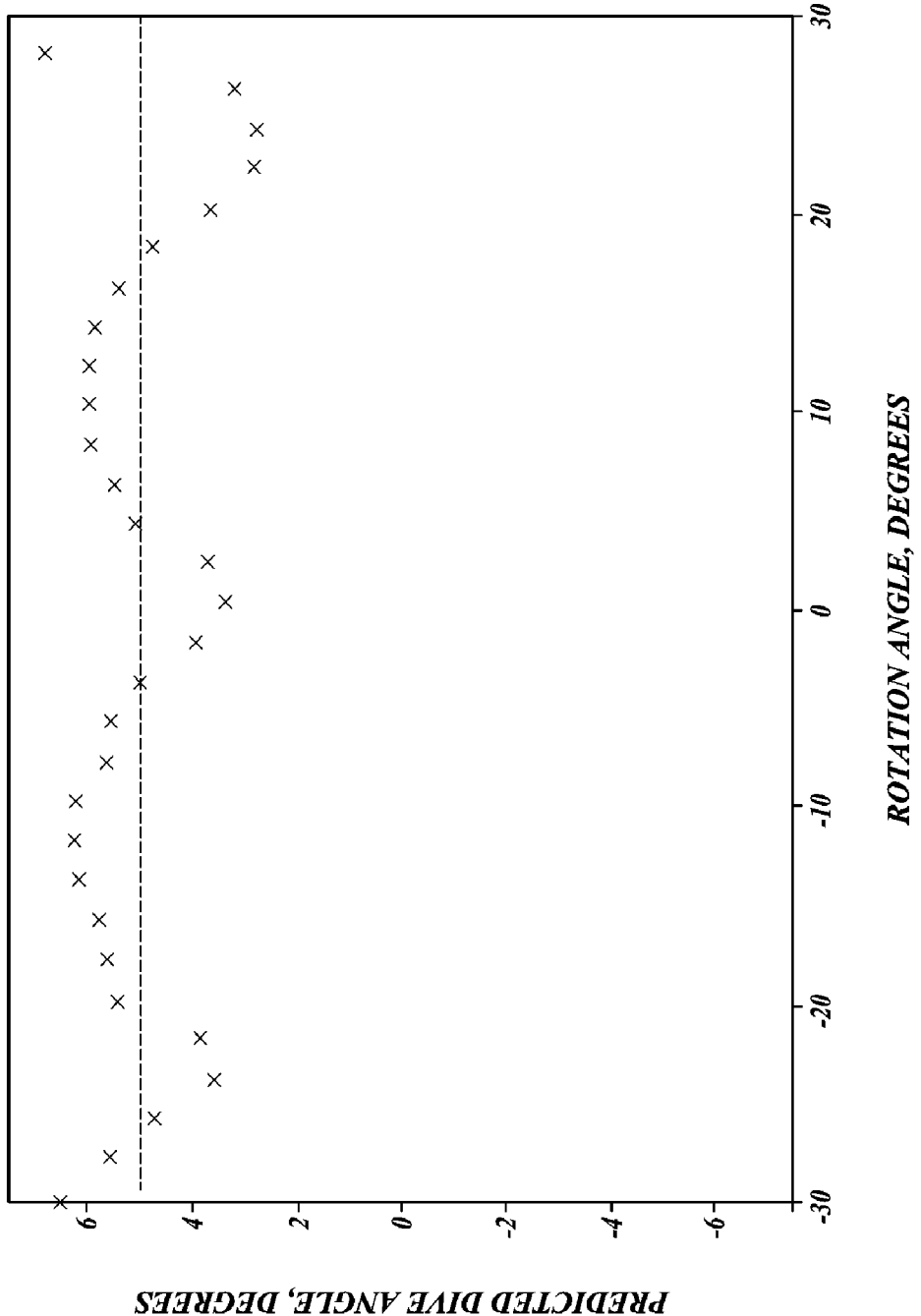

For smaller dive angles, the peaks of the intensity patterns are well-separated and easy to see (FIGS. 3A and 3B) and the peaks can be consistently identified by peak finding algorithms. These algorithms are known by those skilled in the art. When the dive angle is large, the two peaks merge together and are more difficult to separate because the intensity patterns merge into a single broad peak with single or multiple humps and a broad valley (see FIGS. 11A-11I). Consequently, it is very difficult to find the location of the two peaks when the dive angle is large. If the surface angle is small, a large dive angle can be predicted via the formula V1-V2 using the established dive angle calibration model. It is likely that predicting dive angle using the valley difference yields more consistent results than using the peaks, especially when the dive angle is large.

Figure 12:
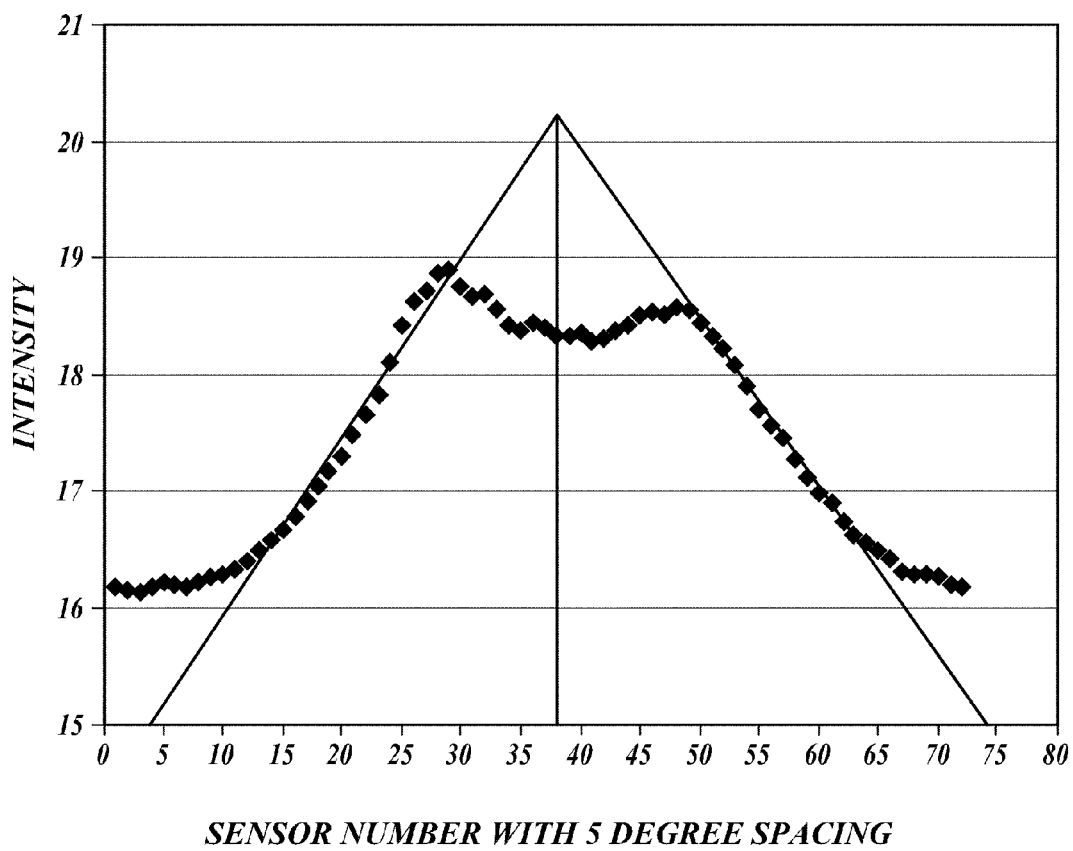
FIG. 12 is plot of an example of a determined surface angle on a curve showing only one single broad peak (a typical T2 sensor intensity trace at a high dive angle area), wherein the valley bottom is at sensor number 2, the broad peak center is at sensor number 38, and the surface angle equals 10 degrees.

Dive angle estimation is more complicated when surface and dive angles are both large, as when the 180 degree between-valley spacing is maintained but the positions of the sensors are rotated. The true locations of V1 and V2 can be determined by finding either the center of the broad valley or the broad peak. Different algorithms, such as the one used to analyze the X-ray diffraction patterns of softwood tracheid (Verrill et al. 2001), can be used to find the locations of the valleys and the peaks. Visually, the bottom of the valley and the center of the broad peak are located by the intersection of two lines drawn tangent to the peak (as illustrated in FIG. 12).

Once the true locations of V1 and V2 are known, V1-V2 is calculated to predict dive angle using the model. Referring to the plot of intensity vs detector azimuth angle, surface grain angle can be estimated from the intersection of lines tangent to the flanks of the peaks. Other methods such as described in U.S. Pat. No. 3,976,384, which is hereby incorporated by reference herein, can also be used to measure surface angle. Such methods are known by those skilled in the art.

The reliable methods for predicting dive angle under different dive and surface angle conditions are summarized in Table 1.

TABLE 1

Recommended Method for Predicting Dive Angle under Different Surface and Dive Angle Conditions

|  | Low Dive Angle | High Dive Angle |
|---|---|---|
| Low Surface Angle | V1-V2 Peak finding | V1-V2 |
| High Surface Angle | T1 then V1-V2 Peak finding | T1 then V1-V2 |

Figure 13:
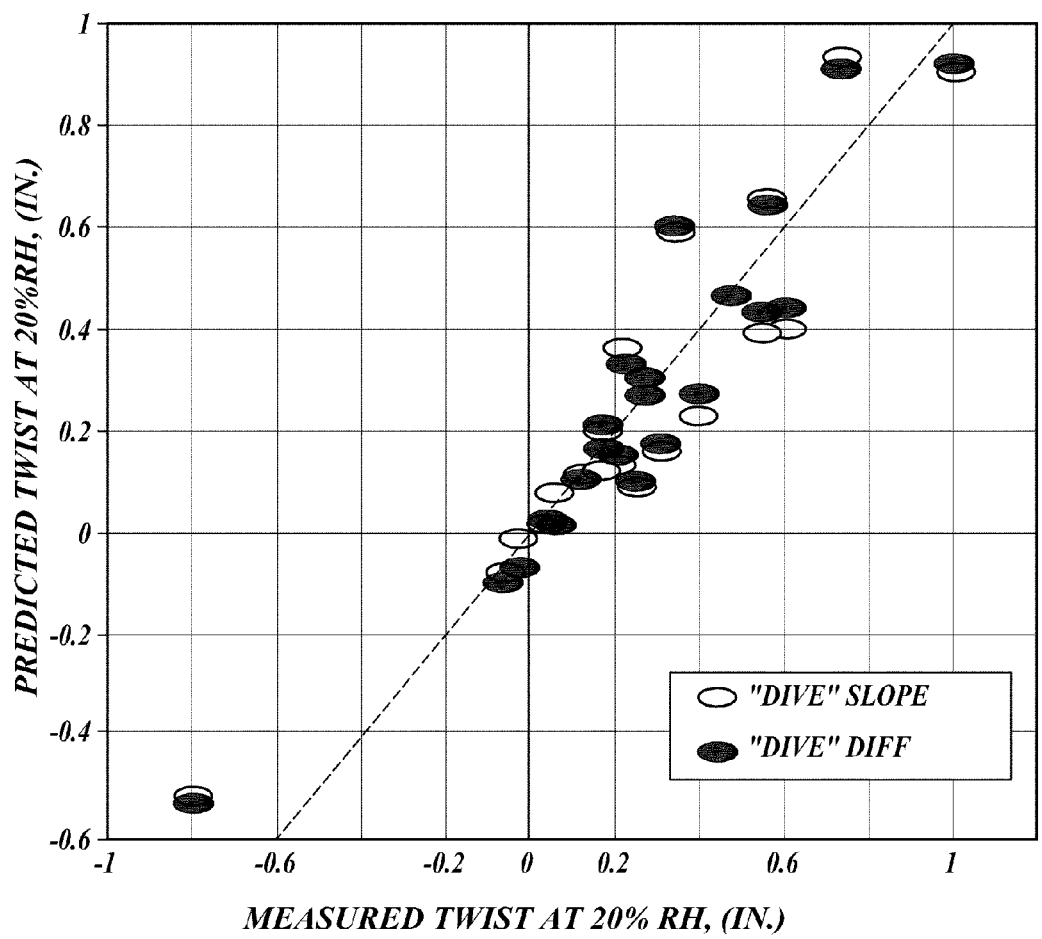
FIG. 13 is a plot of the results of twist predictions using V1-V2 calculated from the T2 scanning system (The open and filled symbols are the results using the slope and differences of dive angles across the board respectively and both results are similar to that in FIG. 7)

As shown in FIG. 13, using the formula V1-V2 to calculate dive angles as the input to the twist model produced similar prediction of lumber twist. Based on these results, two single sensors, or two groups of sensors placed at the 0° and 180° positions along the lumber axis, can be used to estimate dive angles for twist prediction. To further improve accuracy, an estimate of the surface grain angle can be derived from the diffuse (T1) "tracheid effect" pattern generated by the same laser used for the T2 measurement.

Figure 14:
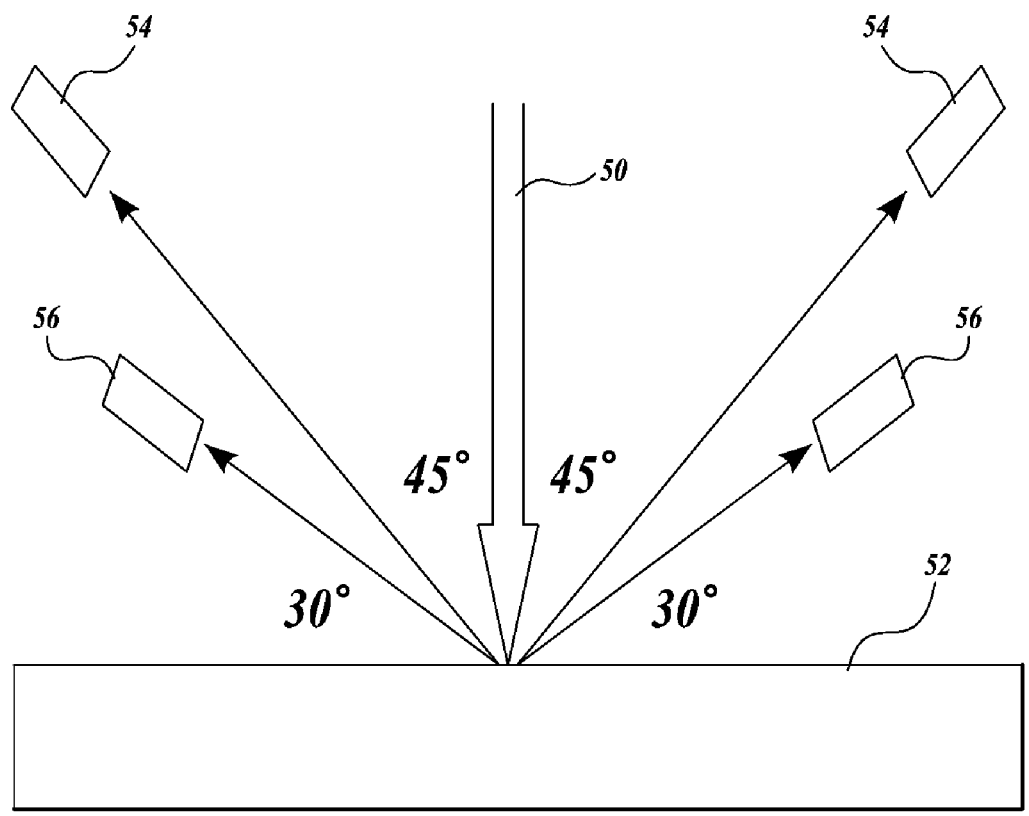
FIG. 14 is a diagram of positioning sensor pairs at more than one detection angle to derive a gradient of dive angle around a knot.

If only one pair of sensors with 45° view angle is used, the maximum dive angle prediction is half the view angle (22.5°). As the dive angle increases beyond the half angle, the reflection intensity at the valley decreases. As shown in FIG. 14, when laser light (50) is reflected off the surface of wood (52), multiple pair of sensors (54, 56) can be positioned at different view angles (for example, 30° and 45°) to extend the range and improve the accuracy of dive angle measurement.

2. Peak Height Differences and Ring Curvature

Its varied knot structure makes grading SYP (Southern Yellow Pine) lumber a challenge. Pith-containing and non-pith-containing lumber are well known to have contrasting wood properties. The ability to identify the location of pith will further improve knot volume assessment and strength grading of SYP and other species. Ring curvature or the radius to pith also helps twist prediction, which is important for warp grading.

The approximate location of pith relative to the surface of lumber can be derived by comparing knot count, knot size and the grain swirling pattern around a knot between the sides and between the edges of a piece of lumber (see U.S. Pat. No. 4,916,629). Such method is applicable only when there are knots on opposite sides of the lumber. A more useful method would allow similar information to be obtained using the clearwood area, which normally occupies most areas on lumber surfaces.

Figure 15A:
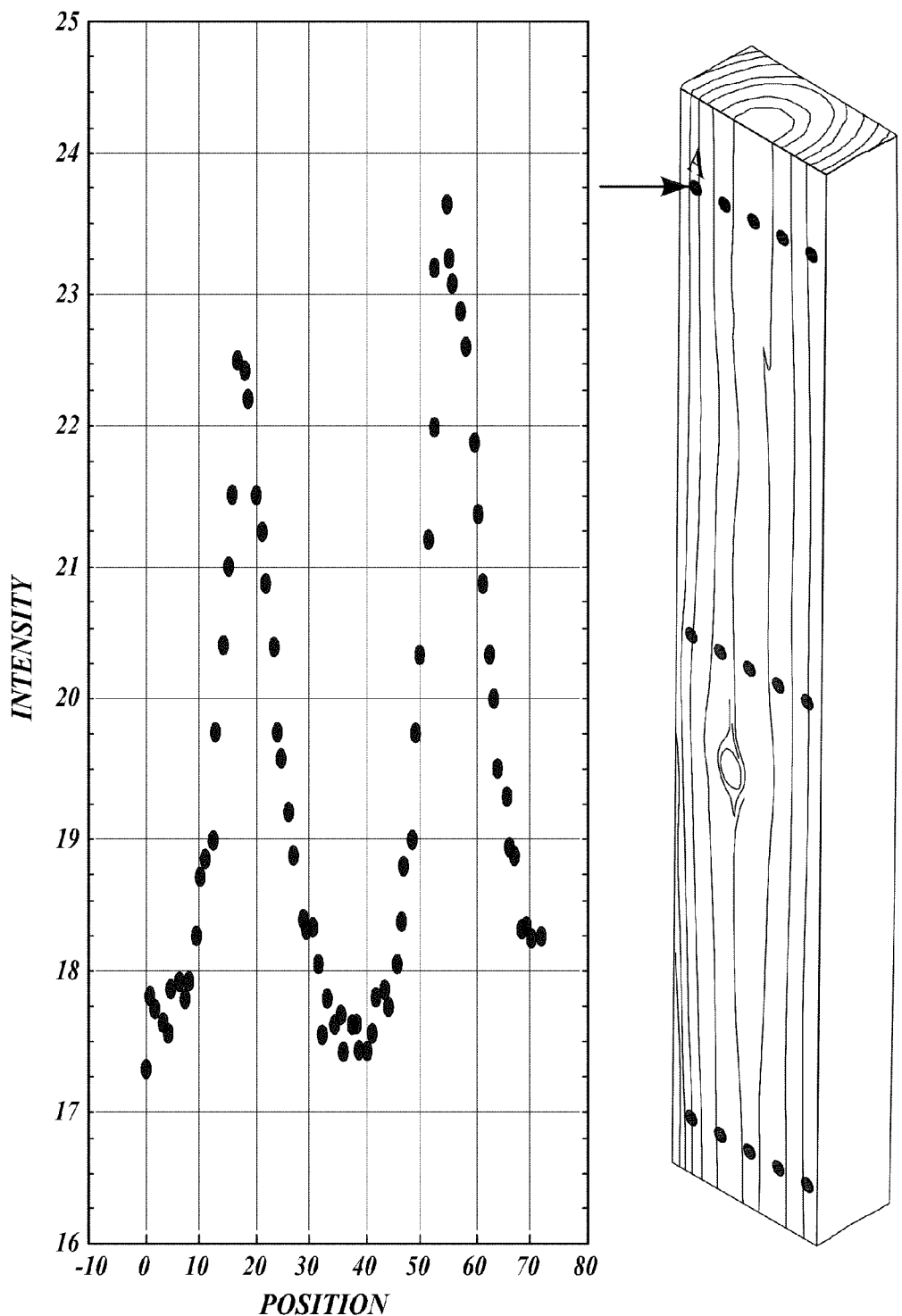
FIGS. 15A-O illustrates plots of reflected light intensity traces of 15 areas on a 16 inch long segment of a 2 inch by 4 inch board, wherein the measurements were taken from left to right across the board at different regions of ring curvature at three different locations along the longitudinal axis of the board.
Figure 15B:
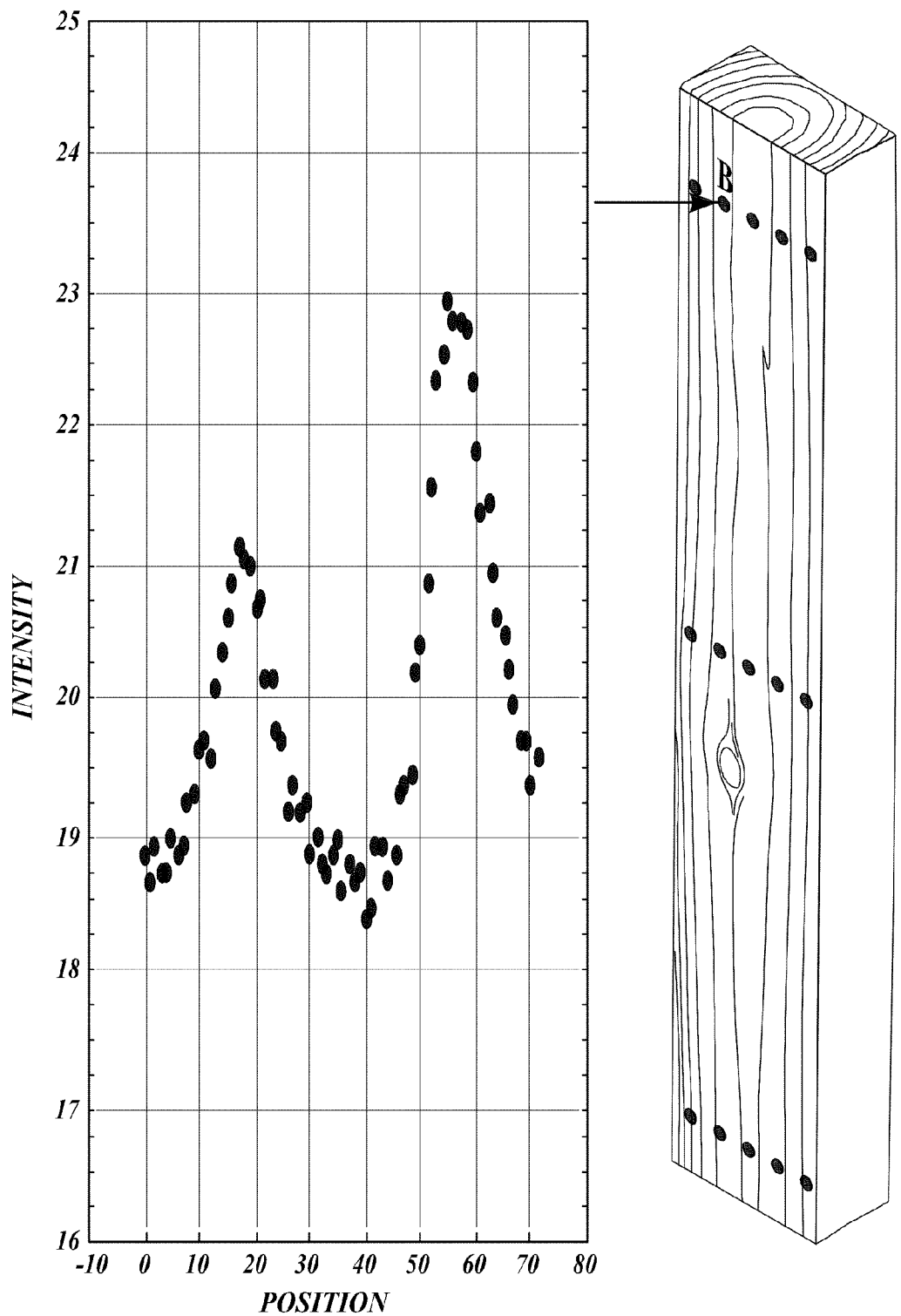
Figure 15C:
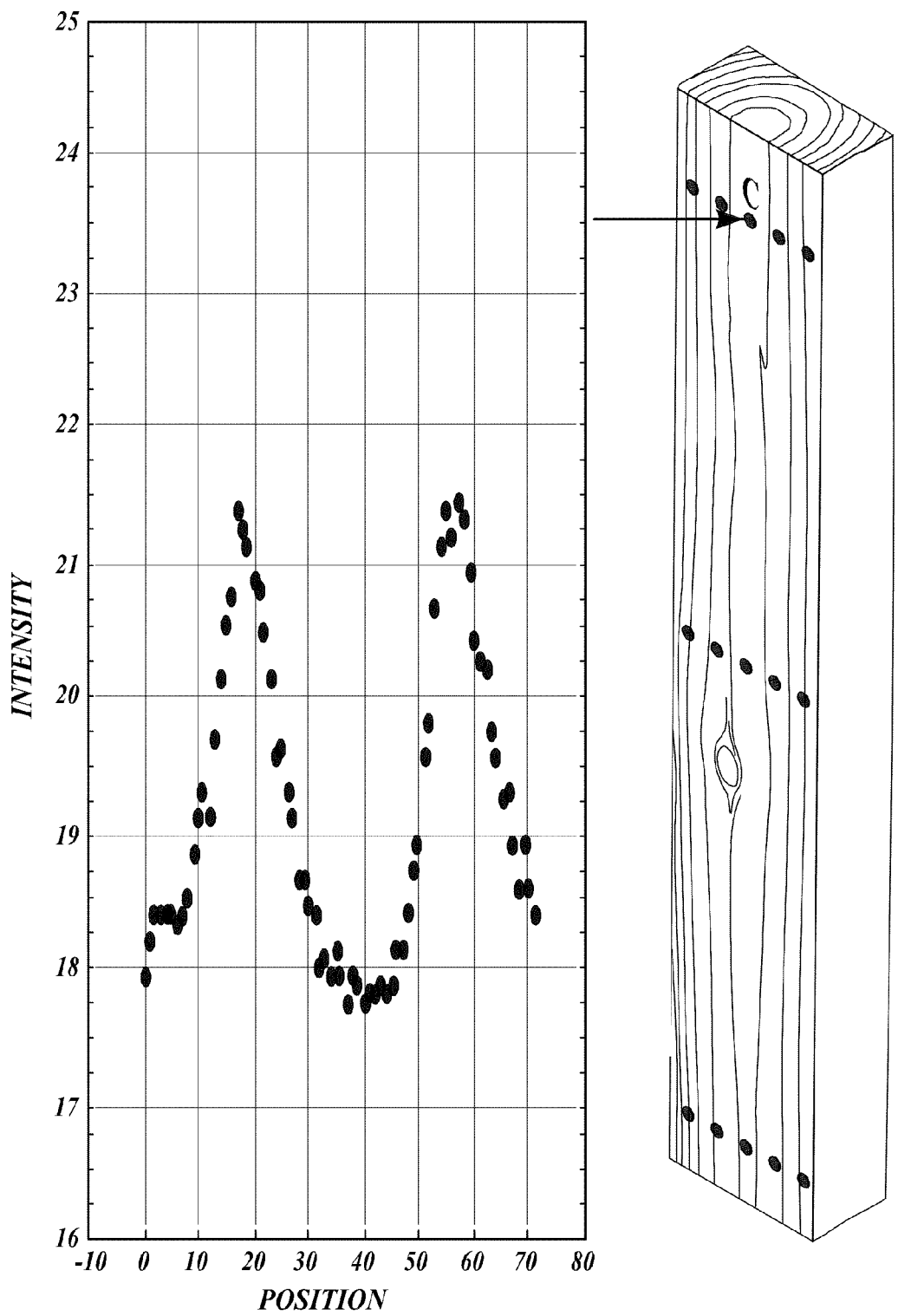
Figure 15D:
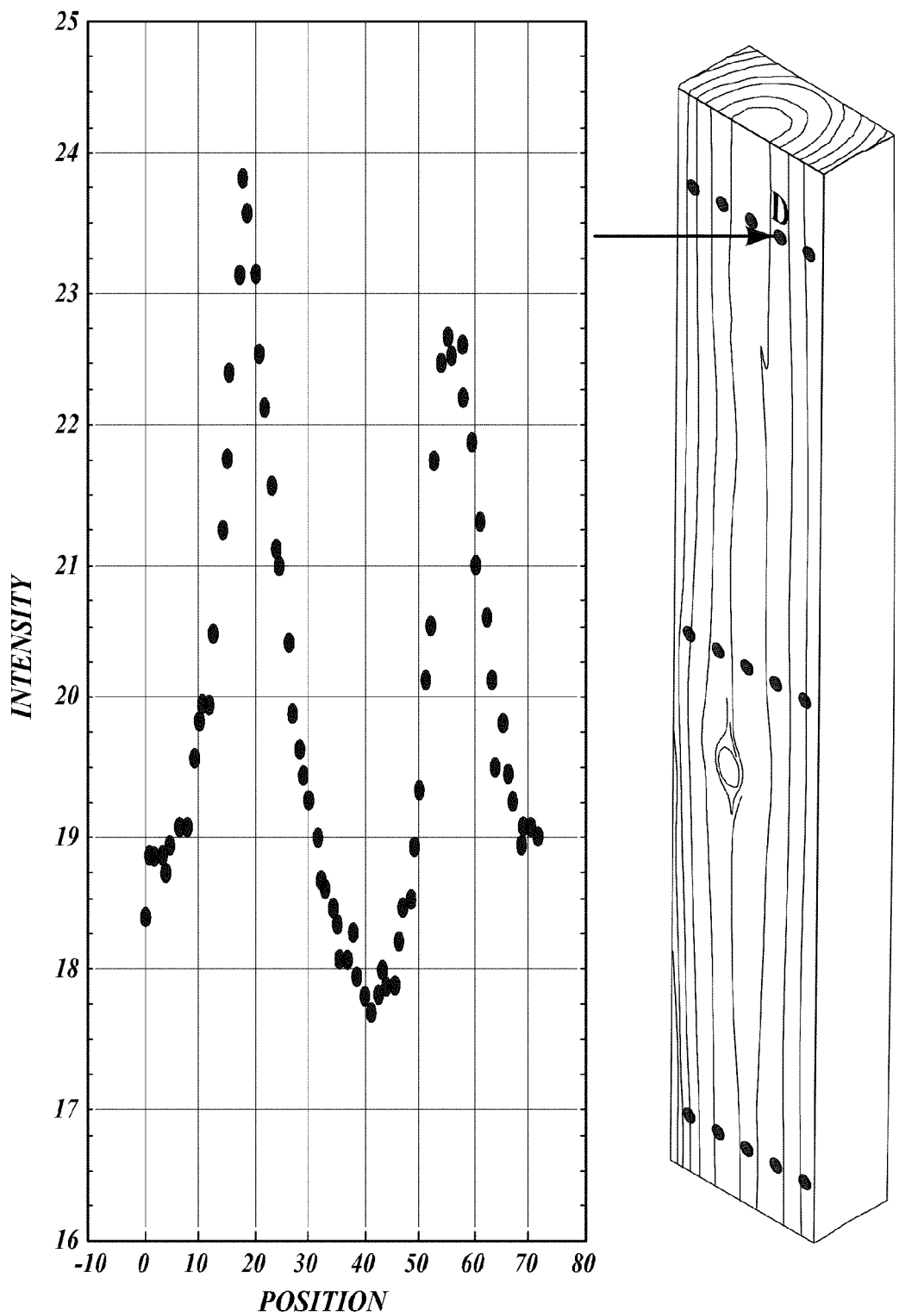
Figure 15E:
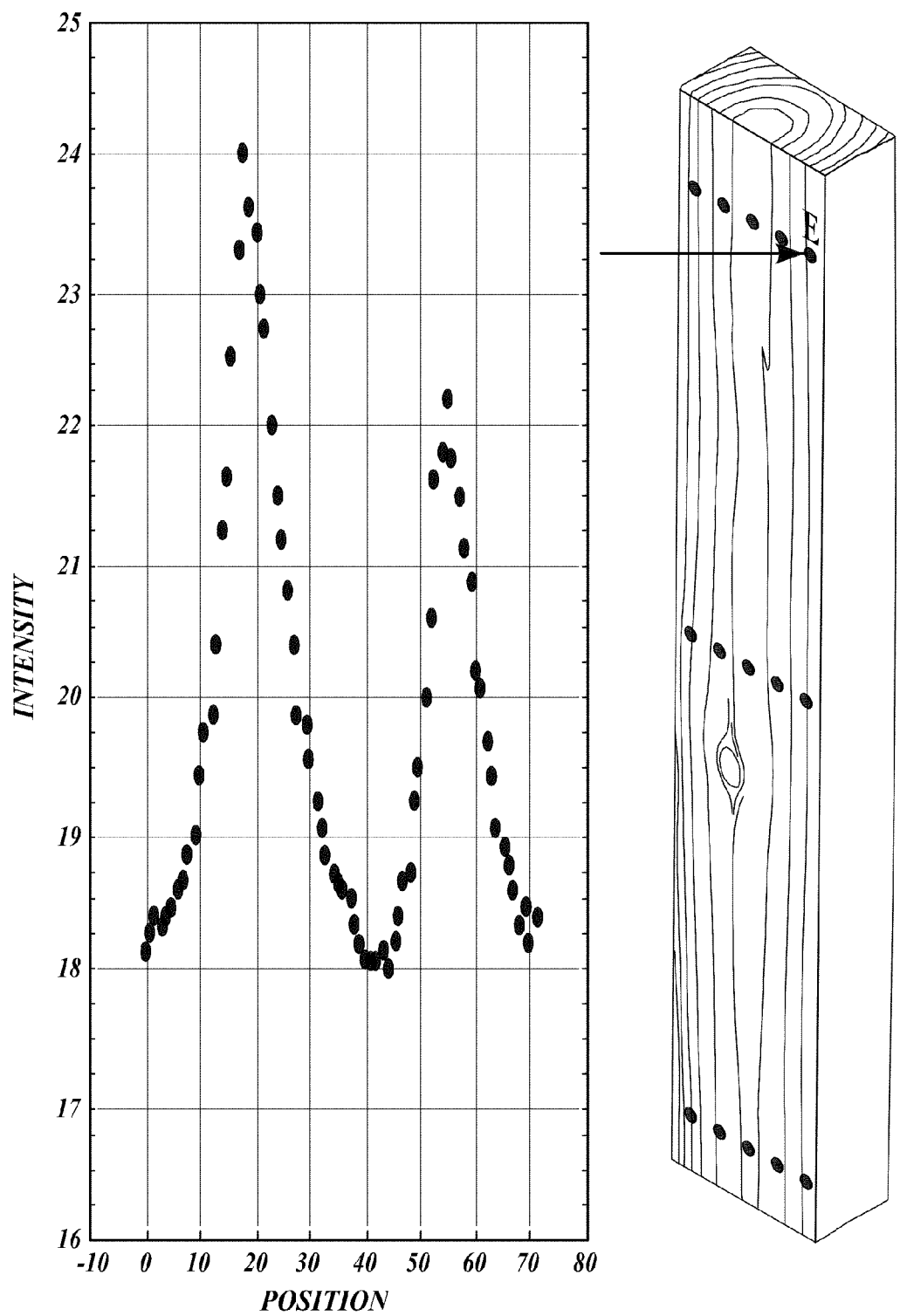
Figure 15F:
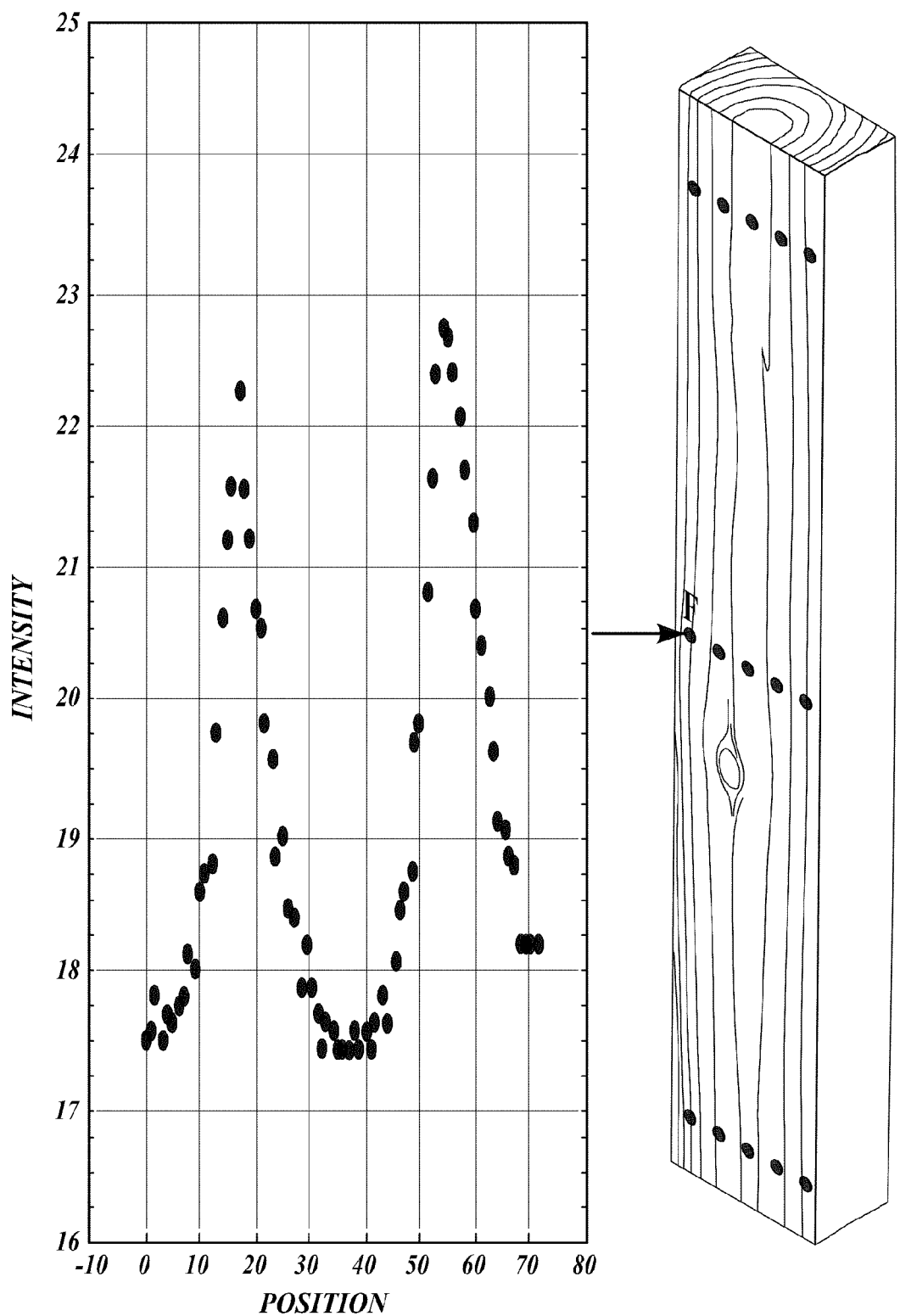
Figure 15G:
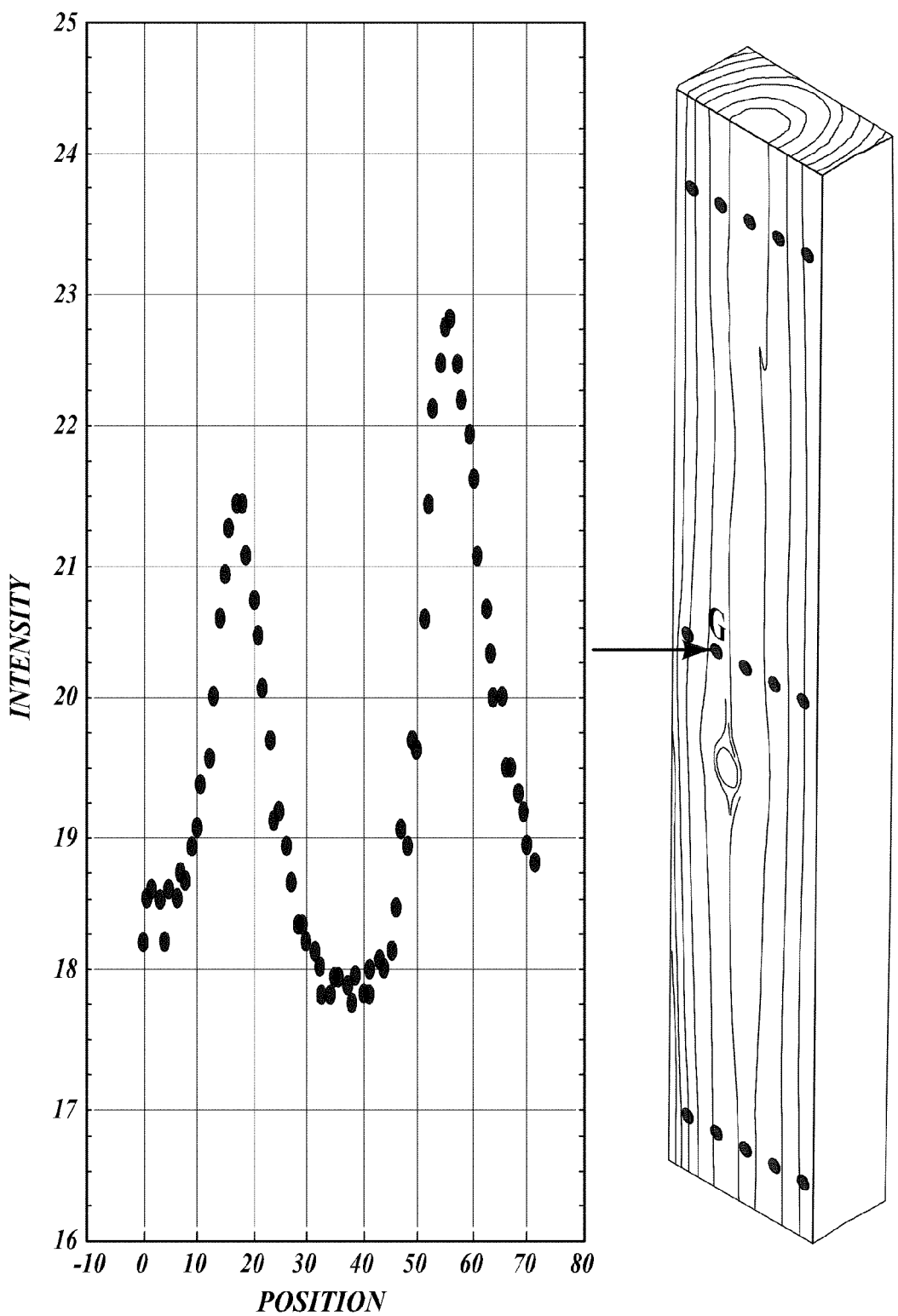
Figure 15H:
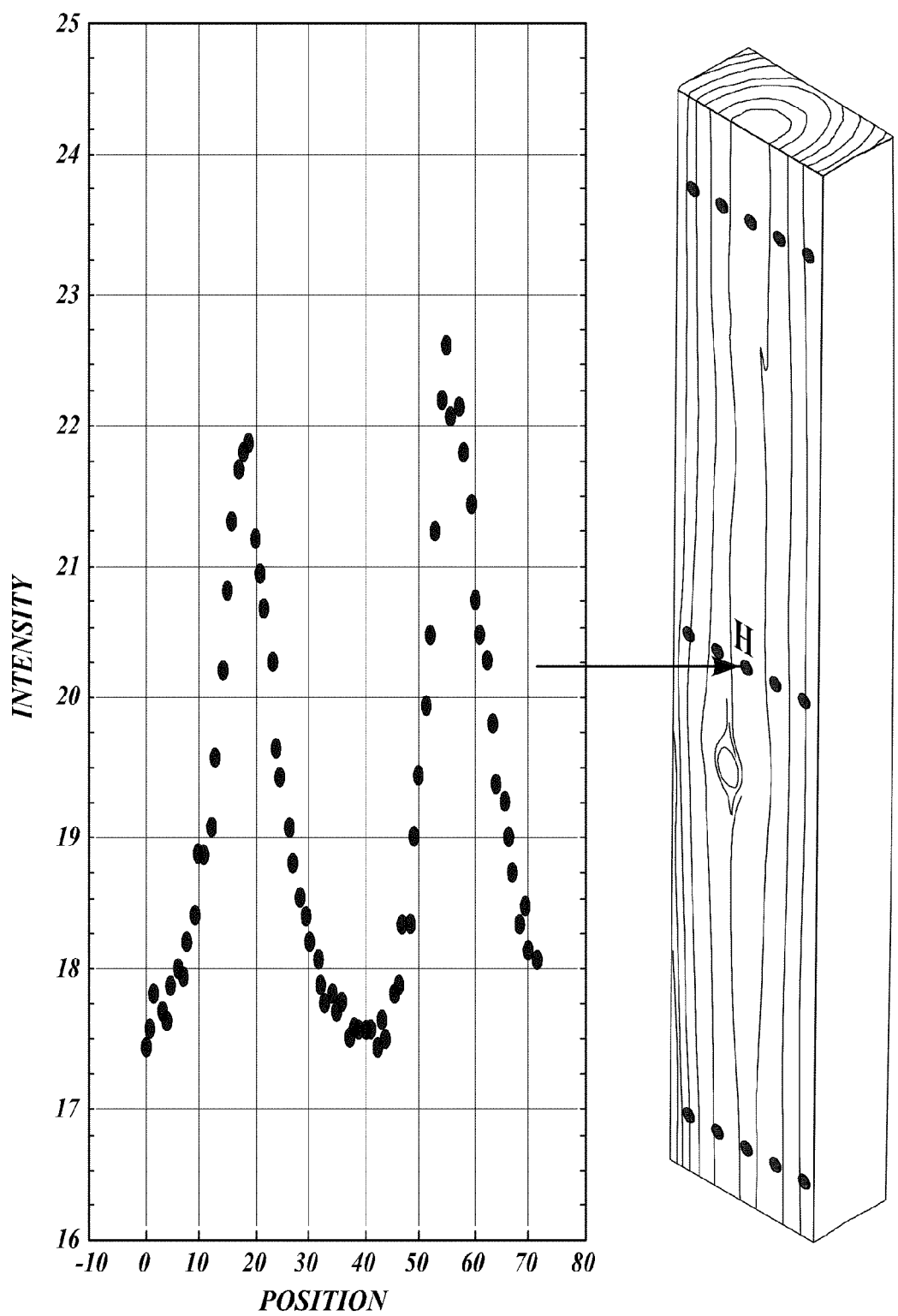
Figure 15I:
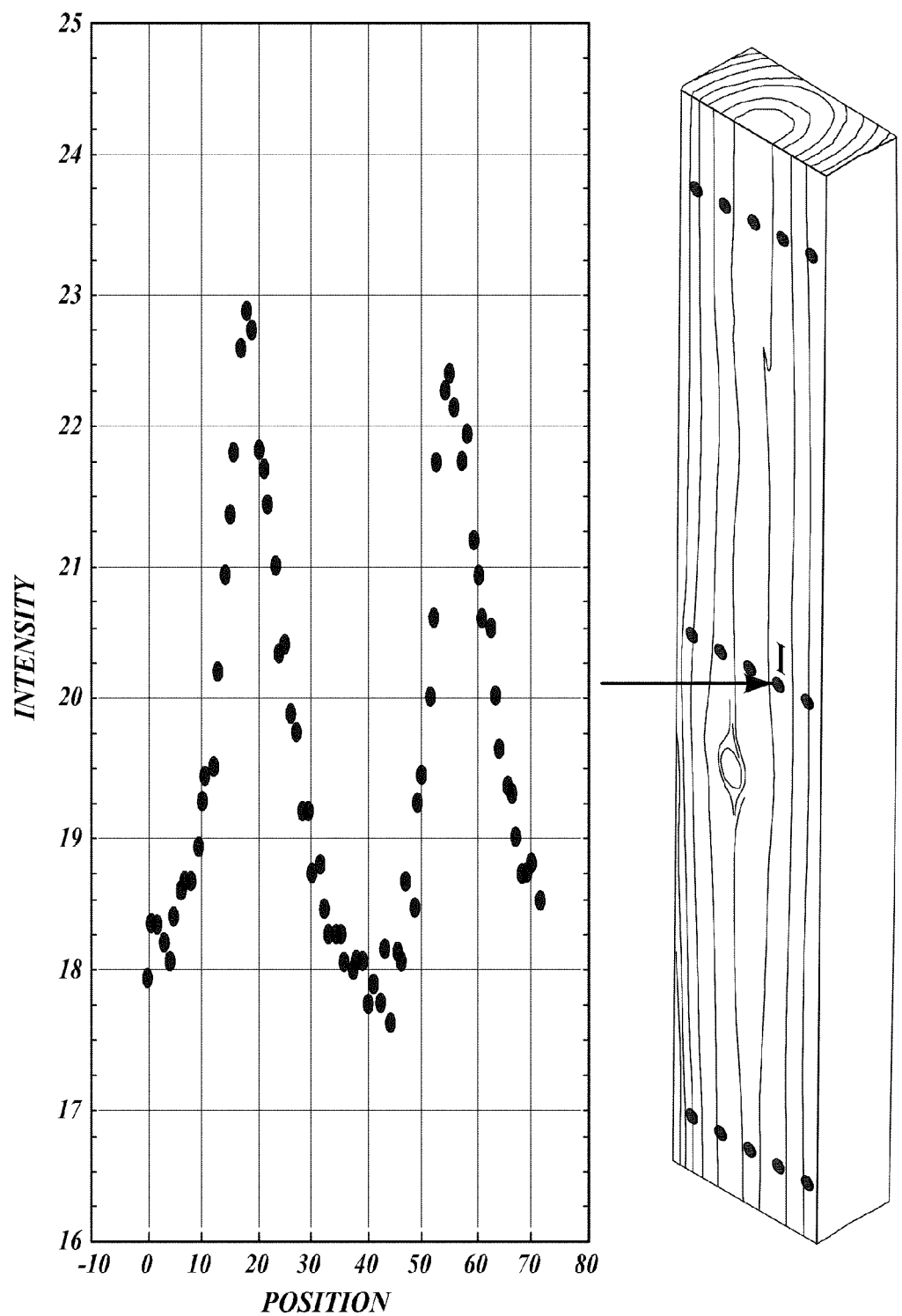
Figure 15J:
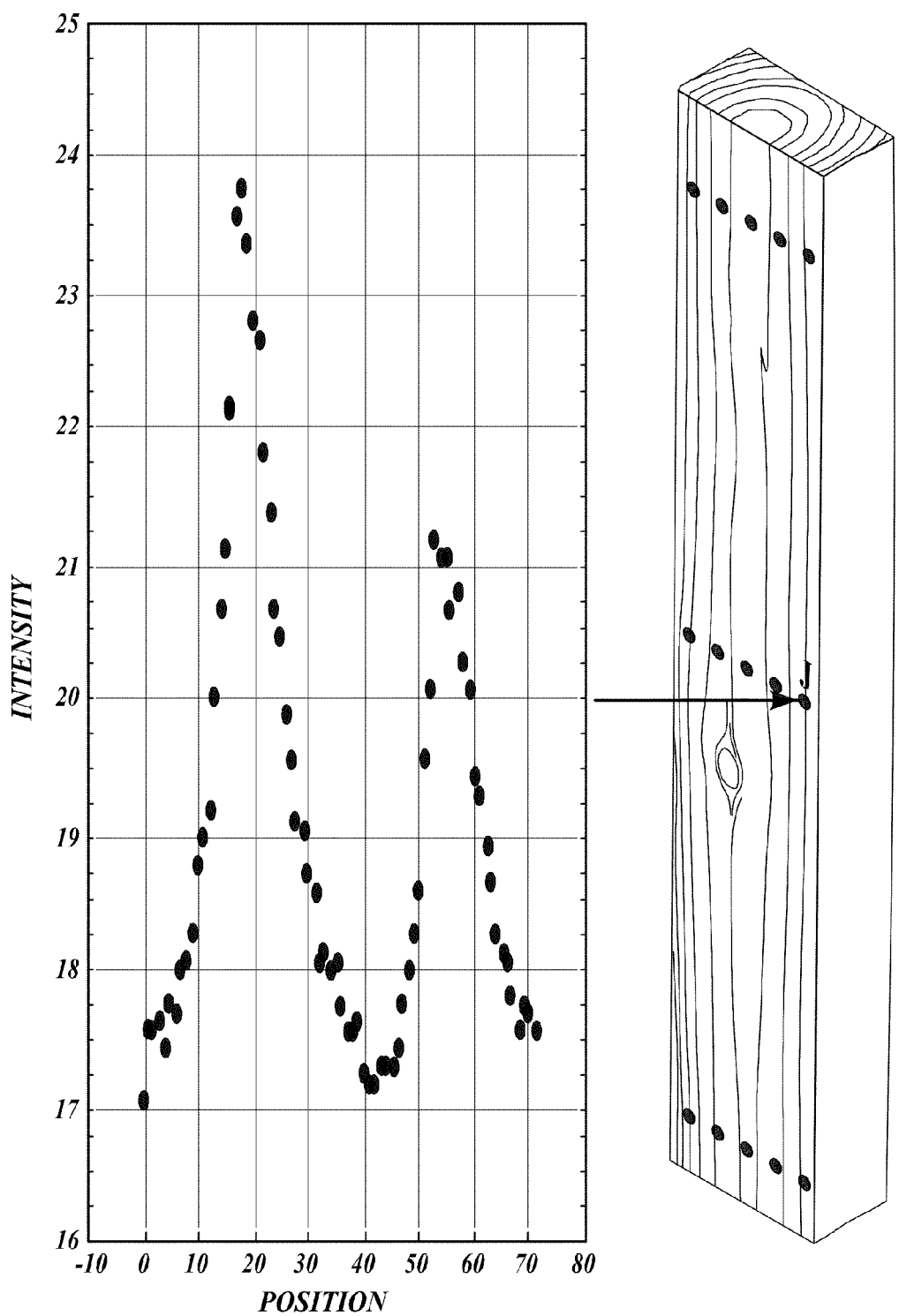
Figure 15K:
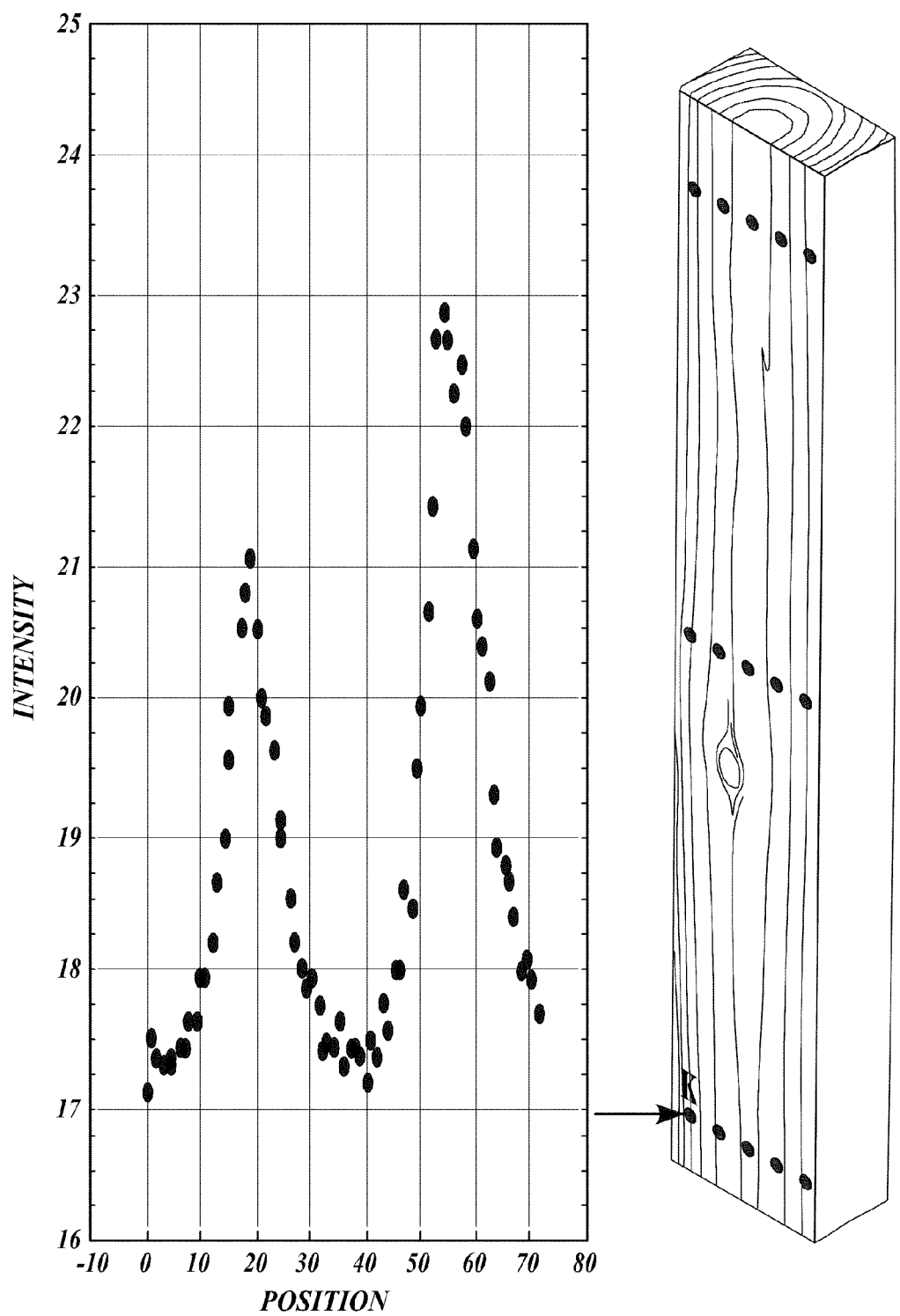
Figure 15L:
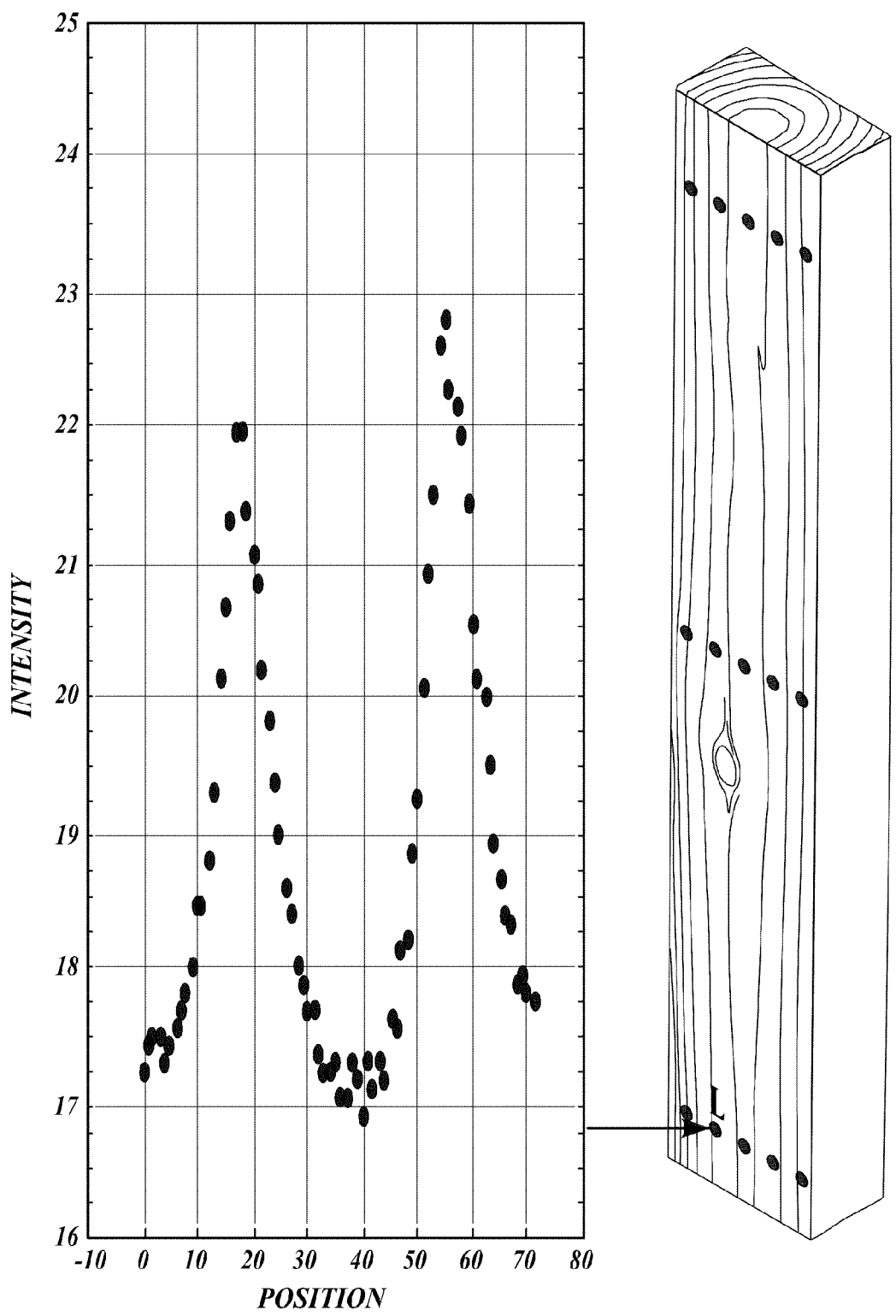
Figure 15M:
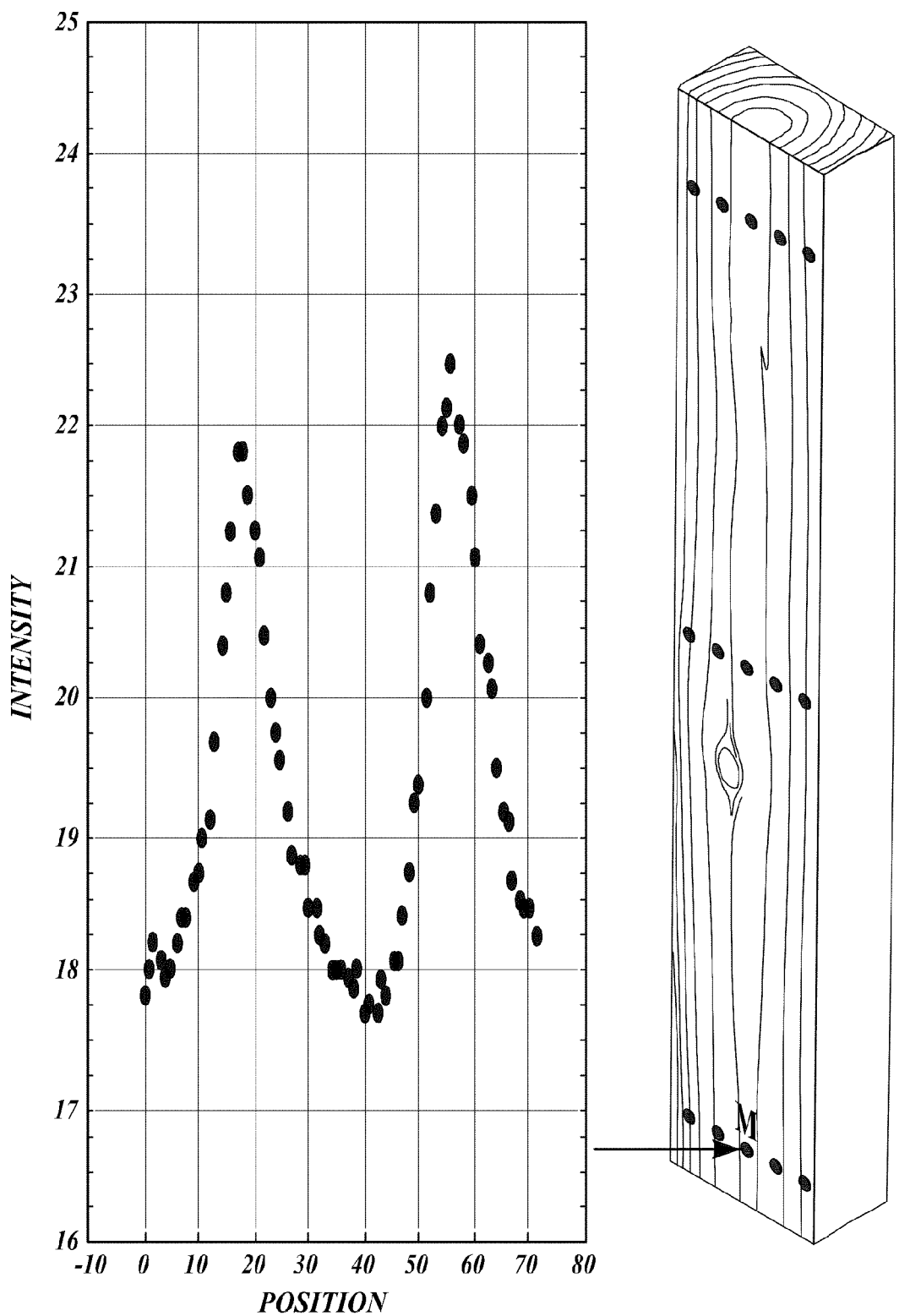
Figure 15N:
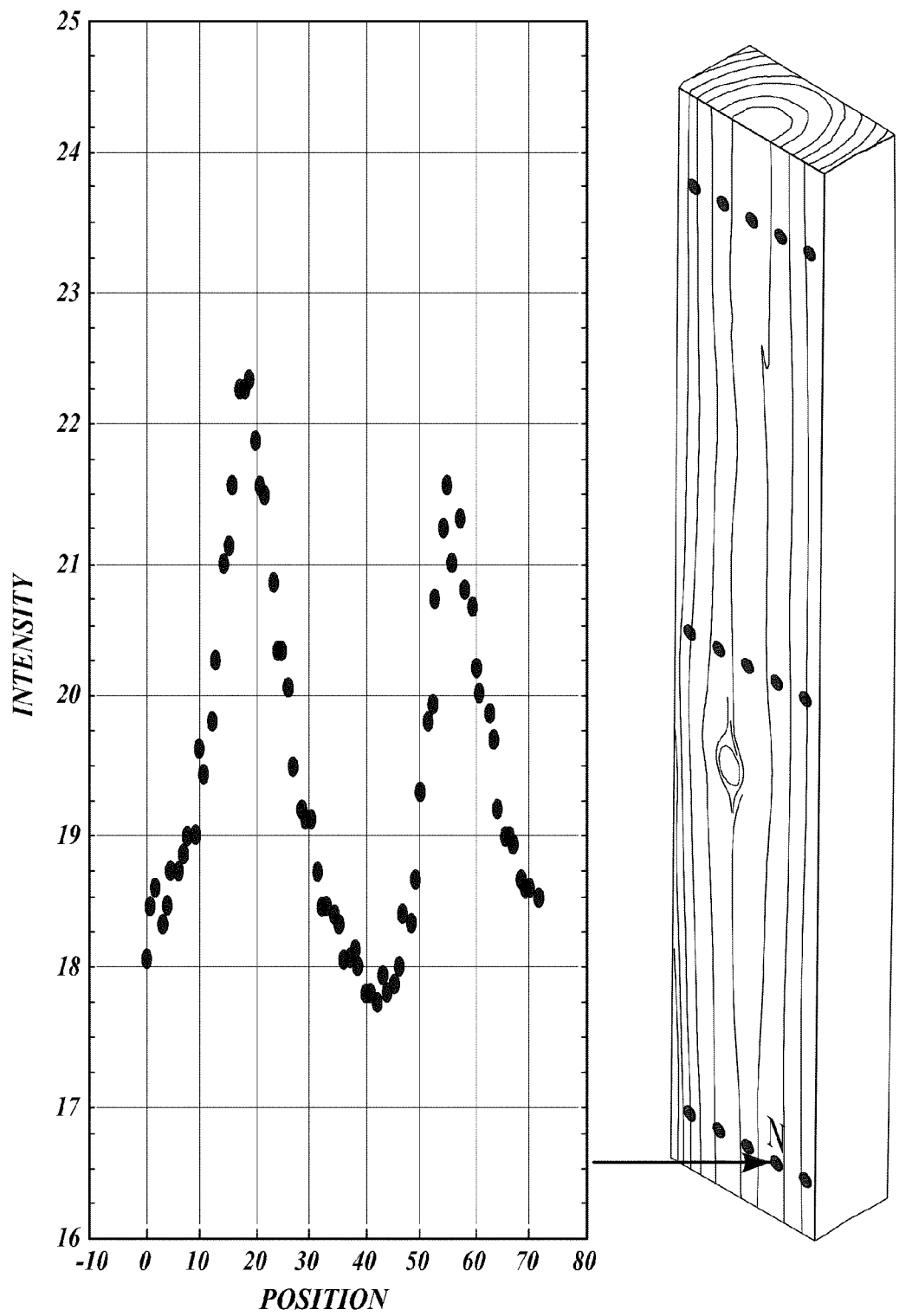
Figure 15O:
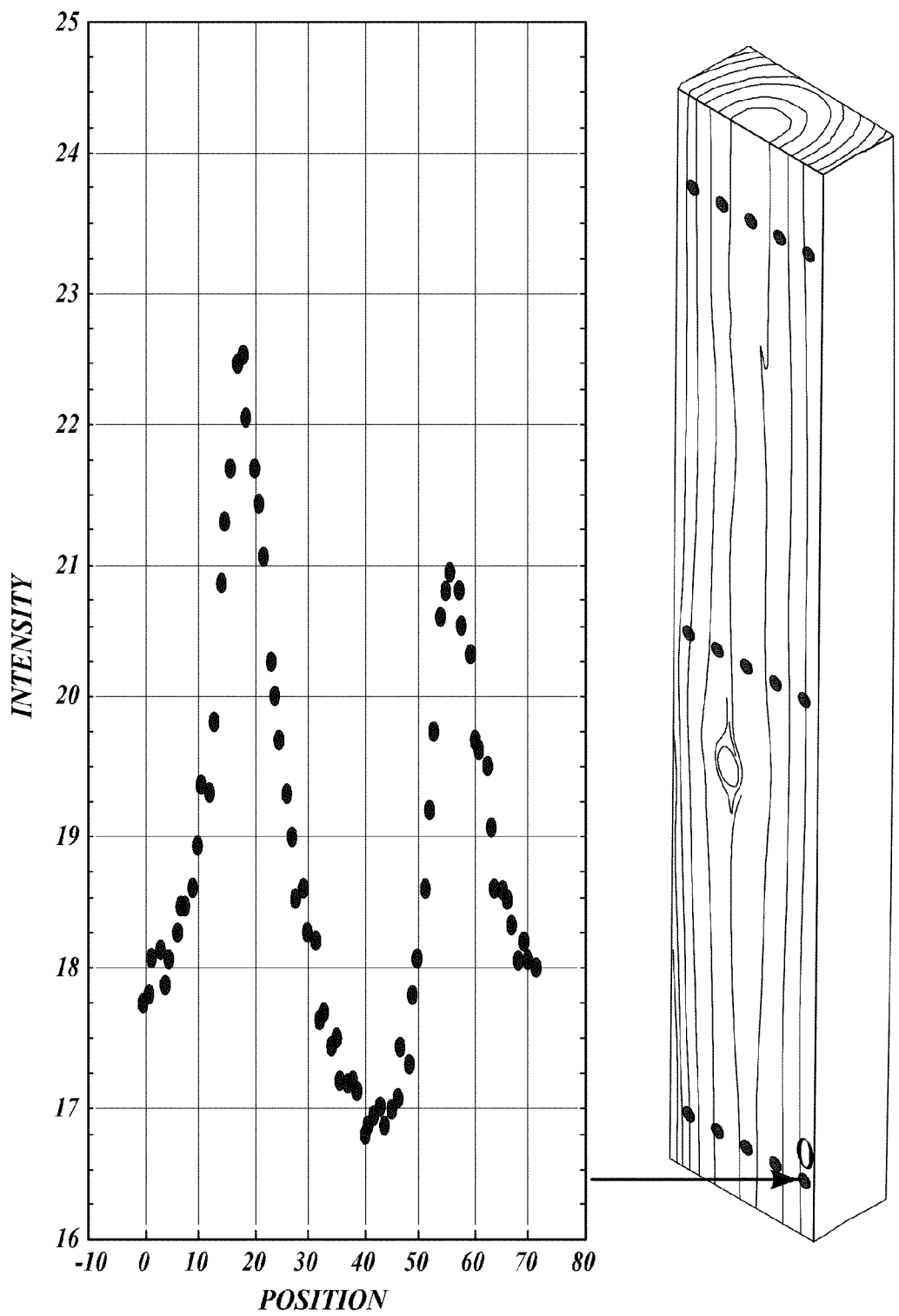

An interesting observation on the 16" sample is the systematic pattern between the peak height difference and the ring curvature (see FIGS. 15A-15O). Note that variation of peak heights tends to follow the ring curvature. The results suggest that information from peak differences can be used to predict ring curvature.

Figure 16:
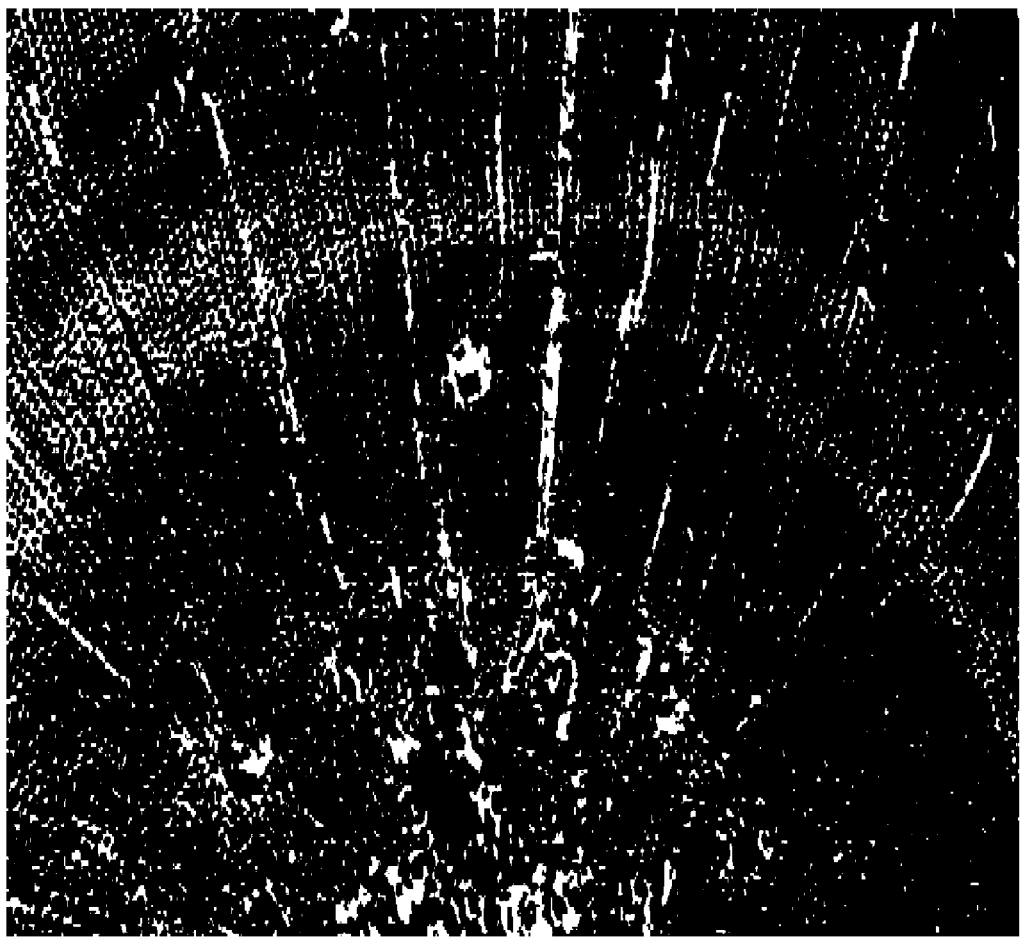
FIG. 16 is a SEM photograph of the cross-section of loblolly pine seedling showing the alignment of tracheids in a radial direction.
Figure 17:
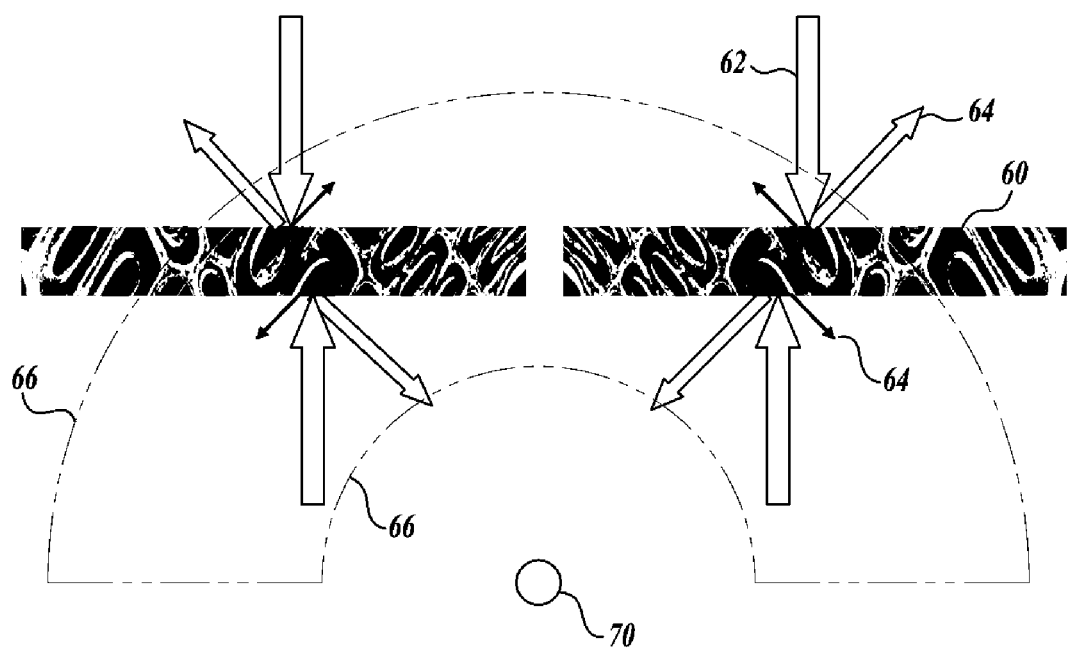
FIG. 17 is a diagram showing the asymmetric reflection patterns due to an exposed lumen that is lop-sided.

The direction of the tangential wall exposed on a lumber surface fluctuates according to the angle of the file of tracheids relative to lumber surface (FIG. 16). FIG. 17 illustrates that laser light (62) striking the exposed lumen of tracheids (60) on the lumber surface having asymmetric side walls and different angles of bottom walls will reflect different amounts of light (64) to the sensors (the location of the annual rings (66) and pith (70) are indicated schematically).

Figure 18:
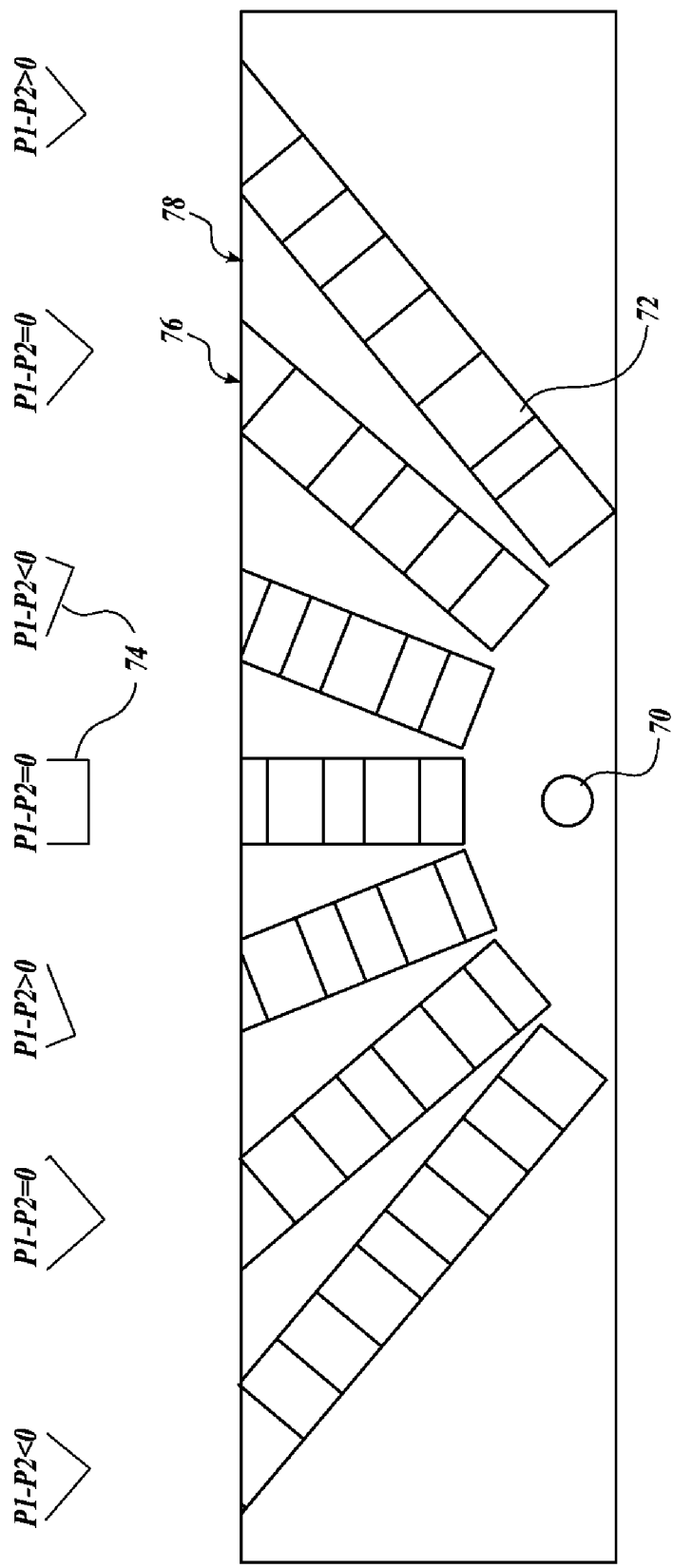
FIG. 18 is a diagram of a staple model for curvature (The staple represents the cross-section of the walls of the tracheid on the surface. A laser is at the top side of the photo, and P1 and P2 are the intensities of the sideway reflections detected at the sensor positioned at the right side and the left side of the photo, respectively)
Figure 19:
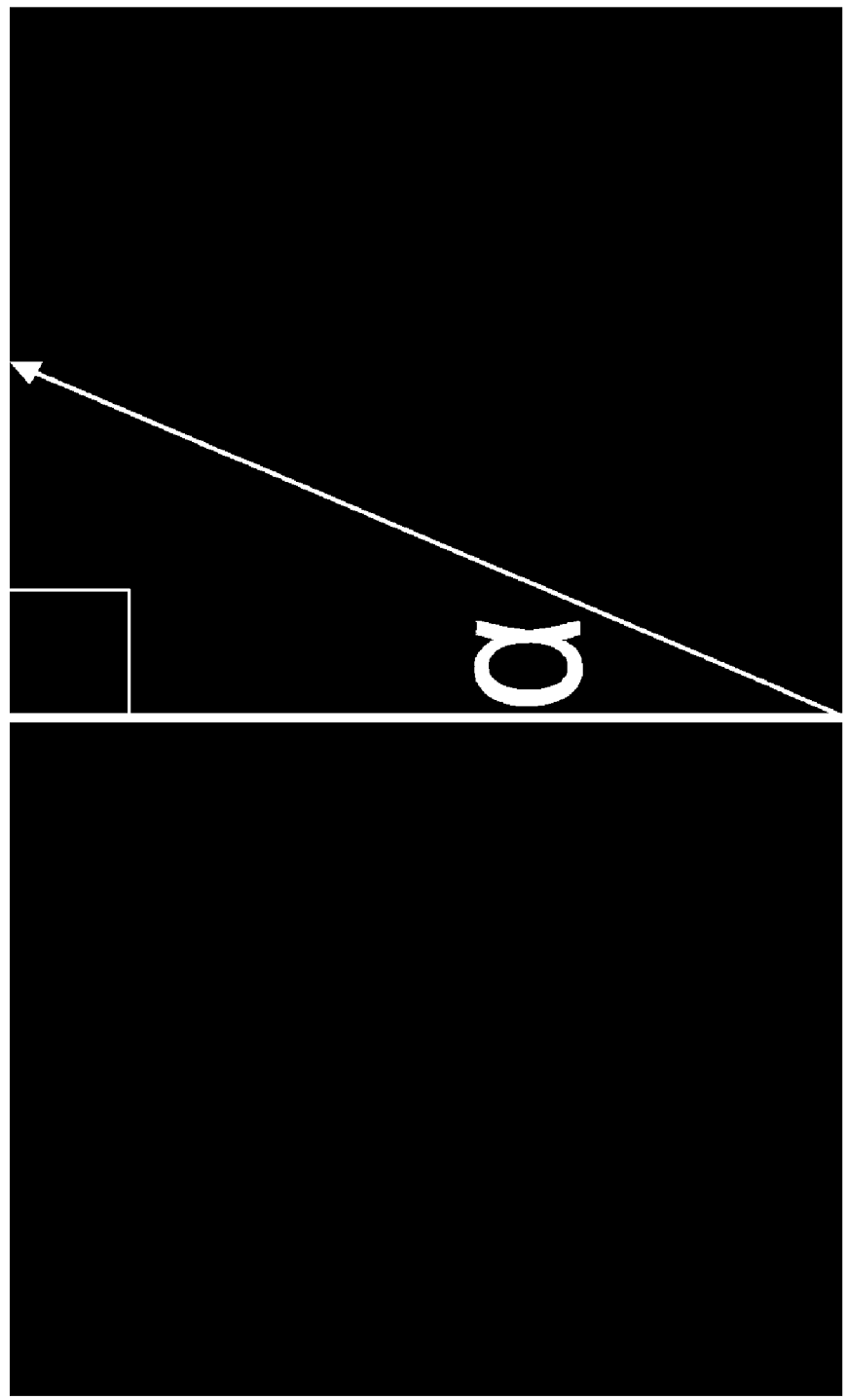
FIG. 19 is a photograph of the end of a 2 inch by 4 inch board ("2×4") showing the angle $\alpha$ is the direction of the file of tracheids with respect to the edge of the lumber.

Typically, the cross-section of a softwood tracheid has 4-6 corners and the same number of side walls. As shown in FIG. 18, the overall shape of the tracheid (72) cross-section approximates a square or a rectangle. The systematic P1-P2 patterns across a board can be explained by the "staple model", in which the staple (74) represents the cross-section of an opened tracheid (76) (left and right side walls and bottom wall which is tangent to the ring curvature) on the surface (78) of a piece of lumber. In the staple model, the top wall or one side wall of the rectangular has been removed (see FIG. 18). For discussion purposes, a point on the surface of lumber is connected with the pith center FIG. 19). That line will be inclined at an angle $\alpha$ from perpendicular. Assuming the cross-section of the tracheid is square, then P1-P2=0 when $\alpha$=0°, 45°, and 90°. Using the previously described Plessey T2 sensor composed of a ring of 72 detectors, the maximum absolute value of P1-P2 is observed at an angle $\alpha$=22.5°, at which angle the intensity of the reflection from one side wall is minimized due to the 45° view angle.

Figure 20A:
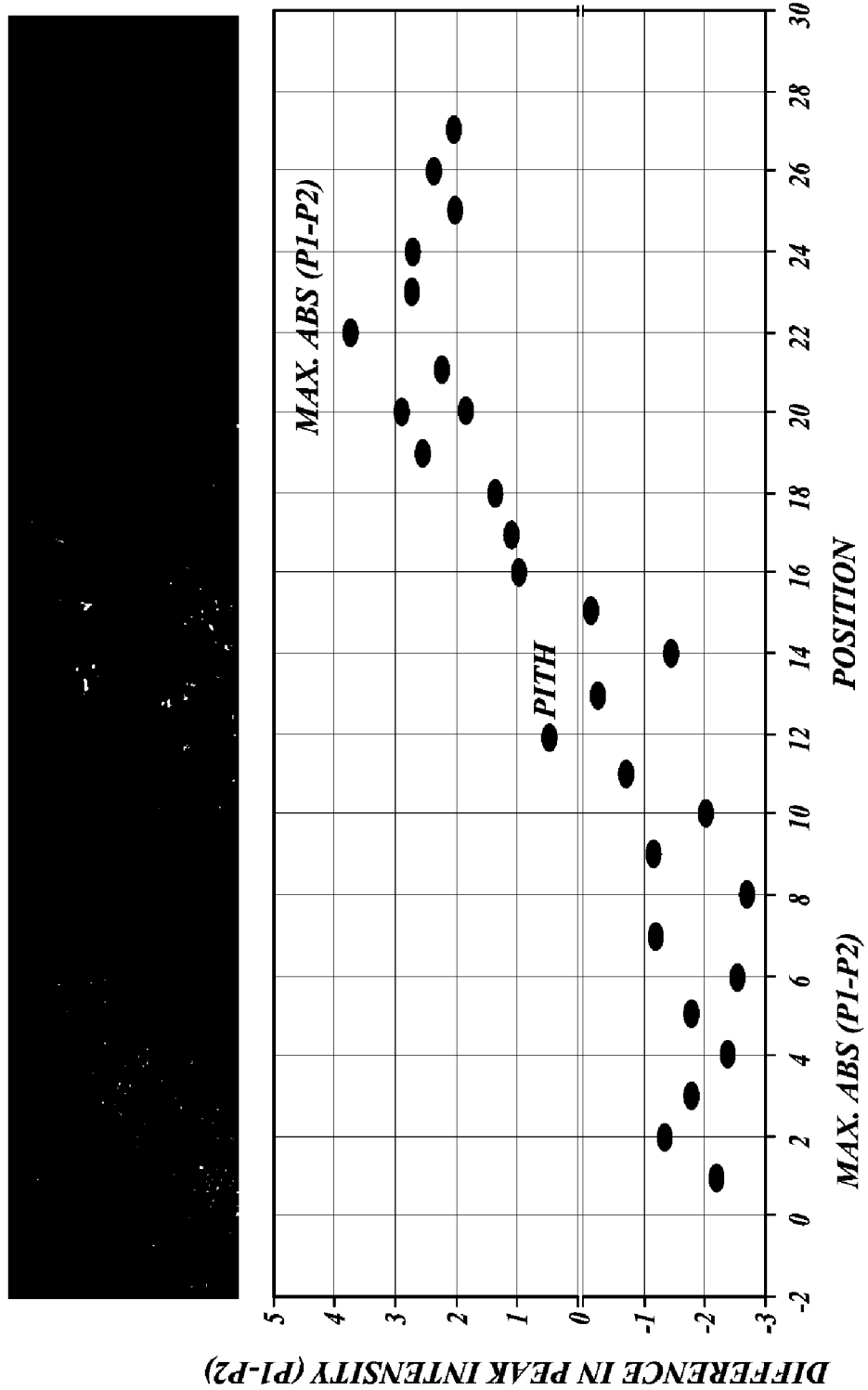
FIGS. 20A-B illustrates P1-P2 values on the top side of a curve down (top) and up (bottom) wood sample (The x-axis is the distance in ¼" units. Note that the measurements were not taken from the SEM pictures, which were cross-sections of the stem of a loblolly pine seedling.)

The sign and the slope of the change in the P1-P2 values near the surface location where $\alpha$=0 are related to the sign and magnitude of ring curvature at that location (see FIG. 20).

Figure 20B:
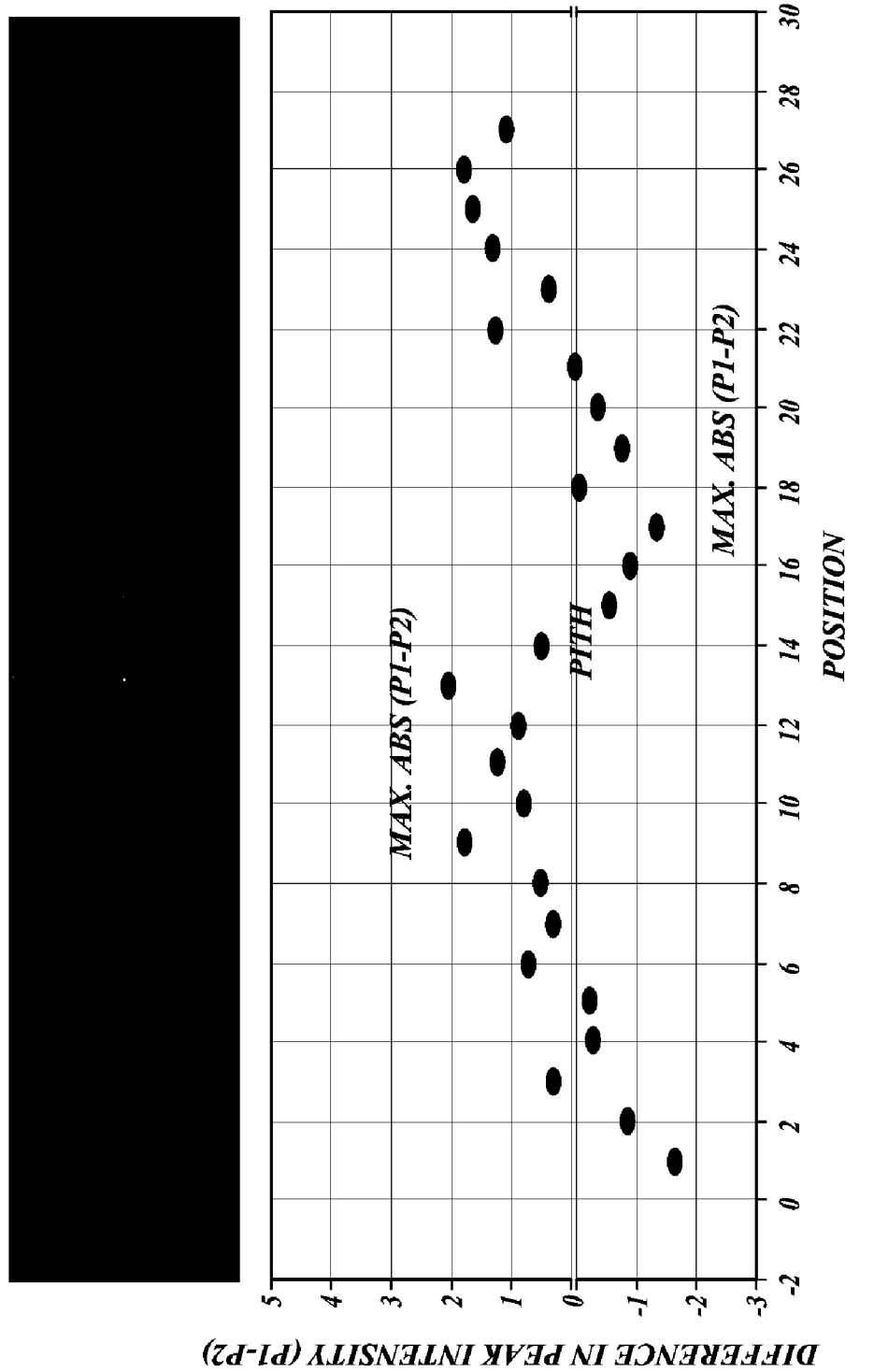

If the cross-section of the tracheids is not square or the view angle is different from 45°, the value of $\alpha$ at these locations of maximum abs (P1-P2) will vary. This difference can be estimated mathematically or empirically. The relationship between the radius and the slope of the P1-P2 profile across the neighboring locations can be established empirically. The steeper the slope of the P1-P2 profile, the shorter the radius. The surface represented by the profile in FIG. 20B is closer to the pith than the surface represented by the profile in FIG. 20A. Consequently, the slope of P1-P2 profile near $\alpha$=0 (location that is normal to the projected pith) of the top profile is gentle and that of the bottom profile is steep. Using this empirical relationship, the distance to the pith can be estimated based on the slope of the P1-P2 profile across the board.

Curve smoothing may be utilized to provide more accurate results. Normally, the orientation of the concavity on the surface of a piece of lumber is inverted on the opposite side. Therefore the sign of the slope of the P1-P2 pattern is reversed between opposite faces at their $\alpha$=0 locations.

Figure 21:
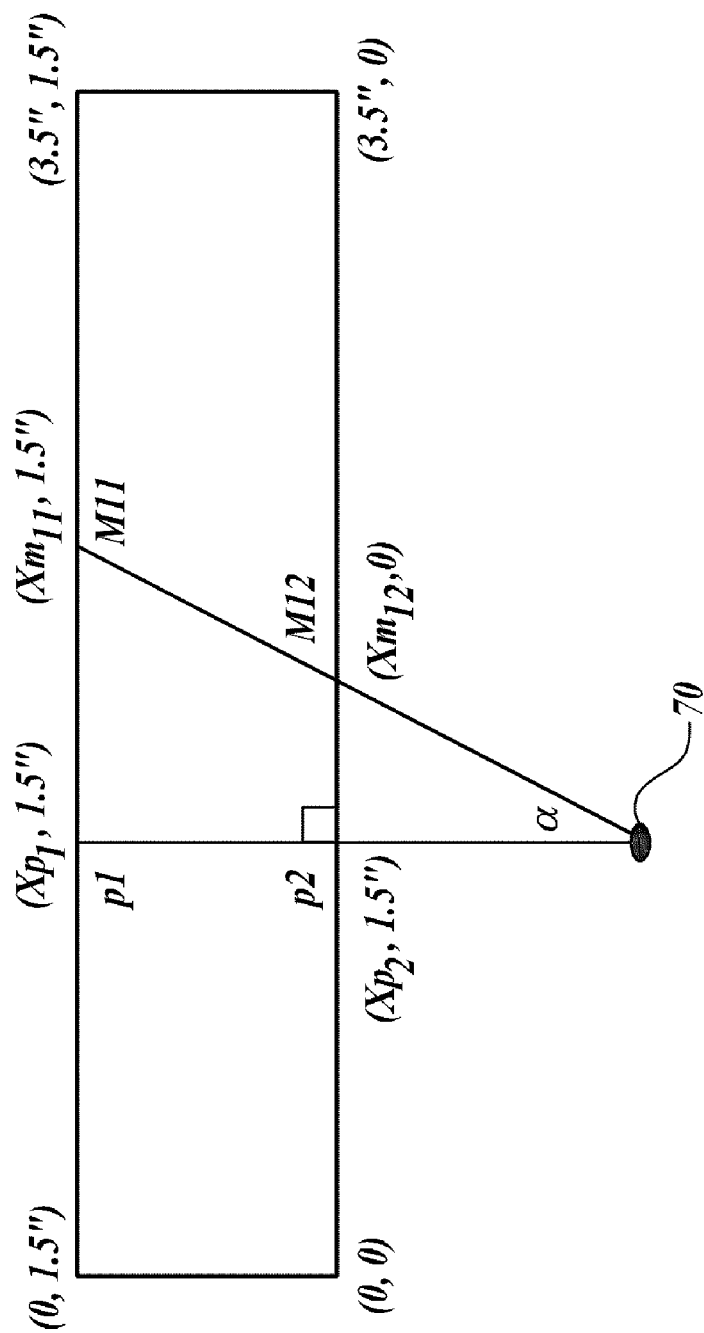
FIG. 21 is a diagram of the pith at the interception of lines p1-p2 and M11-M12 ($\alpha$=22.5° for 45° sensor angle)
Figure 22:
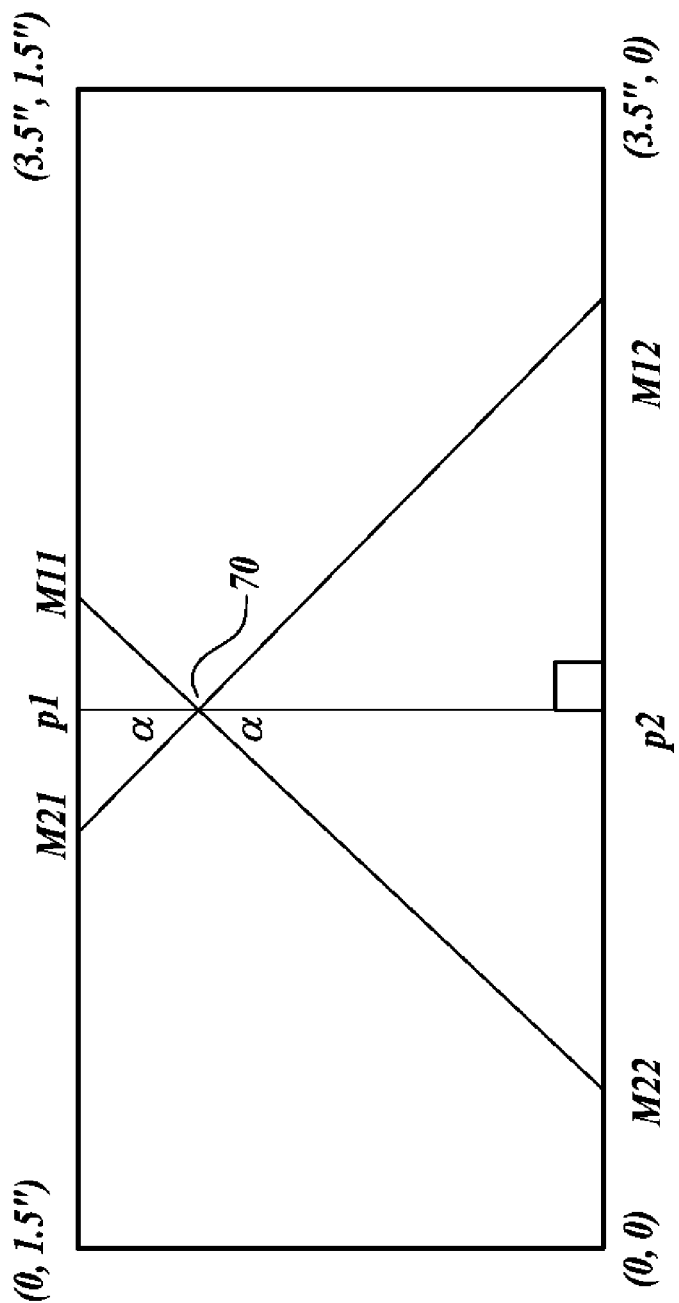
FIG. 22 is a diagram of the pith at the interception of lines p1-p2 and M11-M22 or M21-M12 ($\alpha$=22.5° for 45° sensor angle)
Figure 23A:
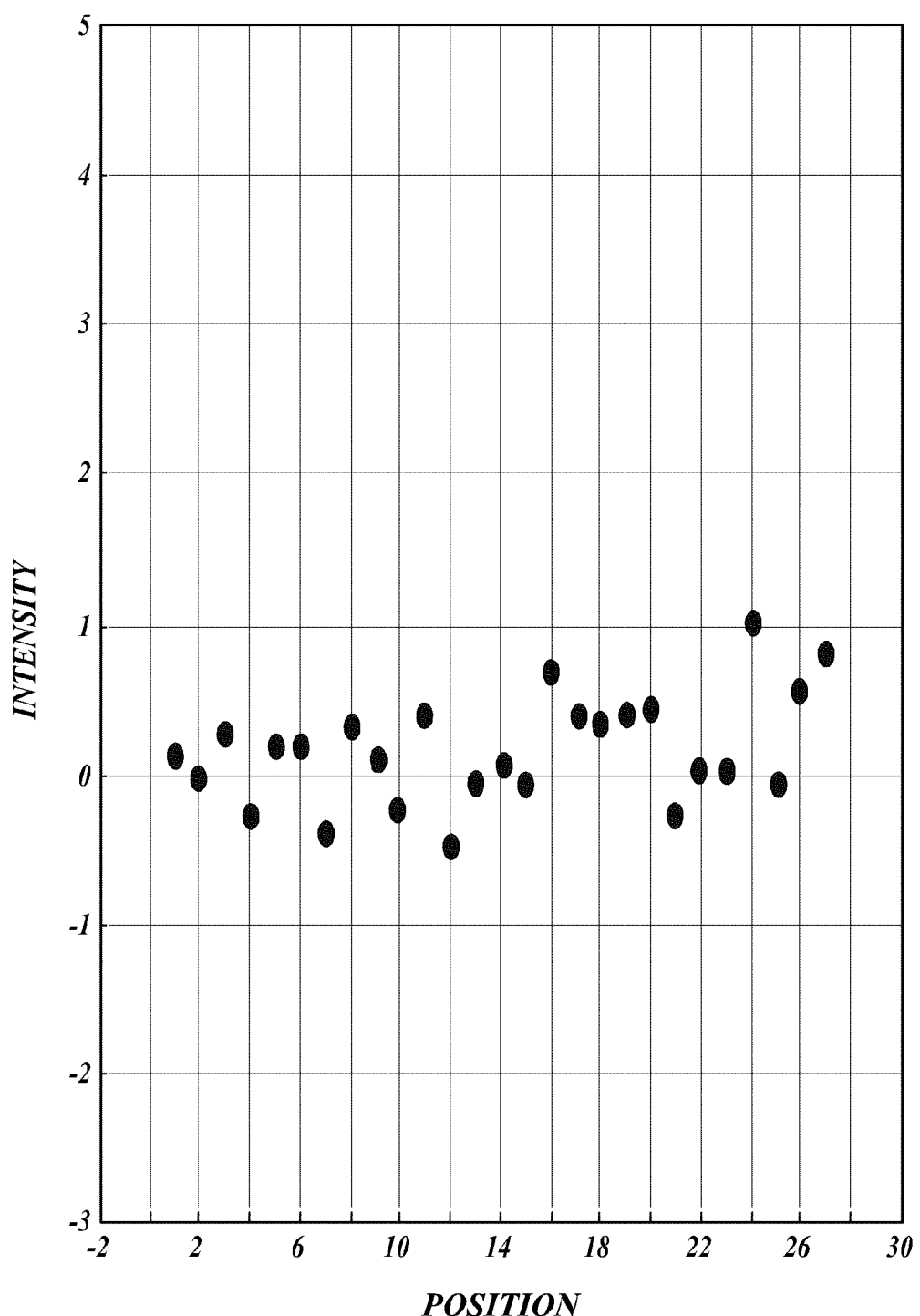
Figure 23B:
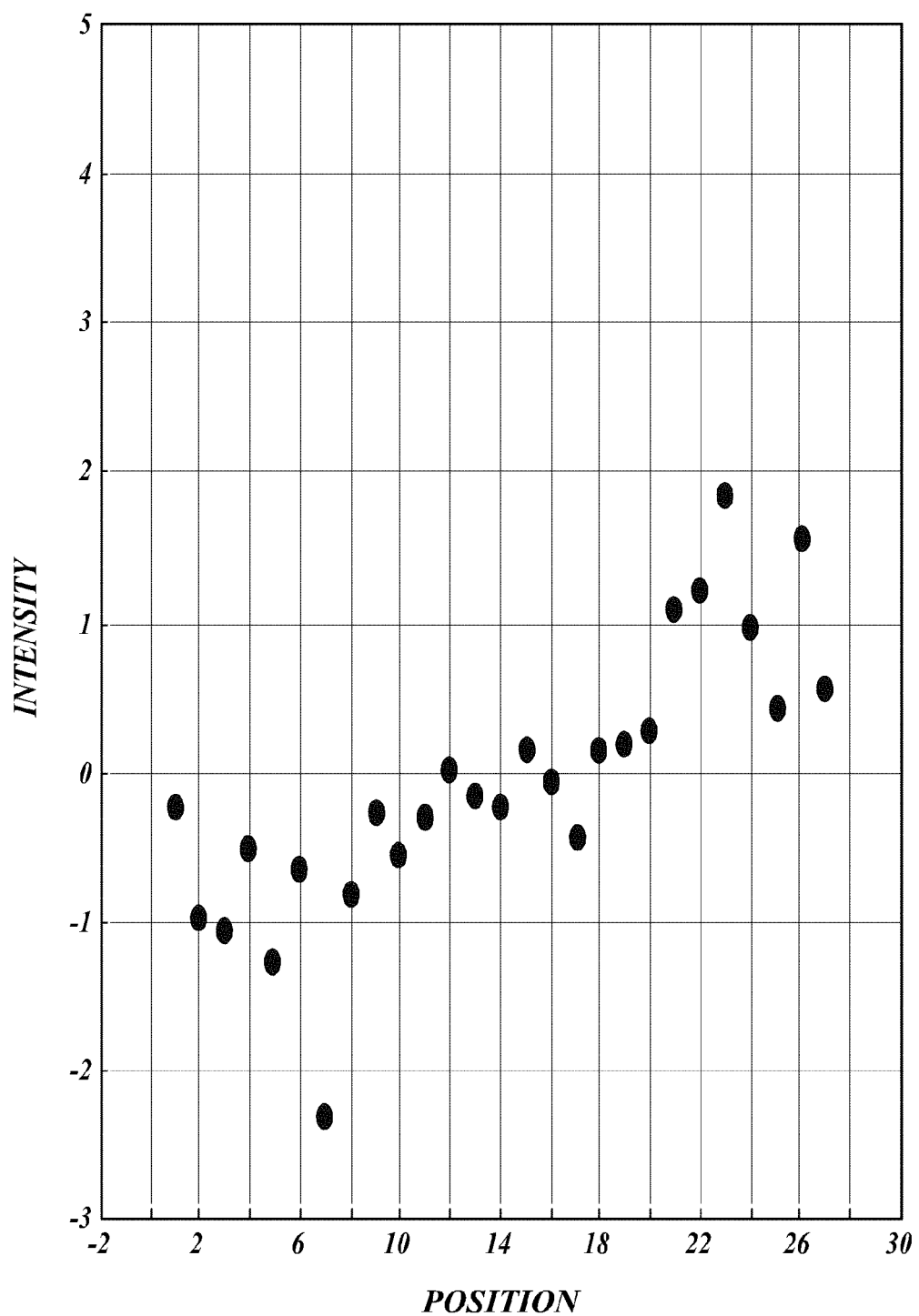
Figure 23C:
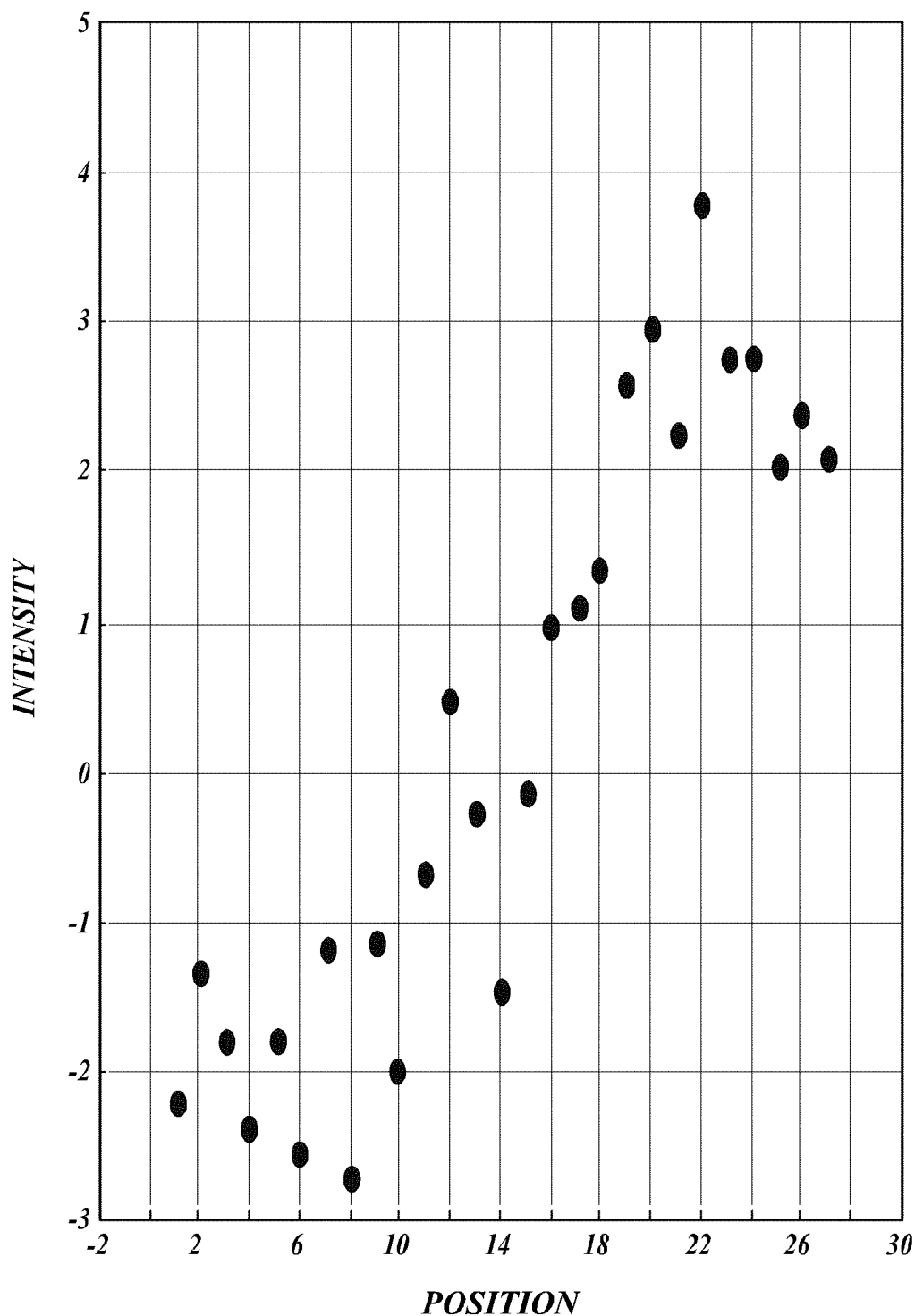
Figure 23D:
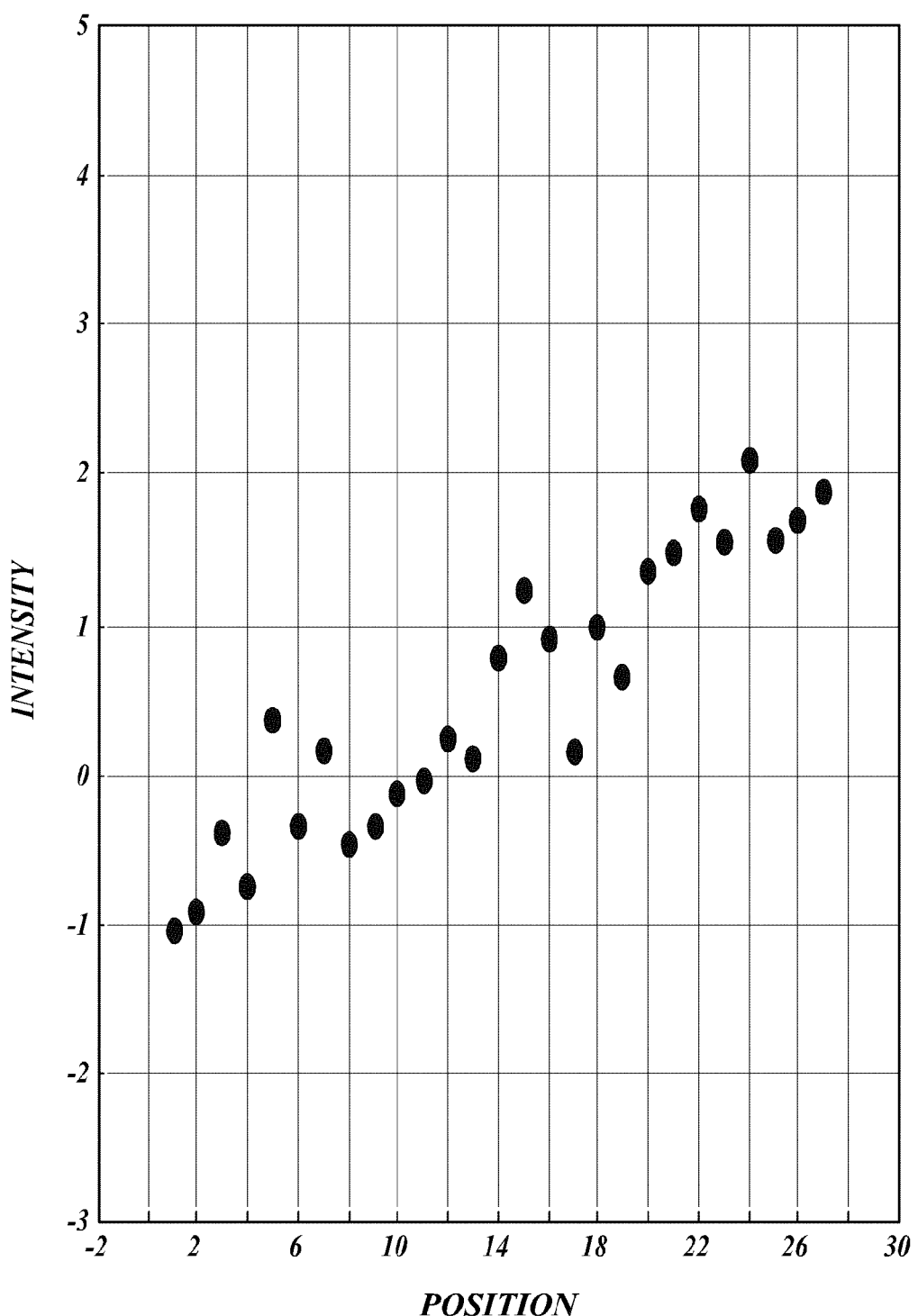
Figure 23E:
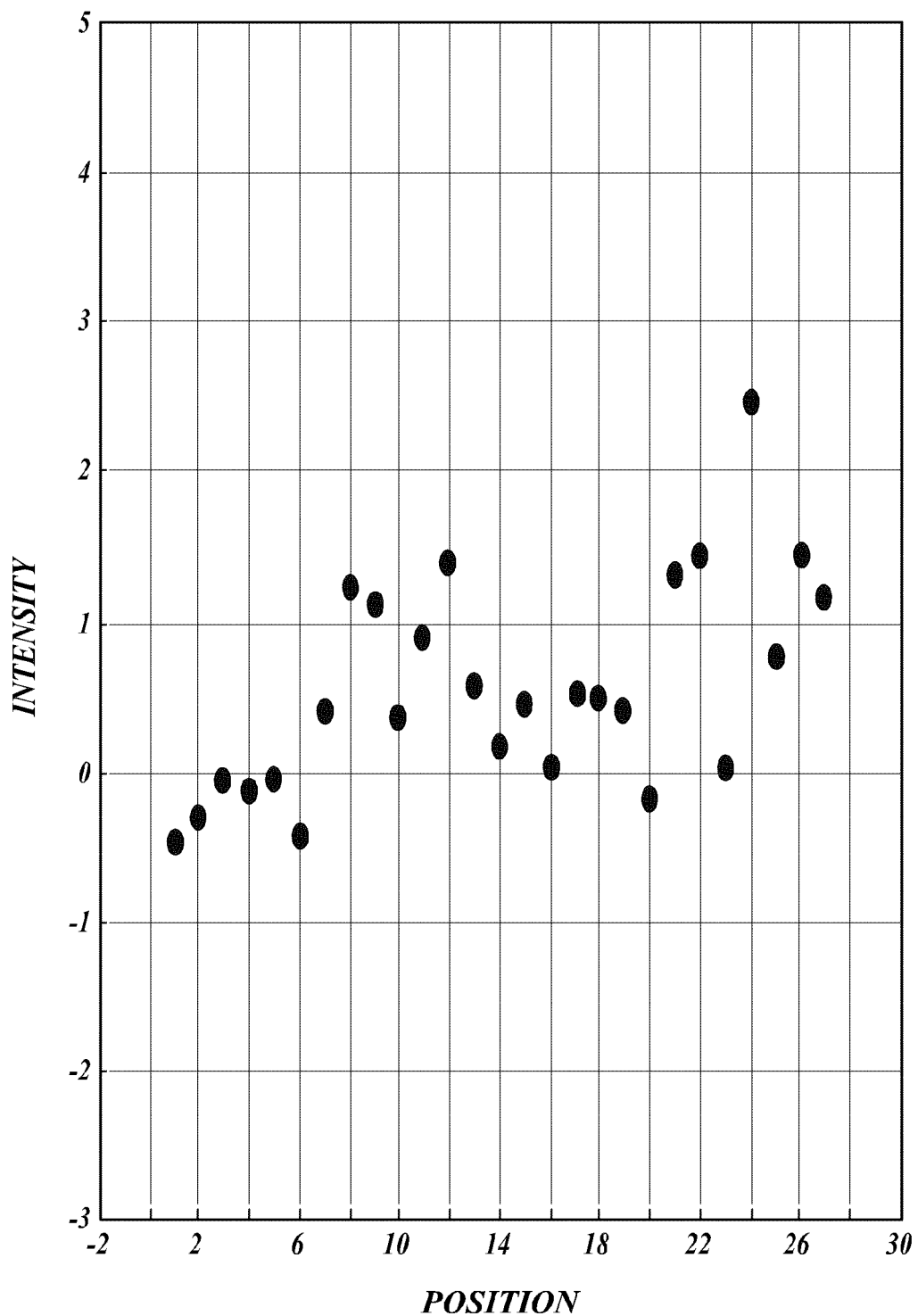
Figure 23F:
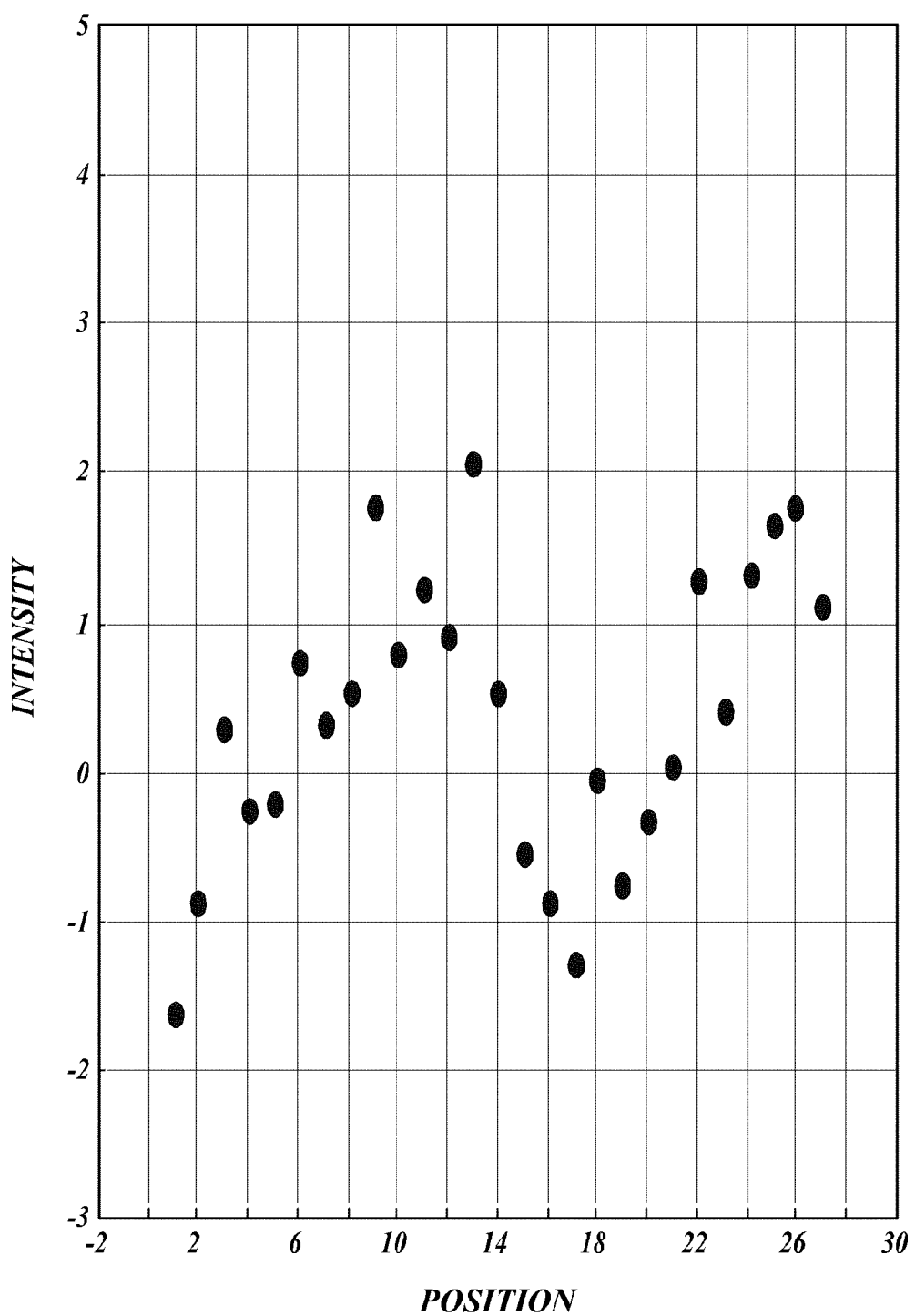

The pith location relative to the surfaces of a lumber cross section can be estimated if at least 2 points can be located around that cross section whose vector direction to pith can be established. The pith (70) will be located at the intersection of these two directional vectors (see FIGS. 21 and 22). There are several ways of inferring these vectors. As already discussed, any points on a surface whose T2 peaks are identical (P1-P2=0) must be at an $\alpha$ angle of 0, 45 or 90 degrees. Similarly any surface point whose T2 peaks are maximum must be at an $\alpha$ angle equal to half the view angle. The needed pair of pith vectors can be derived from more than one surface. Where more than 2 pith vectors are identified, the pith location can be more accurately estimated using methods such as least squares. Another method of estimating a pith vector is to compare the P1-P2 profiles on opposite faces (FIGS. 23A-F). Locations of equal-magnitude and opposite-sign P1-P2 profile slope indicate identical $\alpha$ angles. A line connecting these two opposite face points defines another pith vector.

Using one method alone may not achieve the desired accuracy in every situation, so, using complementary methods should improve the overall accuracy. Such approaches can be applied to green lumber, dry lumber, and other types of fibrous material for improving automatic grading, sorting, and other processes.

While the embodiments of the invention have been illustrated and described, as noted above, many changes can be made without departing from the spirit and scope of the invention. Accordingly, the scope of the invention is not limited by the disclosure of the embodiments. Instead, the invention should be determined entirely by reference to the claims that follow.

What is claimed is:

1. A method for determining dive angle of a fibrous material, the method comprising the steps of:
   projecting a light beam onto a surface of the fibrous material;
   detecting intensity of reflection of the light beam at two or more locations; and
   determining dive angle based on at least one difference between reflection intensities at the two or more locations.

2. The method of claim 1 further comprising the step of:
   locating light intensity detectors in proximity to local minimums in intensity.

3. The method of claim 2 further comprising the step of:
   locating a first minimum as an intersection point between tangent lines at flanks of peaks of a plot of the intensities.

4. The method of claim 3 further comprising the step of:
   locating a second local minimum 180 degrees away from the first local minimum.

5. The method of claim 2 further comprising the step of:
   finding a difference between intensities associated with the first local minimum and the second local minimum.

6. The method of claim 2 further comprising the step of:
   defining relative minima from an azimuth axis defined by a long axis of the diffused reflection pattern.

7. The method of claim 1 wherein the fibrous material is wood.

8. The method of claim 1 wherein the two locations are aligned with an axis of a tracheid of the fibrous material.

9. The method of claim 1 wherein the two locations are aligned with an axis of the fibrous material.

10. The method of claim 1 wherein the two locations are on opposite sides of the light beam.

11. The method of claim 1 further comprising the step of:
    calculating a surface angle for the fibrous material.

12. The method of claim 11 further comprising the step of:
    using the surface angle to increase accuracy of the determined dive angle.

13. A method for determining dive angle of a fibrous material, the method comprising the steps of:
    projecting a light beam onto a surface of the fibrous material;
    detecting intensity of reflection of the light beam at two or more locations along fixed axes of the fibrous material; and determining dive angle based on at least one difference between reflection intensities at the two or more locations.

14. A method for determining dive angle of a fibrous material, the method comprising the steps of:
projecting a light beam onto a surface of the fibrous material;
detecting intensity of reflection of the light beam at two or more locations at more than one viewing angle; and
determining dive angle based on at least one difference between reflection intensities at the two or more locations.

* * * * *